United States Patent
Kobayashi

(10) Patent No.: US 8,476,397 B2
(45) Date of Patent: Jul. 2, 2013

(54) PHENOXAZINE POLYMER COMPOUND AND LIGHT EMITTING DEVICE USING THE SAME

(75) Inventor: Satoshi Kobayashi, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/001,754

(22) PCT Filed: Jun. 26, 2009

(86) PCT No.: PCT/JP2009/062170
§ 371 (c)(1),
(2), (4) Date: Dec. 28, 2010

(87) PCT Pub. No.: WO2010/001982
PCT Pub. Date: Jan. 7, 2010

(65) Prior Publication Data
US 2011/0108820 A1    May 12, 2011

(30) Foreign Application Priority Data
Jun. 30, 2008    (JP) .................................. 2008-170241

(51) Int. Cl.
*C08G 18/00*        (2006.01)

(52) U.S. Cl.
USPC ................. 528/62; 528/163; 528/94; 528/99; 528/118; 528/377; 528/403; 528/423; 544/10; 544/38; 347/1

(58) Field of Classification Search
USPC .............. 528/62, 163, 94, 99, 118, 377, 403, 528/423; 544/10, 38; 347/1
See application file for complete search history.

(56) References Cited

U.S. PATENT DOCUMENTS

| | | | |
|---|---|---|---|
| 2004/0072989 | A1 | 4/2004 | Son et al. |
| 2004/0127666 | A1 | 7/2004 | Inbasekaran et al. |
| 2009/0256475 | A1 | 10/2009 | Nakatani et al. |
| 2009/0302748 | A1 | 12/2009 | Nakatani et al. |

FOREIGN PATENT DOCUMENTS

| | | | |
|---|---|---|---|
| JP | 2003-165829 | A | 6/2003 |
| JP | 2004-137456 | A | 5/2004 |
| JP | 2005-236096 | A | 9/2005 |
| JP | 2005-302657 | A | 10/2005 |
| JP | 2006-511659 | A | 4/2006 |
| JP | 2007291191 | * | 11/2007 |
| JP | 2008-133463 | A | 6/2008 |
| WO | 2008/016067 | A1 | 2/2008 |
| WO | 2008/032720 | A1 | 3/2008 |

OTHER PUBLICATIONS

Machine-generated English translation of JP 2008-133463 issued Jun. 12, 2008, to Sumitomo Chemical Co., Ltd.
Machine-generated English translation of JP 2003-165829 issued Jun. 10, 2003, to Toppan Printing Co., Ltd.
Machine-generated English translation of JP 2005-236096 issued Sep. 2, 2005, to Konica Minolta Holdings, Inc.
Machine-generated English translation of JP 2005-302657 issued Oct. 27, 2005, to Sharp Corp.
Machine-generated English translation of JP 2004-137456 issued May 13, 2004, to Samsung SDI Co., Ltd.
English-language Translation of Chinese Office Action issued on Oct. 9, 2012 by the Chinese Patent Office in corresponding Chinese Patent Application No. 200980133479.3.
"Transition Metal Catalyzed Synthesis of Arylamines and Aryl Ethers from Aryl Halides and Triflates: Scope and Mechanism", John F. Hartwig, Angewandte Chemie International Edition, 1998, vol. 37, Issue 15, pp. 2046-2067.

* cited by examiner

*Primary Examiner* — Shane Fang
(74) *Attorney, Agent, or Firm* — Sughrue Mion, PLLC

(57) ABSTRACT

A polymer compound comprising a residue of a compound represented by the following formula (0):

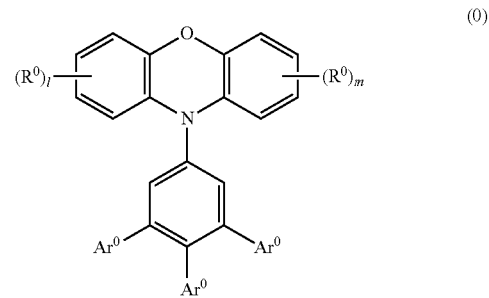

wherein $Ar^0$ represents a substituent such as a hydrogen atom, an alkyl group, an alkoxy group, an aryl group and the like, or a group represented by the following formula (A), at least two $Ar^0$s are groups represented by the following formula (A), $R^0$ represents a substituent such as an alkyl group, an alkoxy group, an aryl group and the like, l and m represent an integer of 0 to 3,

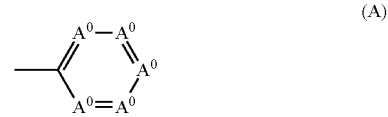

wherein $A^0$ represents $-N=$ or $-C(R^2)=$. $R^2$ represents a substituent such as a hydrogen atom, an alkyl group, an alkoxy group, an aryl group and the like.

16 Claims, No Drawings

PHENOXAZINE POLYMER COMPOUND AND LIGHT EMITTING DEVICE USING THE SAME

CROSS REFERENCE TO RELATED APPLICATIONS

This application is a National Stage of International Application No. PCT/JP2009/062170 filed Jun. 26, 2009, which claims priority from Japanese Patent Application No. 2008-170241 filed Jun. 30, 2008, the contents of all of which are incorporated herein by reference in their entirety.

TECHNICAL FIELD

The present invention relates to a phenoxazine polymer compound and a light emitting device using the same.

BACKGROUND ART

A polymer compound having on its main chain skeleton a phenoxazine-diyl group having an alkyl group as the substituent is soluble in a solvent and capable of forming an organic layer in a light emitting device by an application method, because of this reason, this polymer is investigated as a light emitting material (JP-A No. 2004-137456).

DISCLOSURE OF THE INVENTION

The above-described polymer compound, however, has not necessarily sufficient chromatic purity.

The present invention has an object of providing a polymer compound having excellent chromatic purity.

In a first aspect, the present invention provides a polymer compound comprising a residue of a compound represented by the following formula (0)

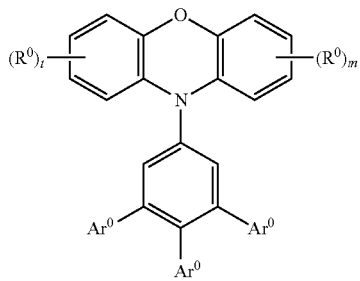

(wherein $Ar^0$ represents a hydrogen atom, an alkyl group, an alkoxy group, an aryl group, an aryloxy group, an arylalkyl group, an arylalkoxy group, an alkenyl group, an arylalkenyl group, an alkynyl group, an arylalkynyl group, amino group, a substituted amino group, a silyl group, a substituted silyl group, a halogen atom, an acyl group, an acyloxy group, an amide group, a mono-valent heterocyclic group, a heterocyclic oxy group, a carboxyl group, a substituted carboxyl group, a nitro group, a cyano group or a group represented by the following formula (A). A plurality of $Ar^0$s may be the same or different, and at least two $Ar^0$s are groups represented by the following formula (A). $R^0$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a substituted amino group, a silyl group, a substituted silyl group, a halogen atom, an acyl group, an acyloxy group, an amide group, a mono-valent heterocyclic group, a heterocyclic oxy group, a carboxyl group, a substituted carboxyl group, a nitro group or a cyano group. l and m each independently represent an integer of 0 to 3. When l+m is 2 or more, a plurality of $R^0$s may be the same or different.)

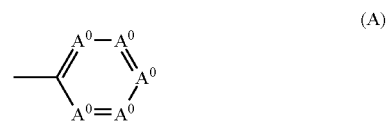

(wherein $A^0$ represents —N= or —C($R^2$)=. $R^2$ represents a hydrogen atom, an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a substituted amino group, a silyl group, a substituted silyl group, a halogen atom, an acyl group, an acyloxy group, an amide group, a mono-valent heterocyclic group, a heterocyclic oxy group, a carboxyl group, a substituted carboxyl group, a nitro group or a cyano group. A group represented by $R^2$ optionally has a substituent. A plurality of $A^0$s may be the same or different.).

In a second aspect, the present invention provides a compound represented by the following formula (9-0):

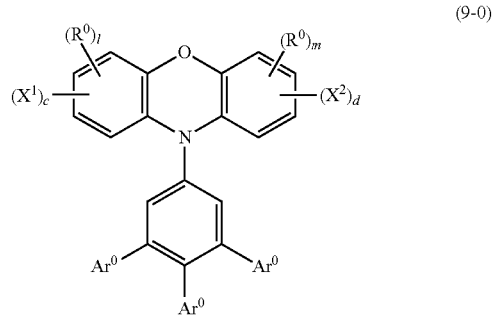

(wherein $Ar^0$, $R^0$, l and m represent the same meaning as described above. $X^1$ and $X^2$ each independently each independently represent a group capable of participating in polymerization. c and d represent an integer of 0 to 4. c+l is 4 or less, and d+m is 4 or less. When there exist a plurality of $X^1$s, these may be the same or different. When there exist a plurality of $X^2$s, these may be the same or different.).

In a third aspect, the present invention provides a method of producing a polymer compound comprising a repeating unit represented by the following formula (0'), comprising polymerizing a compound represented by the following formula (10-0) in the presence of a transition metal catalyst:

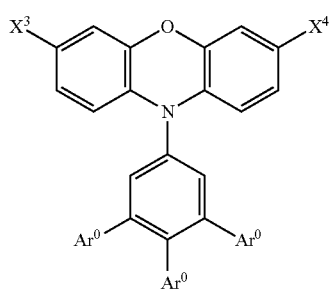

(10-0)

(wherein Ar⁰ represents the same meaning as described above. X³ and X⁴ each independently represent a halogen atom, —B(OH)₂, a borate ester residue, —MgX⁵ (X⁵ represents a halogen atom), a stannyl group, an alkyl sulfonate group, an aryl sulfonate group or an arylalkyl sulfonate group.)

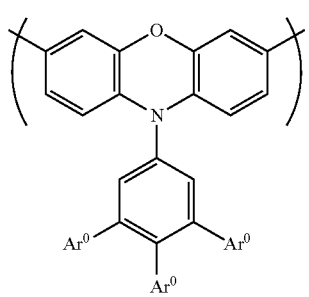

(0′)

(wherein Ar⁰ represents the same meaning as described above.).

In a fourth aspect, the present invention provides a method of producing a polymer compound comprising a repeating unit represented by the following formula (2′), comprising polymerizing a compound represented by the following formula (10) in the presence of a transition metal catalyst:

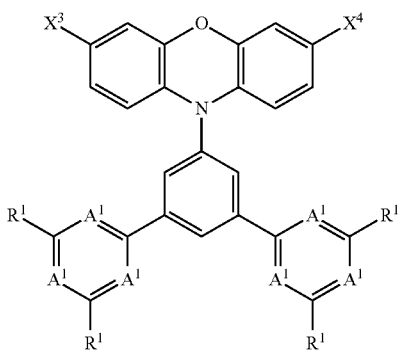

(10)

(wherein R¹ represents a mono-valent alicyclic hydrocarbon group, an aryl group or a mono-valent heterocyclic group, A¹ represents —N= or —C(R)=. R² represents the same meaning as described above, Four R¹s may be the same or different. X³ and X⁴ represent the same meaning as described above. Six A¹s may be the same or different.)

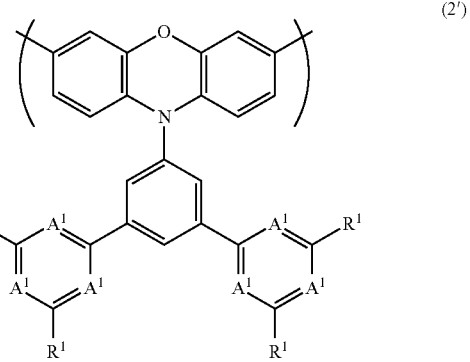

(2′)

(wherein A¹ and R¹ represent the same meaning as described above.).

In a fifth aspect, the present invention provides a compound represented by the following formula (11):

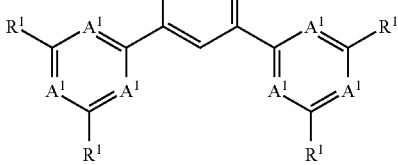

(11)

(wherein R¹ and A¹ represent the same meaning as described above. X⁵ represents a chlorine atom, a bromine atom, an iodine atom, an alkylsulfonyl group, an arylsulfonyl group or an arylalkylsulfonyl group.).

In a sixth aspect, the present invention provides a compound represented by the following formula (12):

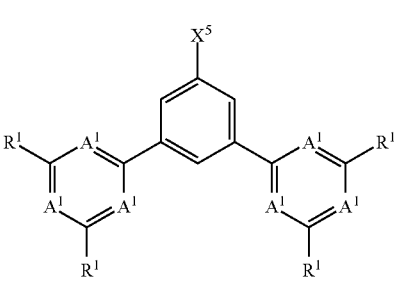

(12)

(wherein R¹ and A¹ represent the same meaning as described above.).

In a seventh aspect, the present invention provides a composition comprising the above-described polymer compound.

In an eighth aspect, the present invention provides a film comprising the above-described polymer compound, and an organic transistor having the film.

In a ninth aspect, the present invention provides a light emitting device having electrodes consisting of an anode and a cathode, and a layer comprising the above-described polymer compound disposed between the electrodes, and a surface light source and a display, using the light emitting device.

MODES FOR CARRYING OUT THE INVENTION

The present invention will be illustrated in detail below. In the present description, "residue of compound" means an atomic group remaining after removing N hydrogen atoms from the compound. Here, N represents an integer of 1 or more, and usually an integer of 1 to 3.

<Polymer Compound>

The polymer compound of the present invention is a polymer compound comprising a residue of a compound represented by the following formula (0).

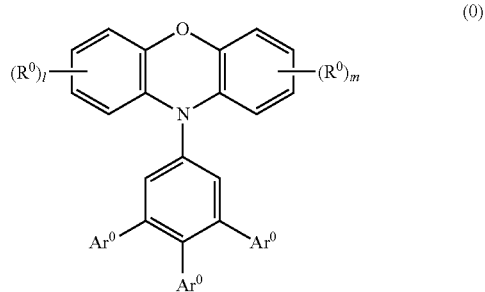

(0)

(wherein $Ar^0$ represents a hydrogen atom, an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a substituted amino group, a silyl group, a substituted silyl group, a halogen atom, an acyl group, an acyloxy group, an amide group, a mono-valent heterocyclic group, a heterocyclic oxy group, a carboxyl group, a substituted carboxyl group, a nitro group, a cyano group or a group represented by the following formula (A). A plurality of $Ar^0$s may be the same or different, and at least two $Ar^0$s are groups represented by the following formula (A). $R^0$ represents an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a substituted amino group, a silyl group, a substituted silyl group, a halogen atom, an acyl group, an acyloxy group, an amide group, a mono-valent heterocyclic group, a heterocyclic oxy group, a carboxyl group, a substituted carboxyl group, a nitro group or a cyano group. l and m each independently represent an integer of 0 to 3. When l+m is 2 or more, a plurality of $R^0$s may be the same or different.).

The alkyl group represented by $Ar^0$ may be any of linear, branched or cyclic, and has a carbon atom number of usually 1 to 30 and examples thereof include a methyl group, an ethyl group, a n-propyl group, an isopropyl group, a n-butyl group, an isobutyl group, a sec-butyl group, a tert-butyl group, a n-pentyl group, an isoamyl group, a n-hexyl group, a cyclohexyl group, a n-heptyl group, a n-octyl group and a trifluoromethyl group.

The alkoxy group represented by $Ar^0$ may be any of linear, branched or cyclic, and has a carbon atom number of usually 1 to 30 and examples thereof include a methoxy group, an ethoxy group, a n-propyloxy group, an isopropyloxy group, a n-butoxy group, an isobutoxy group, a sec-butoxy group, a tert-butoxy group, a n-pentyloxy group, an isoamyloxy group, a n-hexyloxy group, a cyclohexyloxy group, a n-heptyloxy group, a n-octyloxy group and a trifluoromethoxy group.

The aryl group represented by $Ar^0$ is the same as explained and exemplified as the aryl group represented by $R^1$.

The aryloxy group represented by $Ar^0$ has a carbon atom number of usually 6 to 60 and examples thereof include a phenoxy group, $C_1$ to $C_{12}$ alkoxyphenoxy groups, $C_1$ to $C_{12}$ alkylphenoxy groups, a pentafluorophenyloxy group, a 1-naphthyloxy group, a 2-naphthyloxy group, a 1-anthracenyloxy group, a 2-anthracenyloxy group, a 9-anthracenyloxy group, a biphenyloxy group and a terphenyloxy group.

The arylalkyl group represented by $Ar^0$ has a carbon atom number of usually, 7 to 60 and examples thereof include phenyl-$C_1$ to $C_{12}$ alkyl groups, $C_1$ to $C_{12}$ alkoxyphenyl-$C_1$ to $C_{12}$ alkyl groups, $C_1$ to $C_{12}$ alkylphenyl-$C_1$ to $C_{12}$ alkyl groups, 1-naphthyl-$C_1$ to $C_{12}$ alkyl groups and 2-naphthyl-$C_1$ to $C_{12}$ alkyl groups.

The arylalkoxy group represented by $Ar^0$ has a carbon atom number of usually 7 to 60 and examples thereof include phenyl-$C_1$ to $C_{12}$ alkoxy groups such as a phenylmethoxy group, a phenylethoxy group, a phenylbutoxy group, a phenylpentyloxy group, a phenylhexyloxy group, a phenylheptyloxy group, a phenyloctyloxy group and the like; $C_1$ to $C_{12}$ alkoxyphenyl-$C_1$ to $C_{12}$ alkoxy groups, $C_1$ to $C_{12}$ alkylphenyl-$C_1$ to $C_{12}$ alkoxy groups, 1-naphthyl-$C_1$ to $C_{12}$ alkoxy groups and 2-naphthyl-$C_1$ to $C_{12}$ alkoxy groups.

The alkenyl group represented by $Ar^0$ has a carbon atom number of 2 to 30 and examples thereof include a vinyl group, a 1-propylenyl group, a 2-propylenyl group, a butenyl group, a pentenyl group, a hexenyl group, a heptenyl group, an octenyl group and a cyclohexenyl group.

The arylalkenyl group represented by $Ar^0$ has a carbon atom number of usually 8 to 60 and examples thereof include phenyl-$C_2$ to $C_{12}$ alkenyl groups, $C_1$ to $C_{12}$ alkoxyphenyl-$C_2$ to $C_{12}$ alkenyl groups, $C_1$ to $C_{12}$ alkylphenyl-$C_2$ to $C_{12}$ alkenyl groups, 1-naphthyl-$C_2$ to $C_{12}$ alkenyl groups and 2-naphthyl-$C_2$ to $C_{12}$ alkenyl groups.

The alkynyl group represented by $Ar^0$ has a carbon atom number of 2 to 30 and examples thereof include an ethynyl group, a 1-propynyl group, a 2-propylenyl group, a butynyl group, a pentynyl group, a hexynyl group, a heptynyl group, an octynyl group and a cyclohexylethynyl group.

The arylalkynyl group represented by $Ar^0$ has a carbon atom number of usually 8 to 60 and examples thereof include phenyl-$C_2$ to $C_{12}$ alkynyl groups, $C_1$ to $C_{12}$ alkoxyphenyl-$C_2$ to $C_{12}$ alkynyl groups, $C_1$ to $C_{12}$ alkylphenyl-$C_2$ to $C_{12}$ alkynyl groups, 1-naphthyl-$C_2$ to $C_{12}$ alkynyl groups and 2-naphthyl-$C_2$ to $C_{12}$ alkynyl groups.

The substituted amino group represented by $Ar^0$ is an amino group substituted by one or two groups selected from the group consisting of an alkyl group, an aryl group, an arylalkyl group and a mono-valent heterocyclic group. The alkyl group, aryl group, arylalkyl group and mono-valent heterocyclic group optionally have a substituent. The above-described substituted amino group has a carbon atom number of usually 1 to 60 not including the carbon atom number of the substituent and examples thereof include a methylamino group, a dimethylamino group, an ethylamino group, a diethylamino group, a n-propylamino group, a di(n-propyl) amino group, an isopropylamino group, a di(isopropyl)amino group, a di(n-'butyl)amino group, a di(isobutyl)amino group, a di(sec-butyl)amino group, a di(tert-butyl)amino group, a dicyclohexylamino group, a pyrrolidyl group, a piperidyl group, a phenylamino group, a diphenylamino group, $C_1$ to $C_{12}$ alkoxyphenylamino groups, di($C_1$ to $C_{12}$ alkoxyphenyl) amino groups and di($C_1$ to $C_{12}$ alkylphenyl)amino groups.

The substituted silyl group represented by $Ar^0$ is a silyl group substituted by one to three groups selected from the group consisting of an alkyl group, an aryl group, an arylalkyl group and a mono-valent heterocyclic group and has a carbon atom number of usually 1 to 60 The alkyl group, aryl group, arylalkyl group and mono-valent heterocyclic group optionally have a substituent. Examples of the substituted silyl group include a trimethylsilyl group, a triethylsilyl group, a tripropylsilyl group, a tri-isopropylsilyl group, a dimethylisopropylsilyl group, a tert-butyldimethylsilyl group, a triphenylsilyl group, a tribenzylsilyl group, a diphenylmethylsilyl group, a tert-butyldiphenylsilyl group and a dimethylphenylsilyl group. As the mono-valent heterocyclic group, mono-valent aromatic heterocyclic groups are preferable.

The halogen atom represented by $Ar^0$ includes a fluorine atom, a chlorine atom, a bromine atom and an iodine atom.

The acyl group represented by $Ar^0$ has a carbon atom number of usually 2 to 30 and examples thereof include an acetyl group, a propionyl group, a butyryl group, an isobutyryl group, a pivaloyl group, a benzoyl group, a trifluoroacetyl group and a pentafluorobenzoyl group.

The acyloxy group represented by $Ar^0$ has a carbon atom number of usually 2 to 30 and examples thereof include an acetoxy group, a propionyloxy group, a butyryloxy group, an isobutyryloxy group, a pivaloyloxy group, a benzoyloxy group, a trifluoroacetyloxy group and a pentafluorobenzoyloxy group.

The amide group represented by $Ar^0$ has a carbon atom number of usually 2 to 30 and examples thereof include a formamide group, an acetamide group, a propioamide group, a butyroamide group, a benzamide group, a trifluoroacetamide group, a pentafluorobenzamide group, a diformamide group, a diacetamide group, a dipropioamide group, a dibutyroamide group, a dibenzamide group, a ditrifluoroacetamide group and a dipentafluorobenzamide group.

The mono-valent heterocyclic group represented by $Ar^0$ is the same as one which is explained and exemplified as the mono-valent heterocyclic group represented by $R^1$ described later.

The heterocyclic oxy group represented by $Ar^0$ is a group represented by the formula: $Q^1$-O— (wherein $Q^1$ represents a mono-valent heterocyclic group) and has a carbon atom number of usually 2 to 30. The mono-valent heterocyclic group represented by $Q^1$ is the same as one which is explained and exemplified as the mono-valent heterocyclic group represented by $R^1$ described later. The heterocyclic oxy group optionally has a substituent on the mono-valent heterocyclic group, and the carbon atom number thereof does not include the carbon atom number of the substituent. Examples of the above-described heterocyclic oxy group include a thienyloxy group, $C_1$ to $C_{12}$ alkylthienyloxy groups, a pyrrolyloxy group, a furyloxy group, a pyridyloxy group, $C_1$ to $C_{12}$ alkylpyridyloxy groups, an imidazoyloxy group, a pyrazolyloxy group, a triazolyloxy group, an oxazolyloxy group, a thiazoleoxy group and a thiadiazoleoxy group.

The substituted carboxyl group represented by $Ar^0$ is a carboxyl group substituted by an alkyl group, an aryl group, an arylalkyl group or a mono-valent heterocyclic group, and has a carbon atom number of usually 2 to 30. Examples of the above-described substituted carboxyl group include a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentyloxycarbonyl group, a n-hexyloxycarbonyl group, a cyclohexyloxycarbonyl group, a n-heptyloxycarbonyl group, a n-octyloxycarbonyl group and a trifluoromethoxycarbonyl group.

The explanations and examples of the alkyl group, alkoxy group, aryl group, aryloxy group, arylalkyl group, arylalkoxy group, alkenyl group, arylalkenyl group, alkynyl group, arylalkynyl group, amino group, substituted amino group, silyl group, substituted silyl group, halogen atom, acyl group, acyloxy group, amide group, mono-valent heterocyclic group, heterocyclic oxy group, carboxyl group and substituted carboxyl group for $R^0$ are the same as those explained and exemplified in the section of $Ar^0$, and $R^0$ represents preferably an alkyl group, an alkoxy group, an aryl group, an arylalkyl group, an arylalkoxy group, an acyl group, an acyloxy group or a substituted carboxyl group.

The explanations and examples of the alkyl group, alkoxy group, aryl group, aryloxy group, arylalkyl group, arylalkoxy group, alkenyl group, arylalkenyl group, alkynyl group, arylalkynyl group, amino group, substituted amino group, silyl group, substituted silyl group, halogen atom, acyl group, acyloxy group, amide group, mono-valent heterocyclic group, heterocyclic oxy group, carboxyl group and substituted carboxyl group for $R^2$ are the same as those explained and exemplified in the section of $Ar^0$.

Among the compounds represented by the above-described formula (0), preferable are compounds represented by the following formula (0-1) from the standpoint of chromatic purity.

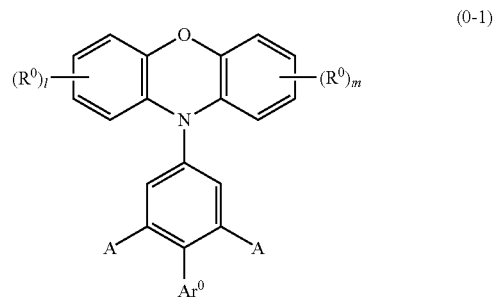

(0-1)

(wherein A represents a group represented by the above-described formula (A). A plurality of As may be the same or different. $Ar^0$, $R^0$, l and m represent the same meaning as described above.).

Among the compounds represented by the above-described formula (0-1), preferable are compounds represented by the following formula (1).

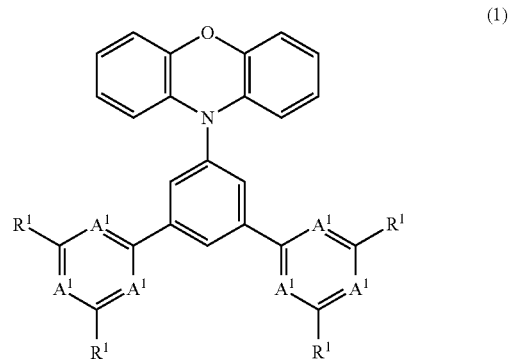

(1)

(wherein $R^1$ represents a mono-valent alicyclic hydrocarbon group, an aryl group or a mono-valent heterocyclic group. A group represented by $R^1$ optionally has a substituent. $A^1$ represents —N= or —C($R^2$)=, and $R^2$ represents the same meaning as described above. Six A¹s may be the same or different. Four R¹s may be the same or different.).

In the above-described formula (1), $R^1$ represents preferably an aryl group or a mono-valent aromatic heterocyclic group.

In the above-described formula (1), the mono-valent alicyclic hydrocarbon group represented by $R^1$ has usually a carbon atom number of 3 to 30, and may be mono-cyclic or bi- or more-cyclic. The mono-valent alicyclic hydrocarbon group includes cyclopropane, cyclobutane, cyclobutene, cyclopentane, cyclopentane, cyclohexane, cyclohexene and the like.

In the above-described formula (1), the aryl group represented by $R^1$ is an atomic group remaining after removing one hydrogen atom from an aromatic hydrocarbon compound, and may include groups having a condensed ring and bi- or more-cyclic groups. The aryl group has a carbon atom number of usually 6 to 60, preferably 6 to 30. Examples of the aryl group include a phenyl group, $C_1$ to $C_{12}$ alkoxyphenyl groups ($C_1$ to $C_{12}$ means that an organic group described directly after $C_1$ to $C_{12}$ has a carbon atom number (here, the carbon atom number in an alkoxy group in an alkoxyphenyl group) of 1 to 12. The same shall apply hereinafter.), $C_1$ to $C_{12}$ alkylphenyl groups, a pentafluorophenyl group, a 1-naphthyl group, a 2-naphthyl group, a 1-anthracenyl group, a 2-anthracenyl group, a 9-anthracenyl group, a biphenyl group and a terphenyl group, and from the standpoint of solubility in an organic solvent, device properties, easiness of synthesis and the like, preferable are $C_1$ to $C_{12}$ alkoxyphenyl groups and $C_1$ to $C_{12}$ alkylphenyl groups, particularly preferable are $C_1$ to $C_{12}$ alkylphenyl groups.

In the above-described formula (1), the mono-valent heterocyclic group represented by $R^1$ means an atomic group remaining after removing one hydrogen atom from a heterocyclic compound (namely, organic compounds having a cyclic structure in which elements constituting the ring include not only a carbon atom but also a hetero atom such as oxygen, sulfur, nitrogen, phosphorus, boron and the like contained in the ring). The mono-valent heterocyclic group has a carbon atom number of usually 2 to 30, preferably 2 to 15. In the mono-valent heterocyclic group, the heterocyclic ring optionally has a substituent, and the carbon atom number thereof does not include the carbon atom number of a substituent on the heterocyclic ring. The mono-valent heterocyclic group includes a thienyl group, $C_1$ to $C_{12}$ alkylthienyl groups, a pyrrolyl group, a furyl group, a pyridyl group, $C_1$ to $C_{12}$ alkylpyridyl groups, a piperidyl group, a quinolyl group, an isoquinolyl group and the like, and preferable are mono-valent aromatic heterocyclic groups, more preferable are a thienyl group, $C_1$ to $C_{12}$ alkylthienyl groups, a pyridyl group and $C_1$ to $C_{12}$ alkylpyridyl groups.

It is preferable that $A^1$ represents $-C(R^2)=$ and $R^1$ represents an aryl group, in the above-described formula (1).

In the above-described formulae (0), (0-1) and (1), $R^2$ preferably represents a hydrogen atom, an alkyl group, an alkoxy group, an aryl group, an arylalkyl group, an arylalkoxy group, an acyl group, an acyloxy group or a substituted carboxyl group.

When $R^1$ has a substituent containing an alkyl group, the alkyl group contained in the substituent has preferably a carbon atom number of 4 or more, from the standpoint of the solubility of a polymer compound in a solvent. Further, when $R^2$ is an alkyl group, the alkyl group preferably has a carbon atom number of 4 or more and when $R^2$ is a group containing an alkyl group, this alkyl group is preferably an alkyl group having a carbon atom number of 4 or more, from the standpoint of the solubility of a polymer compound in a solvent.

The compounds represented by the above-described formulae (0), (0-1) and (1) include the following compounds.

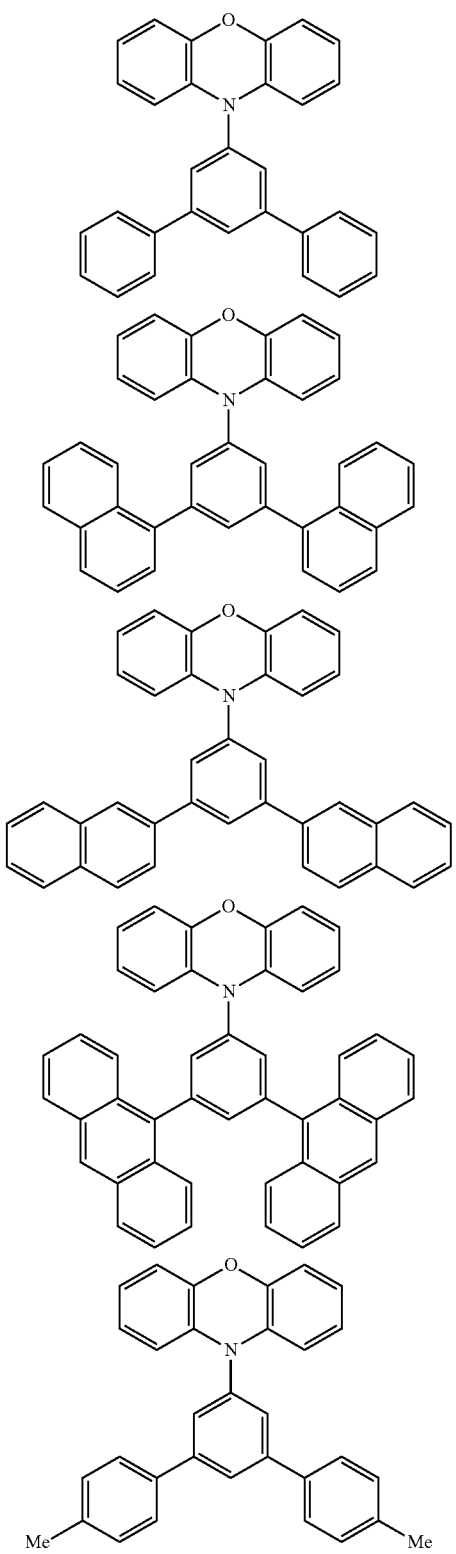

-continued
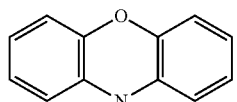
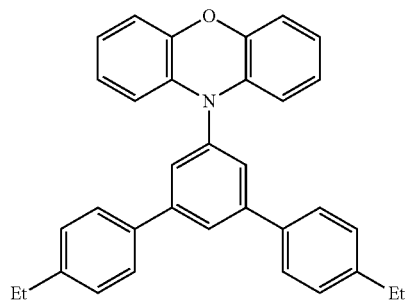
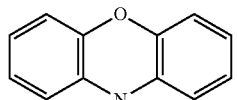
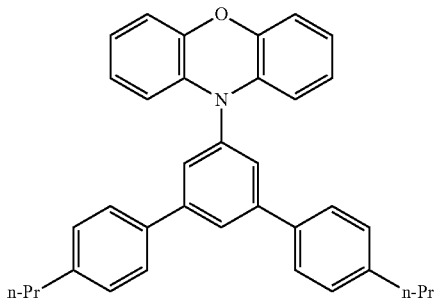
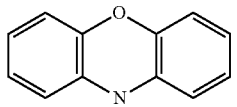
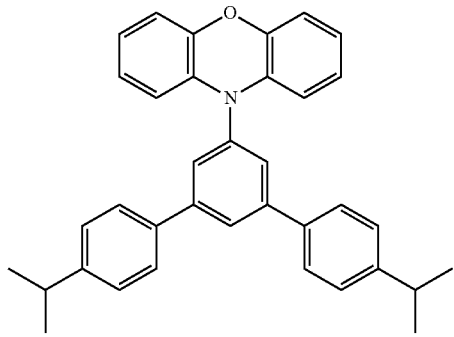
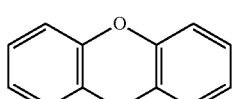
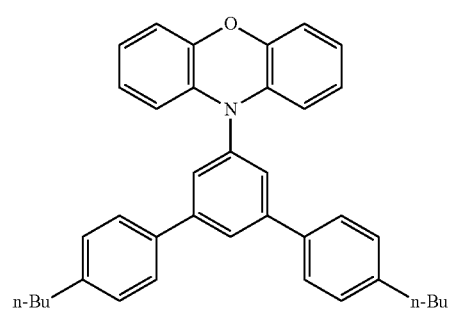
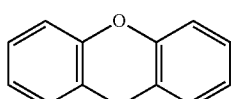
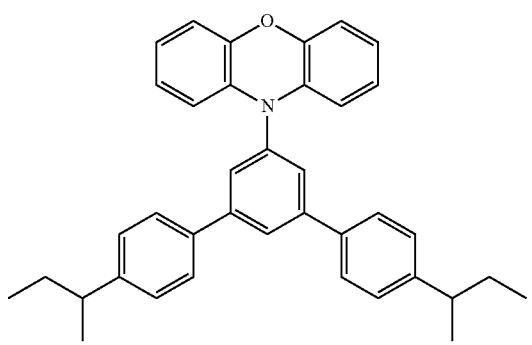
-continued
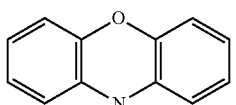
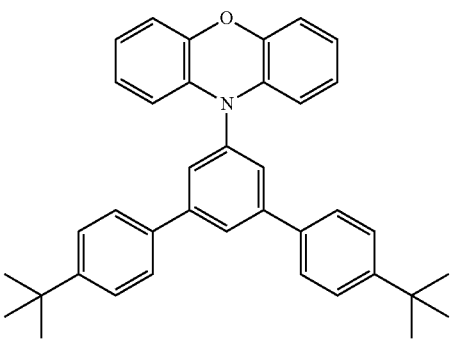
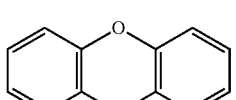
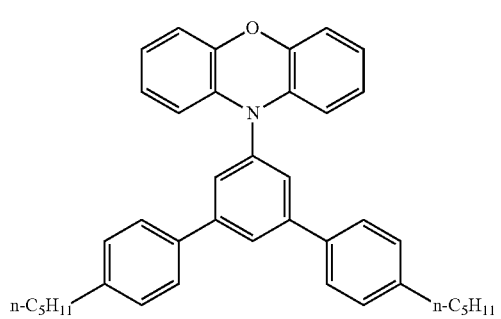
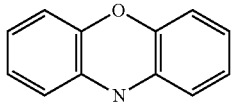
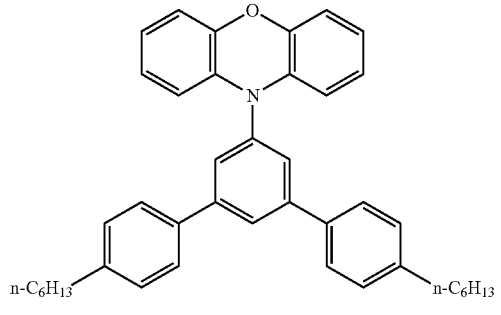
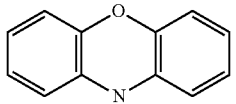
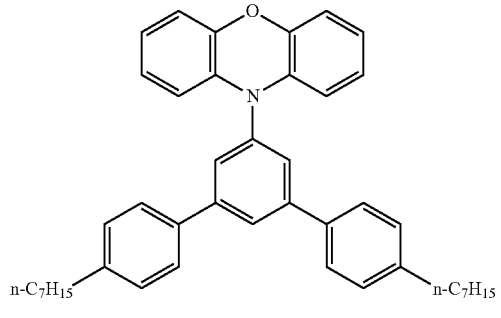
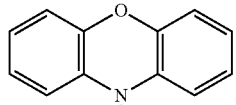
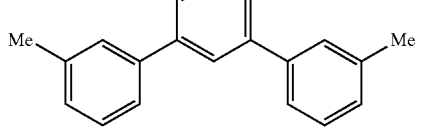

-continued
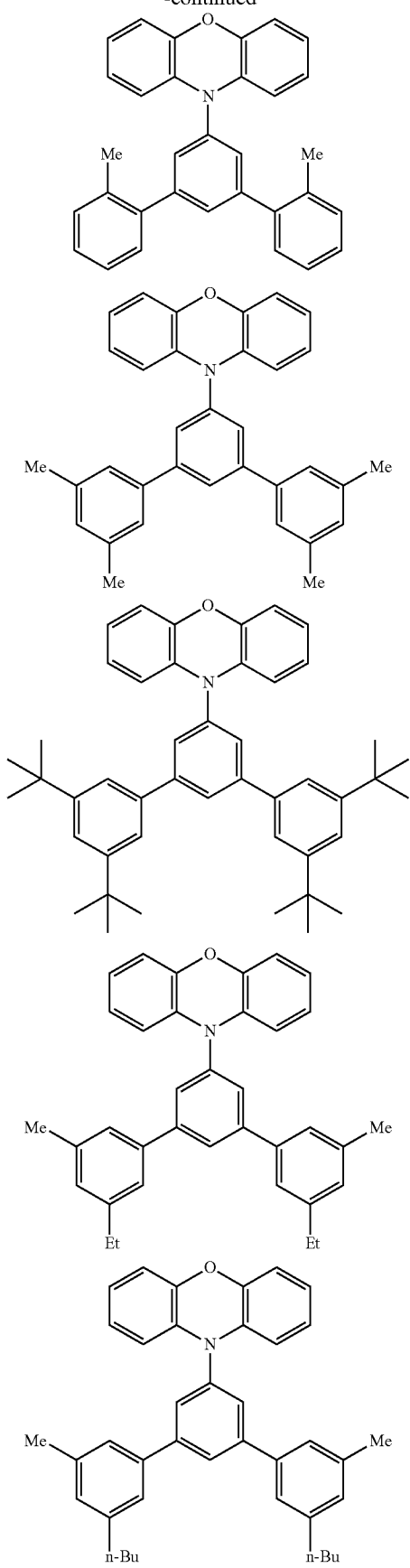
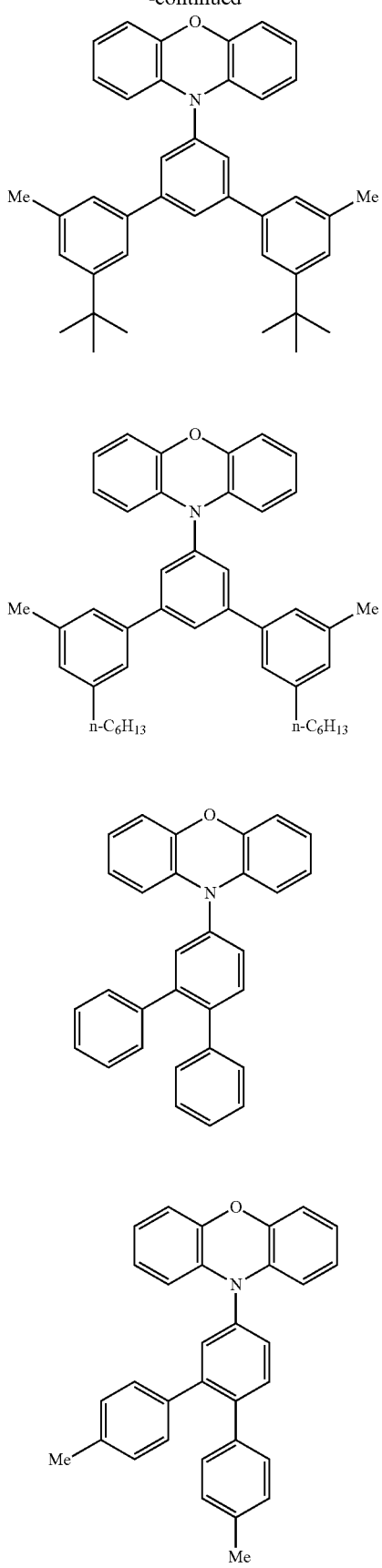

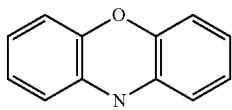
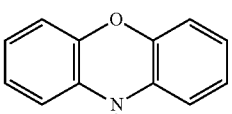

-continued
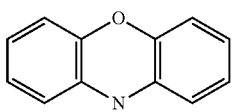
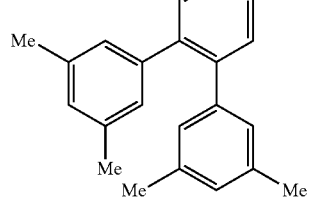
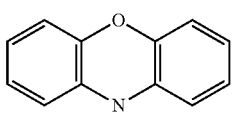
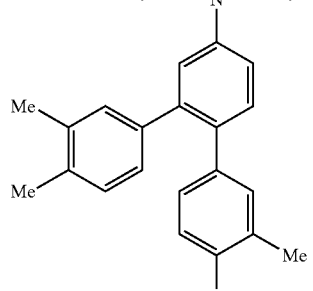
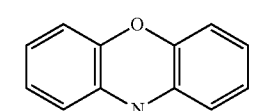
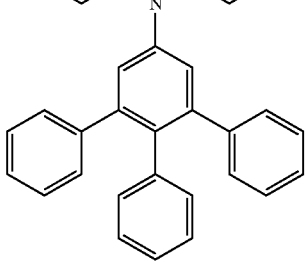
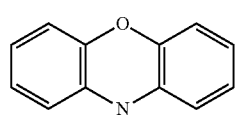
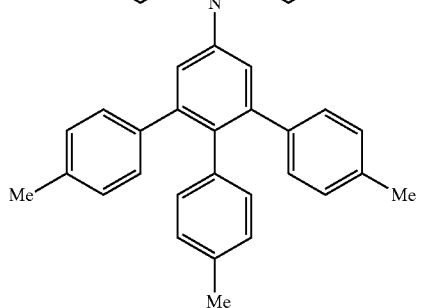
-continued
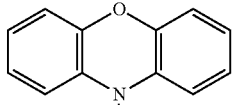
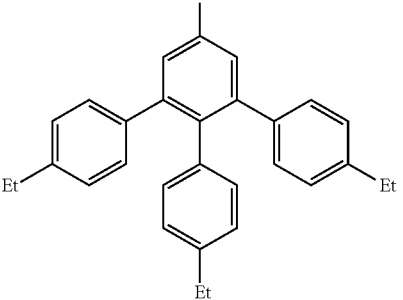
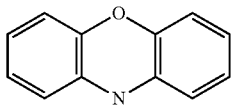
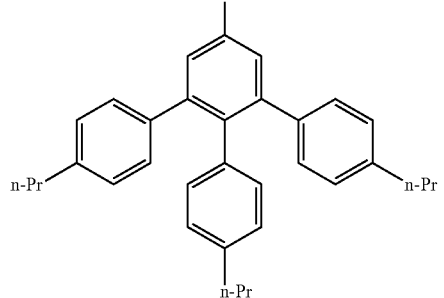
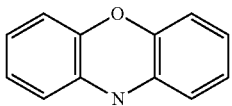
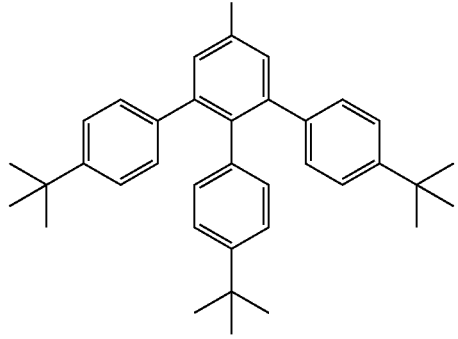
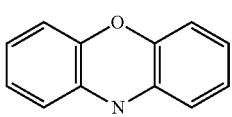
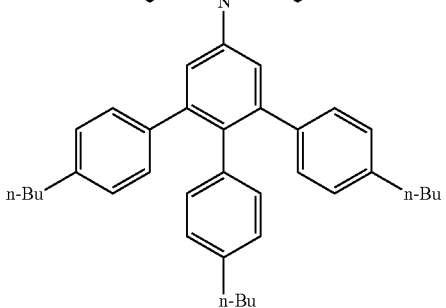

-continued
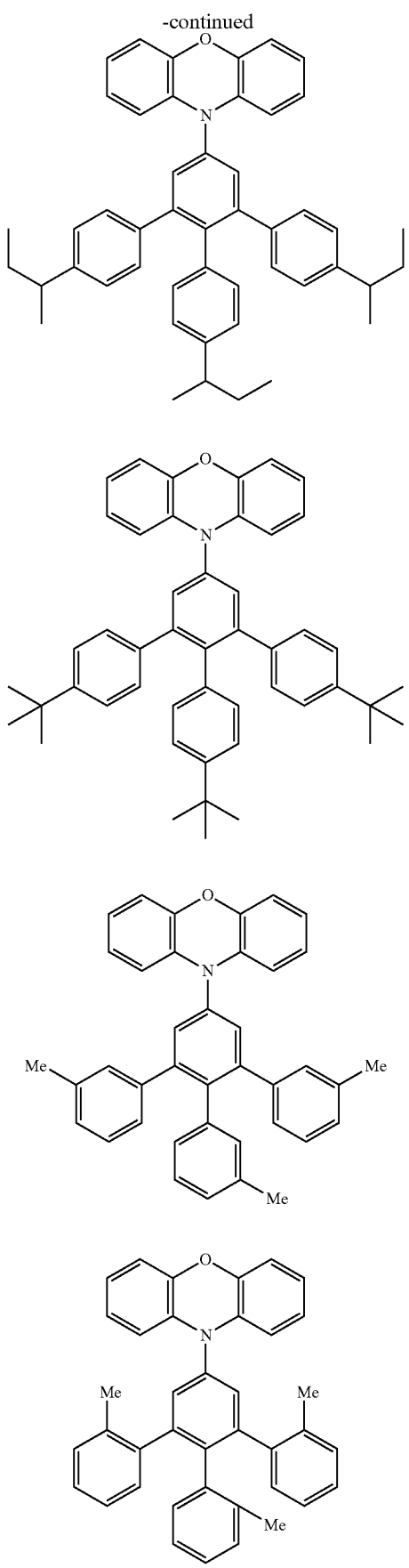
-continued
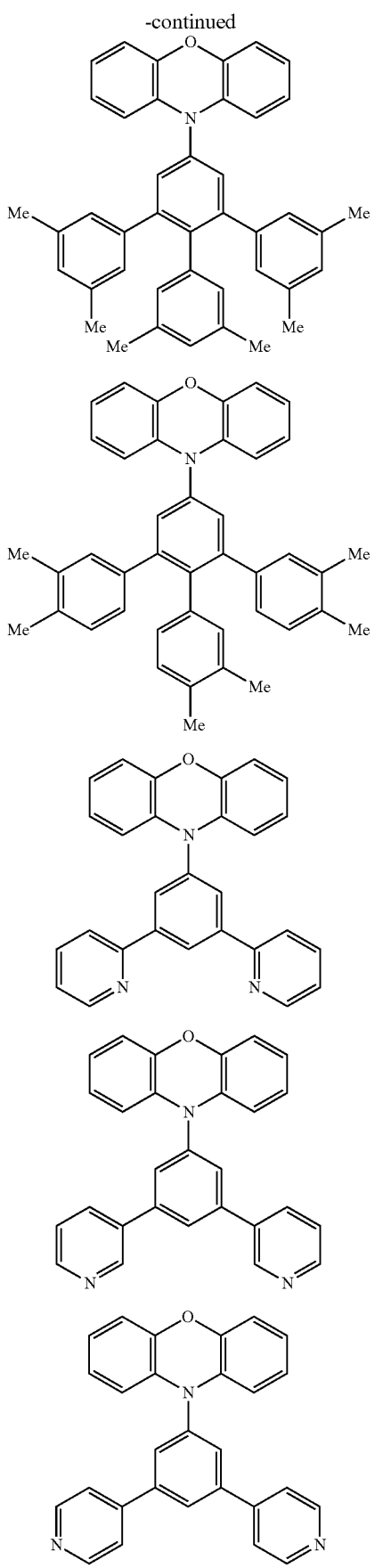

-continued
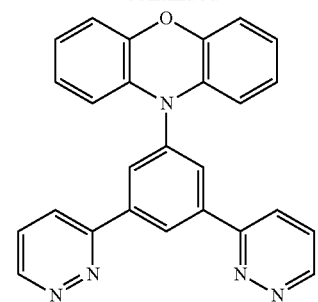
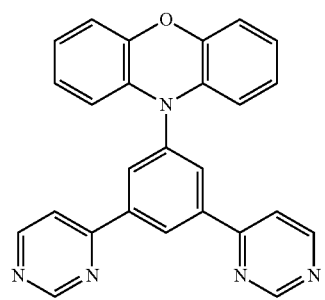
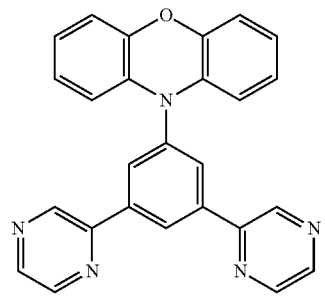
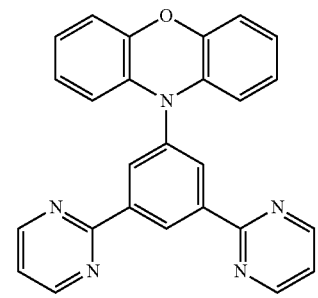
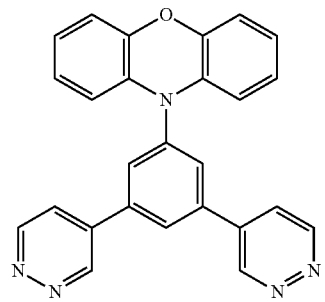
-continued
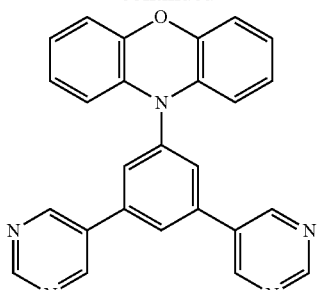
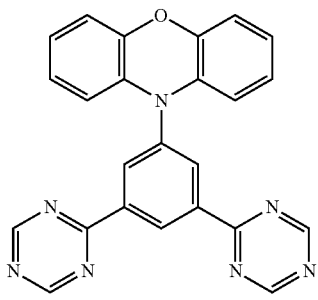
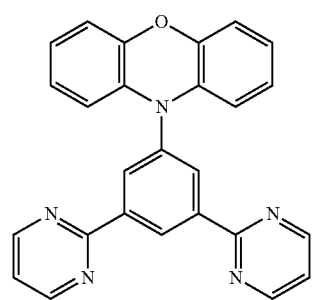
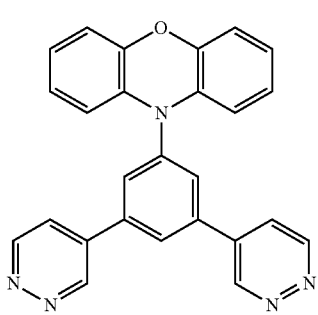
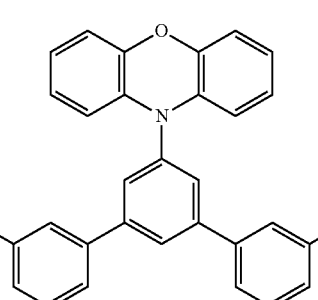
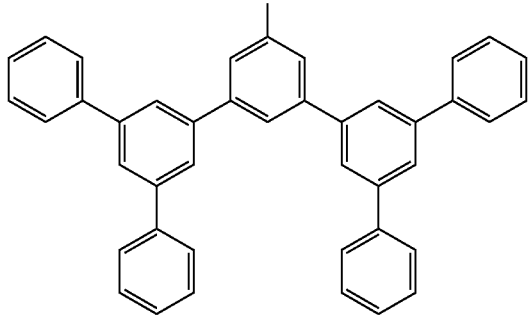

23
-continued
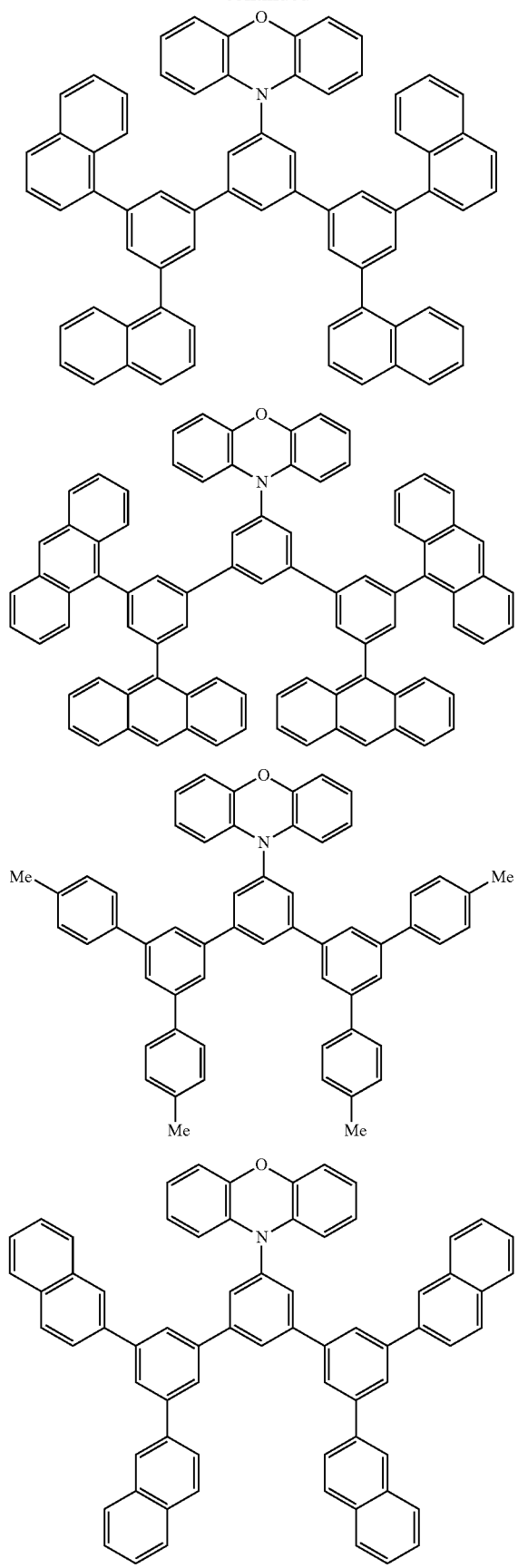
24
-continued
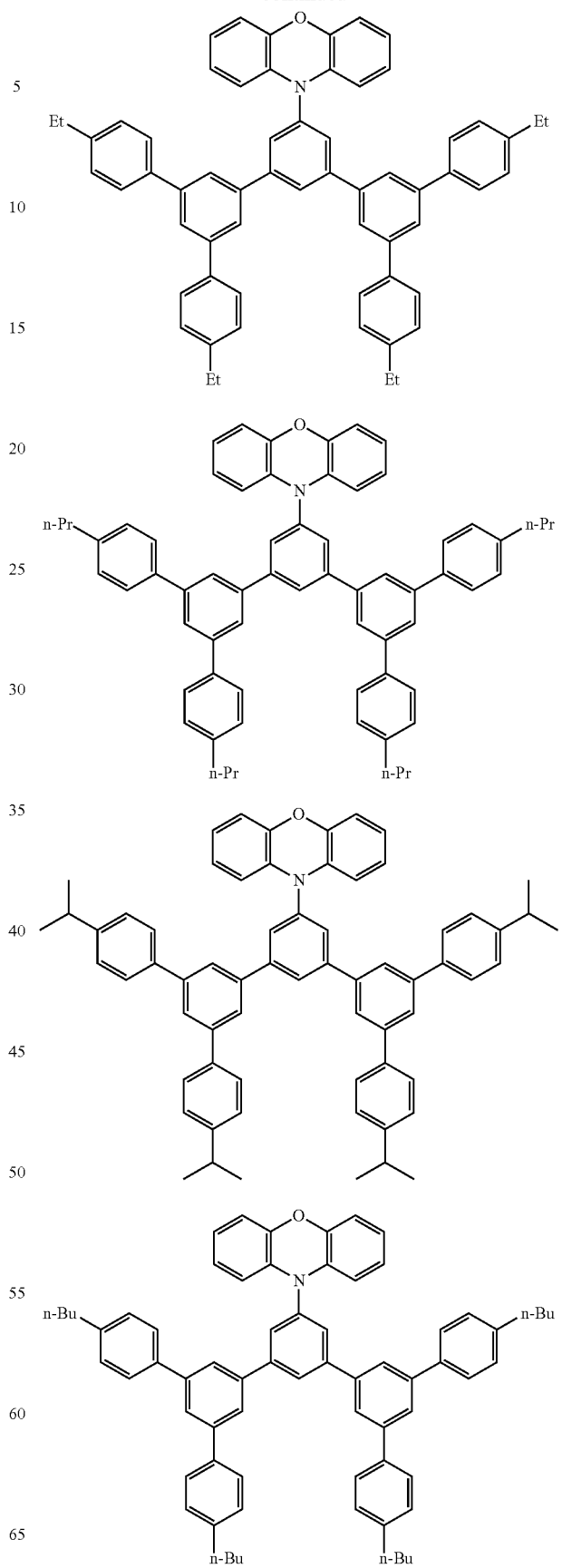

25
-continued
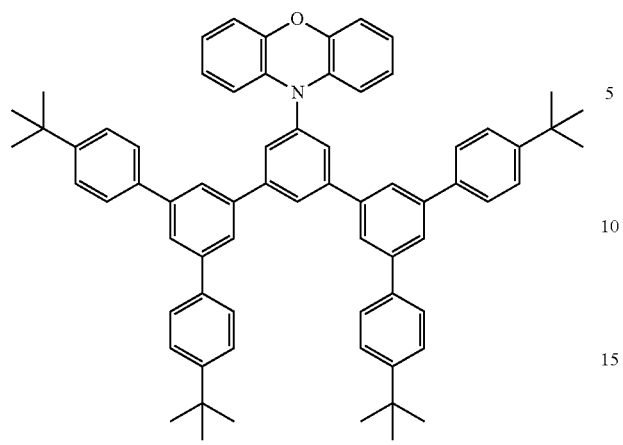
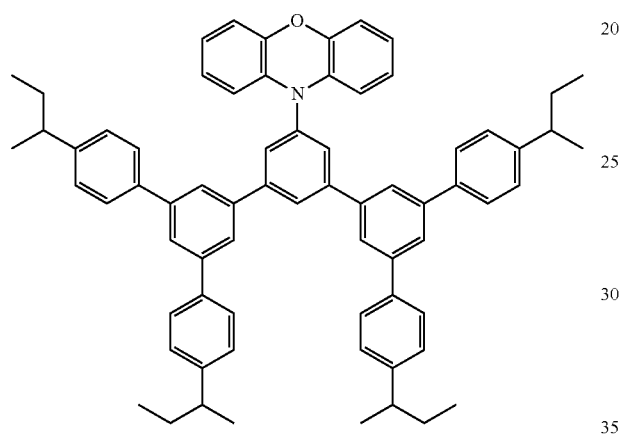
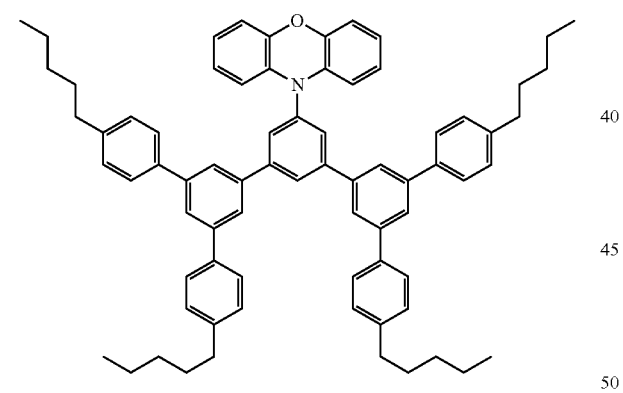
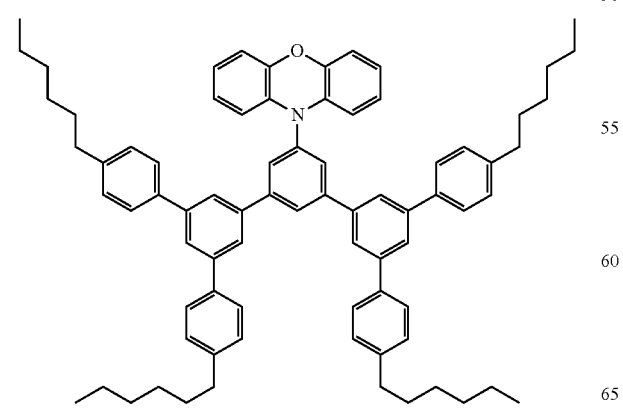
26
-continued
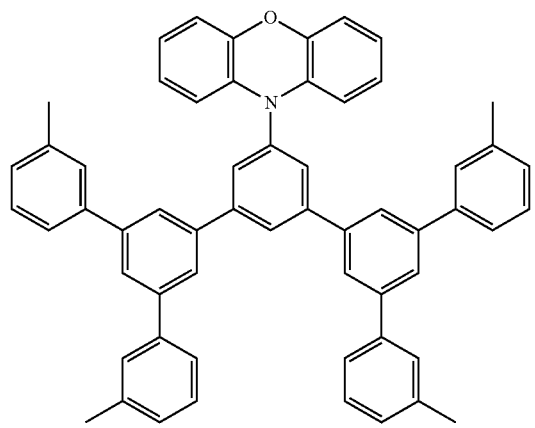
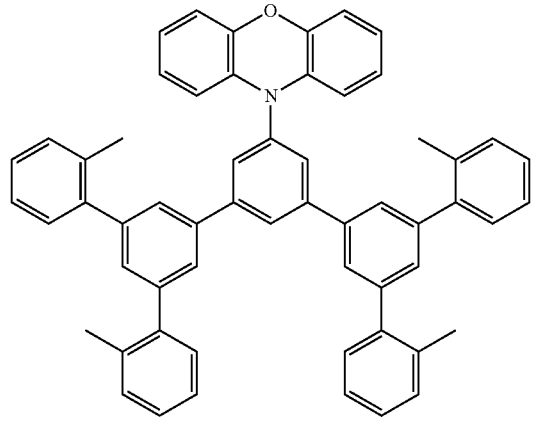
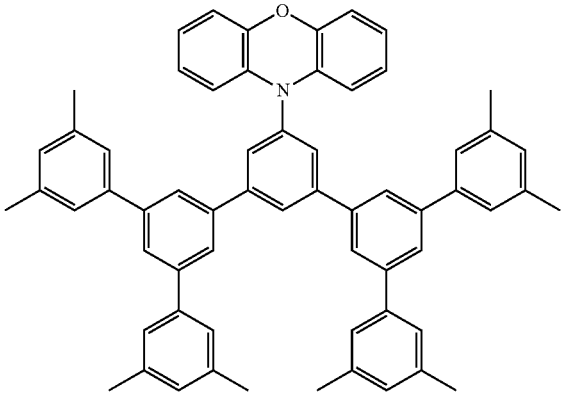
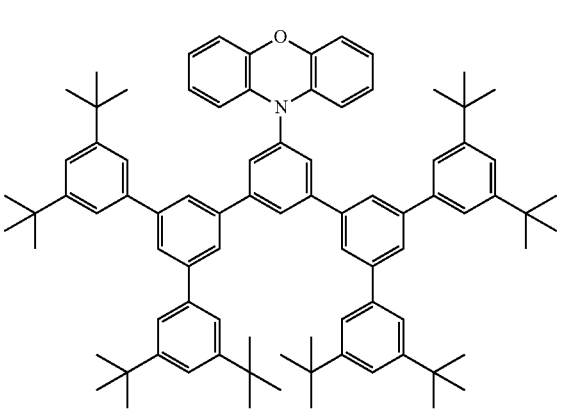

27
-continued
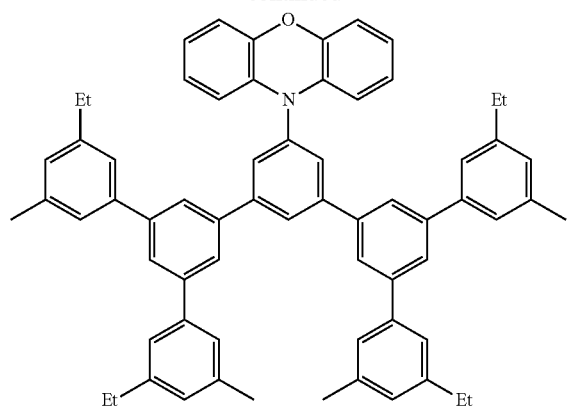
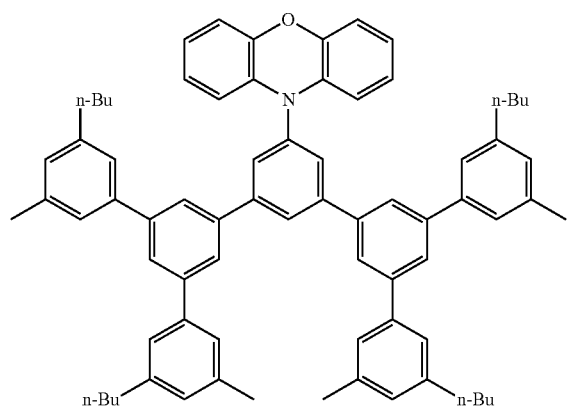
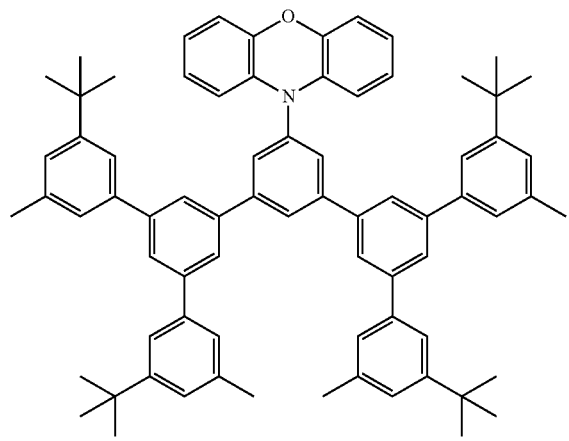
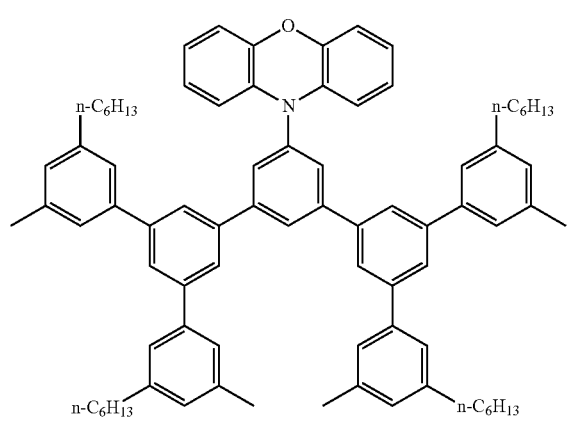
28
-continued
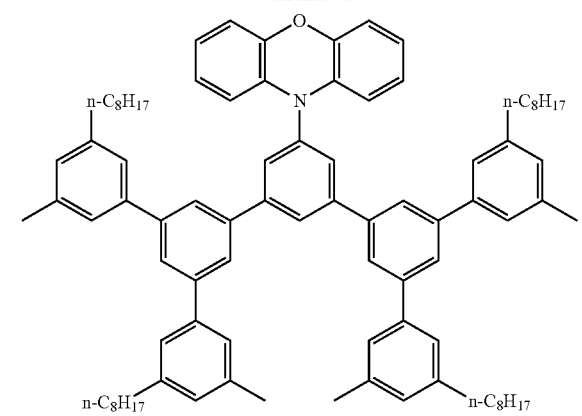
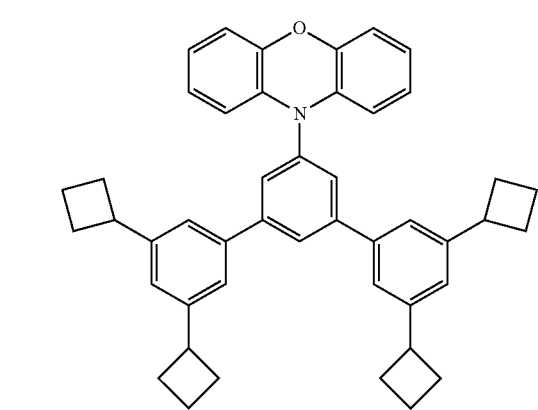
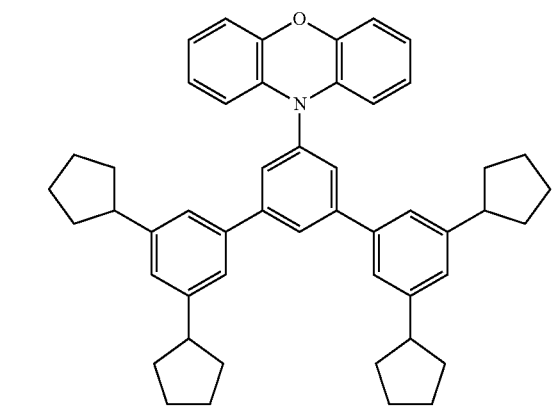
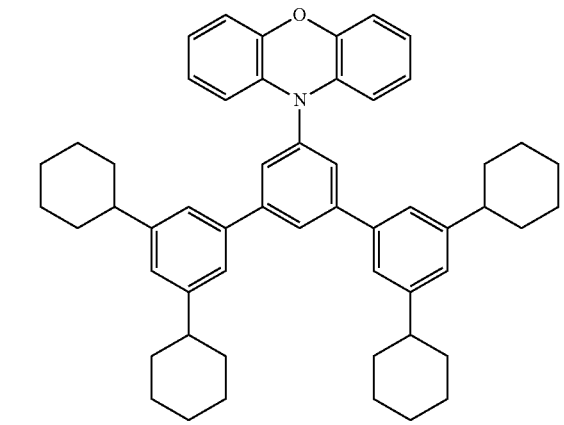

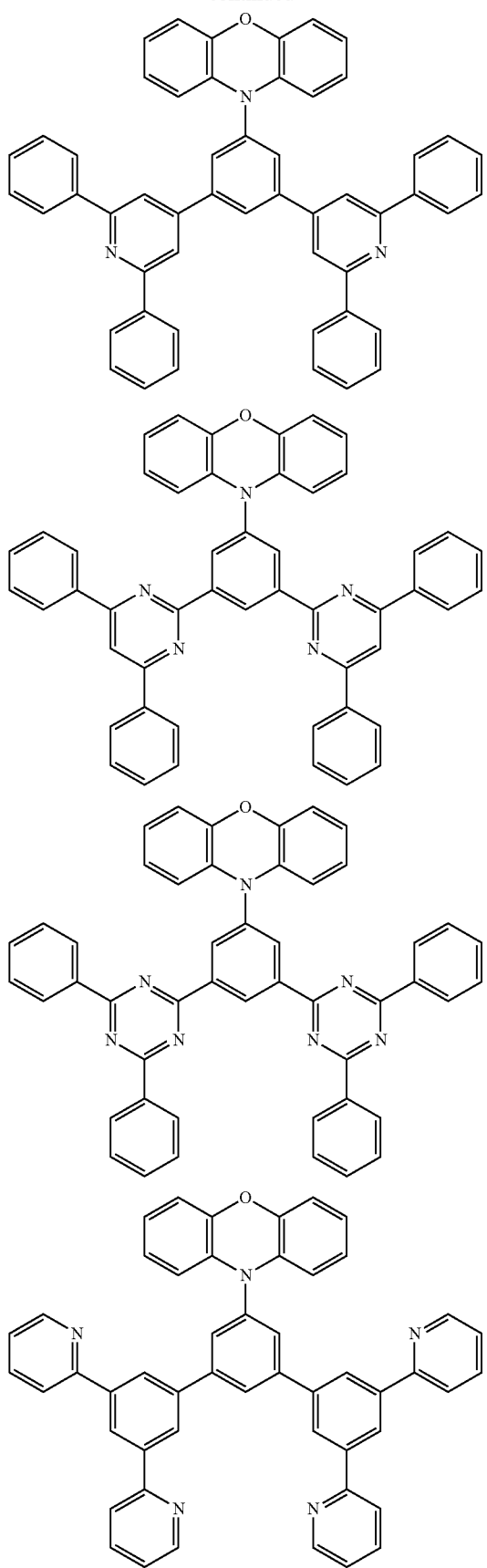
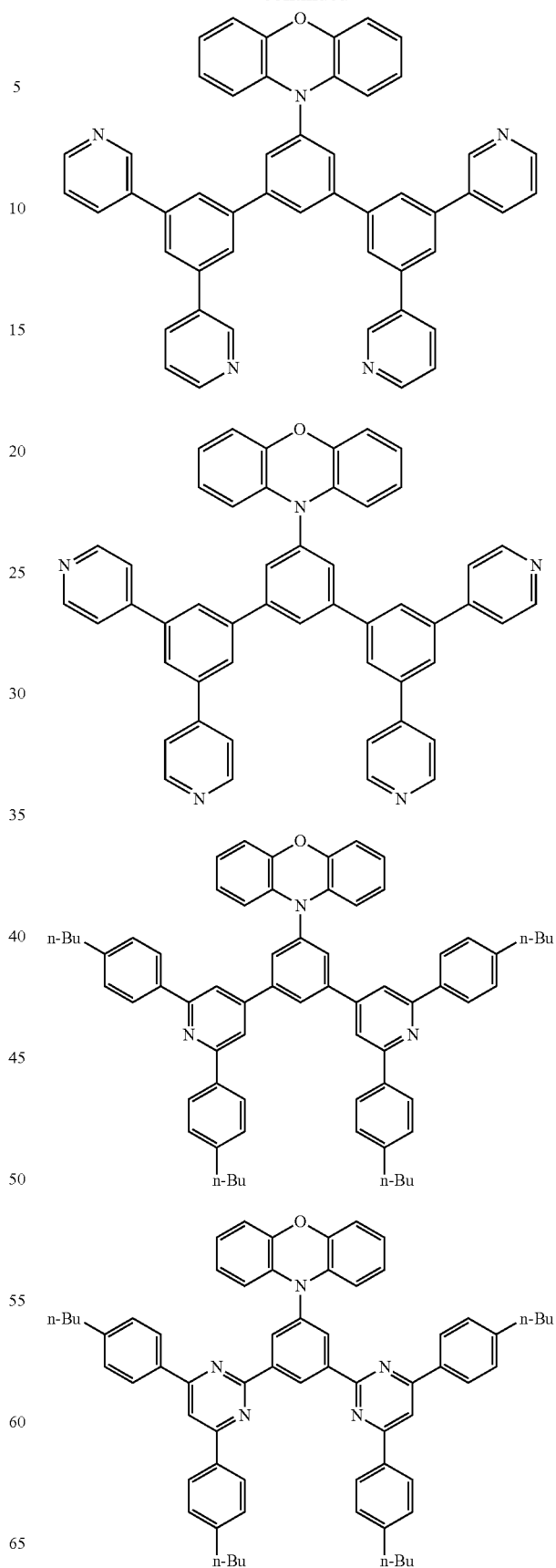

31
-continued
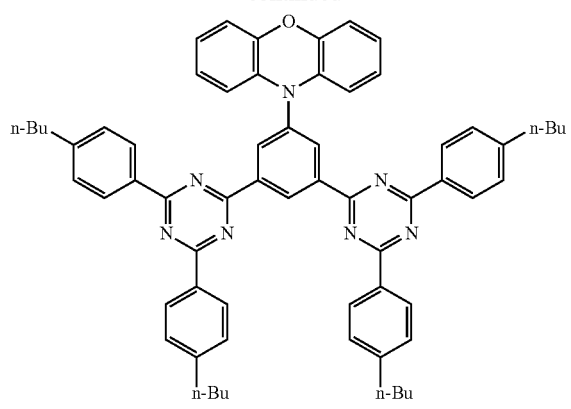
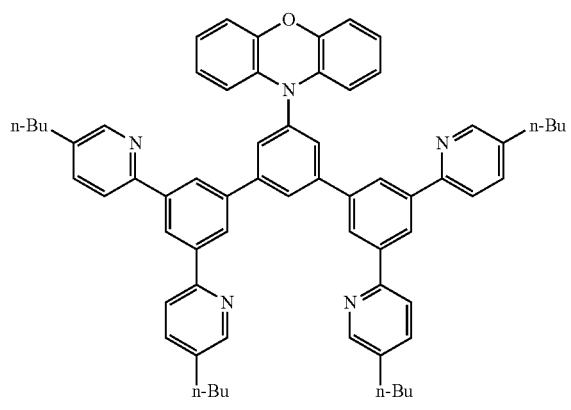
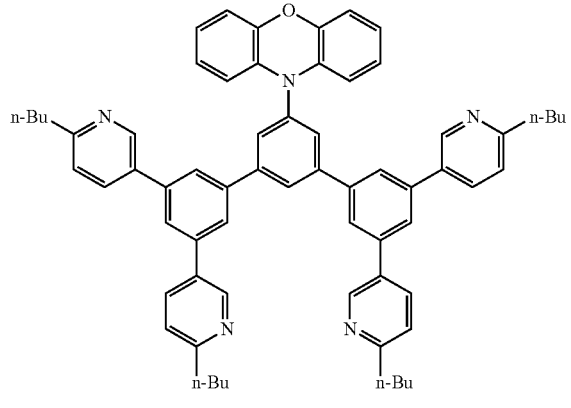
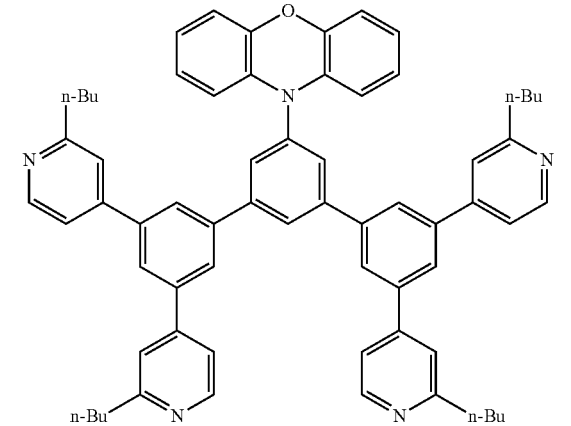
32
-continued
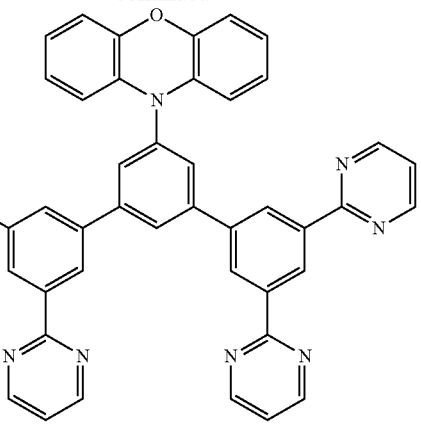
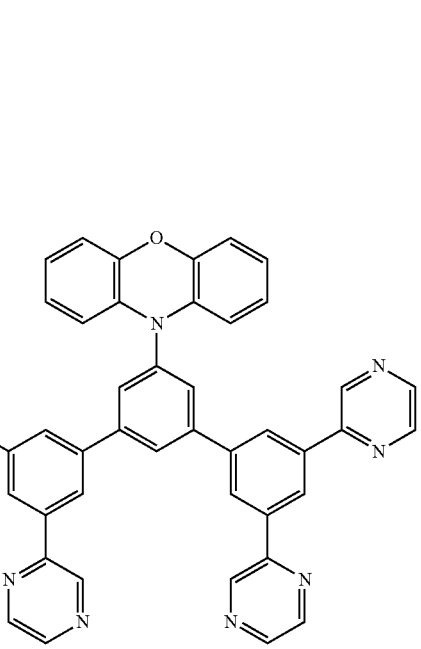
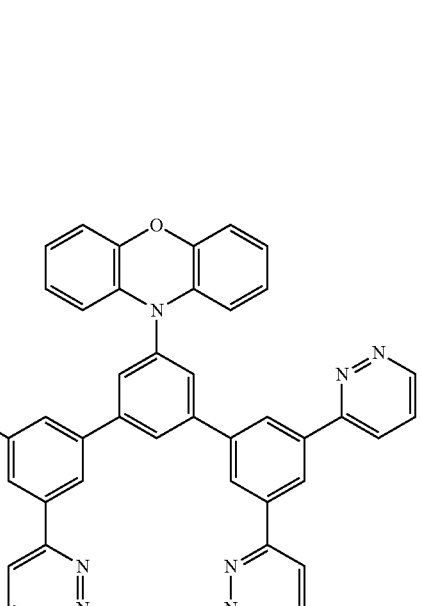

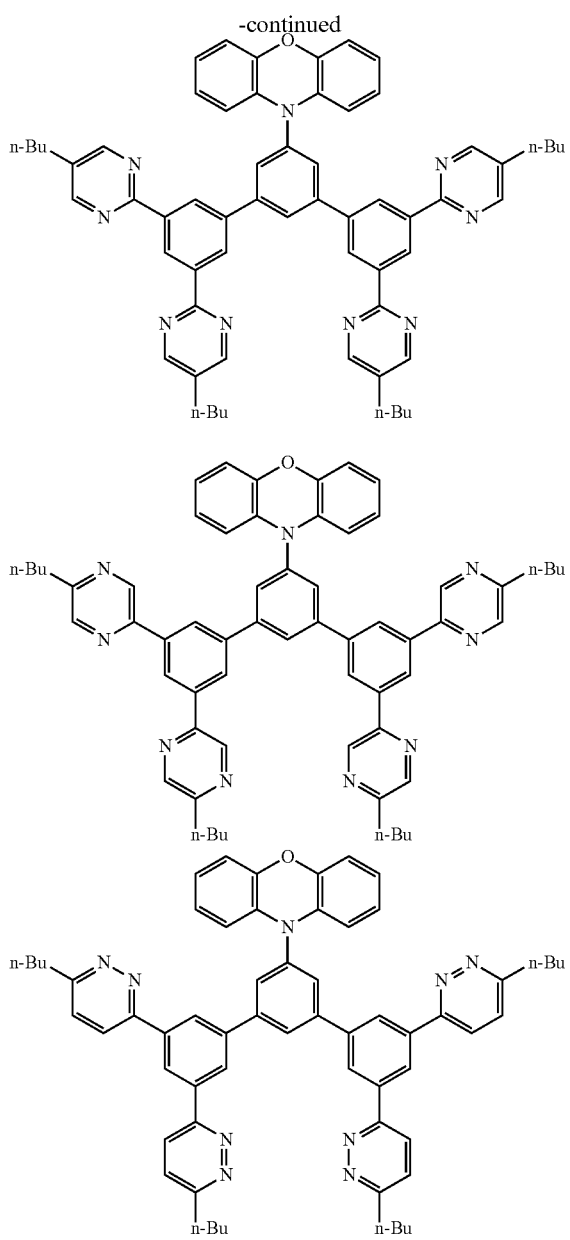

(wherein Me represents a methyl group, Et represents an ethyl group, n-Pr represents a n-propyl group, and n-Bu represents a n-butyl group. The same shall apply hereinafter.)

In the polymer compound of the present invention, the residue of the compound represented by the above-described formula (0), (0-1) or (1) may exist on any position, and may be a mono-valent group or a multi-valent group, and usually is a mono-valent to tri-valent group, preferably a mono-valent or di-valent group.

Among the residues of the compounds represented by the above-described formulae (0), (0-1) and (1), preferable are residues obtained by removing from the compounds a hydrogen atom on a benzene ring contained in them. Particularly, more preferable are residues obtained by removing from the compounds a hydrogen atom on a benzene ring belonging to a phenoxazine ring contained in them.

The residue of the compound represented by the above-described formula (1) is preferably a di-valent group represented by the following formula (0-2), more preferably a di-valent group represented by the following formula (2), further preferably a di-valent group represented by the following formula (2) in which $A^1$ represents —$C(R^2)$= and $R^1$ represents an aryl group, from the standpoint of easiness of synthesis of a polymer compound and device properties. It is particularly preferable that the di-valent group represented by the following formula (2) is contained as a repeating unit in the polymer compound of the present invention.

(0-2)

(wherein $Ar^0$ represents the same meaning as described above.)

(2)

(wherein $A^1$ and $R^1$ represent the same meaning as described above.).

In the polymer compound of the present invention, the residue of the compound represented by the above-described formula (0), (0-1) or (1) and the di-valent group represented by the above-described formula (2) may each be contained singly or in combination of two or more.

It is preferable that the polymer compound of the present invention contains further a repeating unit represented by the following formula (3), from the standpoint of luminance half life when used in a light emitting device.

(wherein $Ar^1$ represents an arylene group or a di-valent heterocyclic group. $R^3$ and $R^4$ each independently represent a hydrogen atom, alkyl groups, an aryl group, a mono-valent heterocyclic group or a cyano group. Groups represented by $Ar^1$, $R^3$ and $R^4$ optionally have a substituent. n is 0 or 1).

The arylene group represented by $Ar^1$ in the above-described formula (3) is usually an arylene group having a carbon atom number of 6 to 60 and examples thereof include phenylene groups (the following formulae 1 to 3), naphthalenediyl groups (the following formulae 4 to 13), anthracenylene groups (the following formulae 14 to 19), biphenylene groups (the following formulae 20 to 25), triphenylene groups (the following formulae 26 to 28) and condensed ring compound groups (the following formulae 29 to 56). In these formulae, R represents a hydrogen atom, an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a substituted amino group, a silyl group, a substituted silyl group, a halogen atom, an acyl group, an acyloxy group, an amide group, a mono-valent heterocyclic group, a heterocyclic oxy group, a carboxyl group, a substituted carboxyl group, a nitro group or a cyano group. The carbon atom number of the arylene group does not include the carbon atom number of R. The groups and atoms represented by R are the same as those explained and exemplified as the groups and atoms represented by $R^2$. A solid line appended with no R represents a bond.

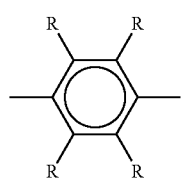

1

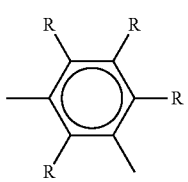

2

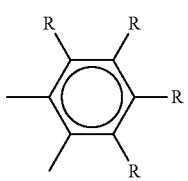

3

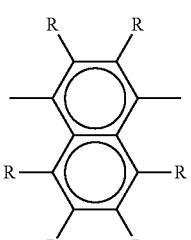

4

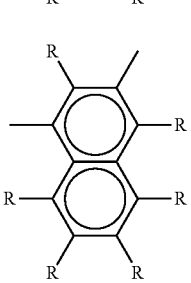

5

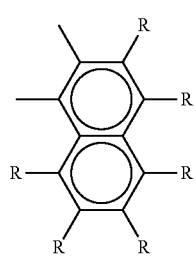

6

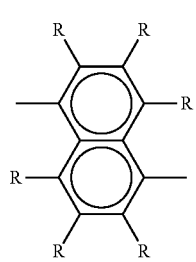

7

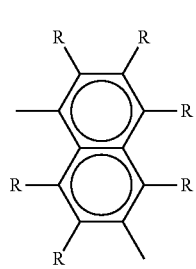

8

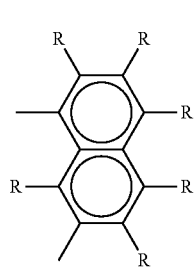

9

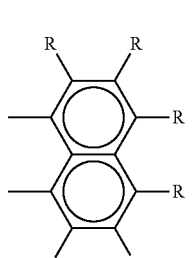

10

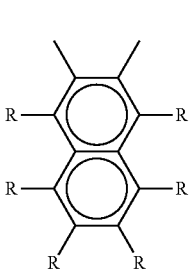

11

12
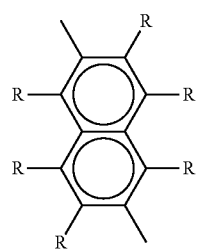
13
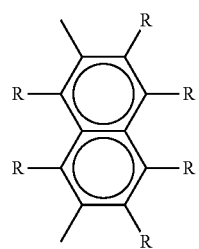
14
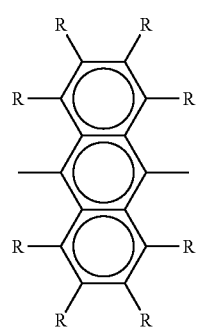
15
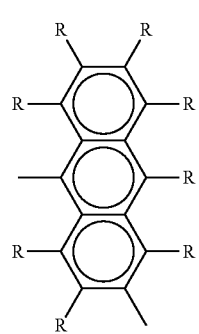
16
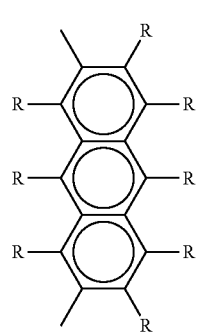
17
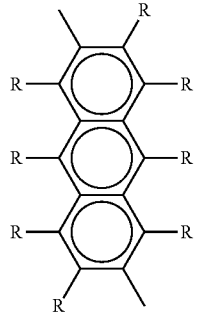
18
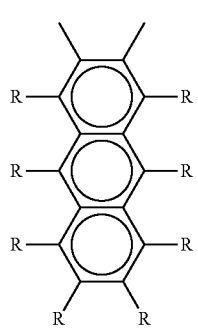
19
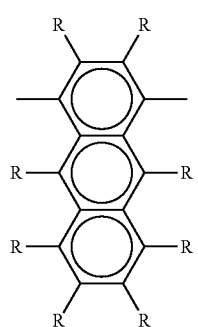
20
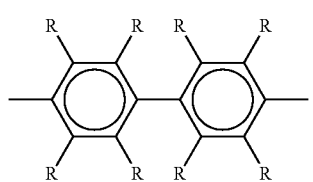
21
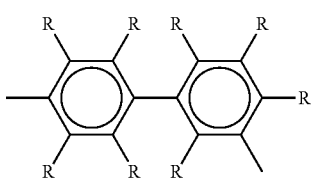
22
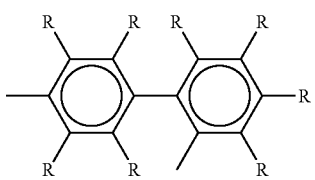

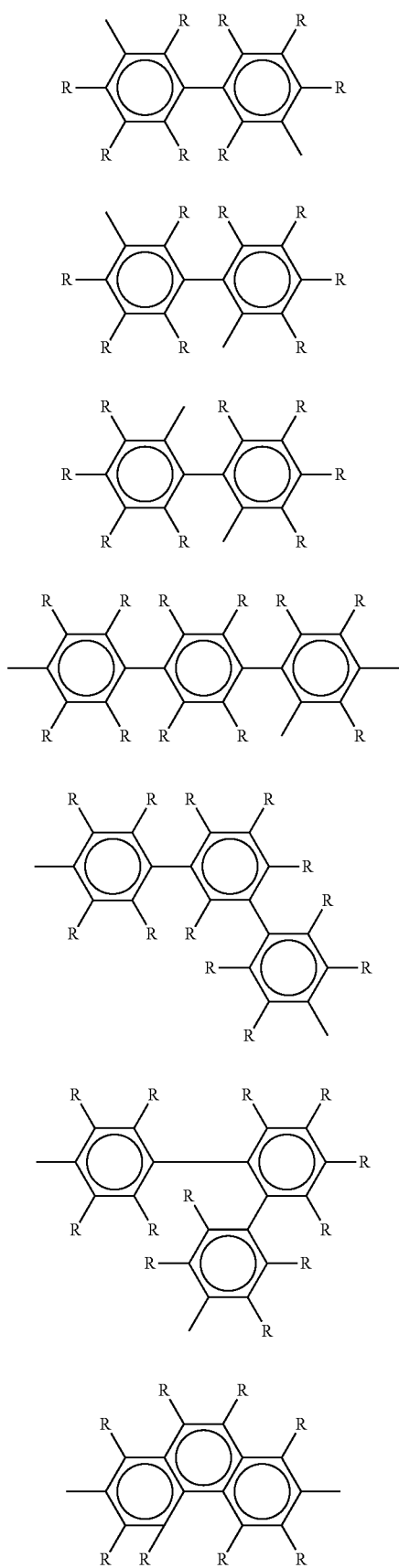
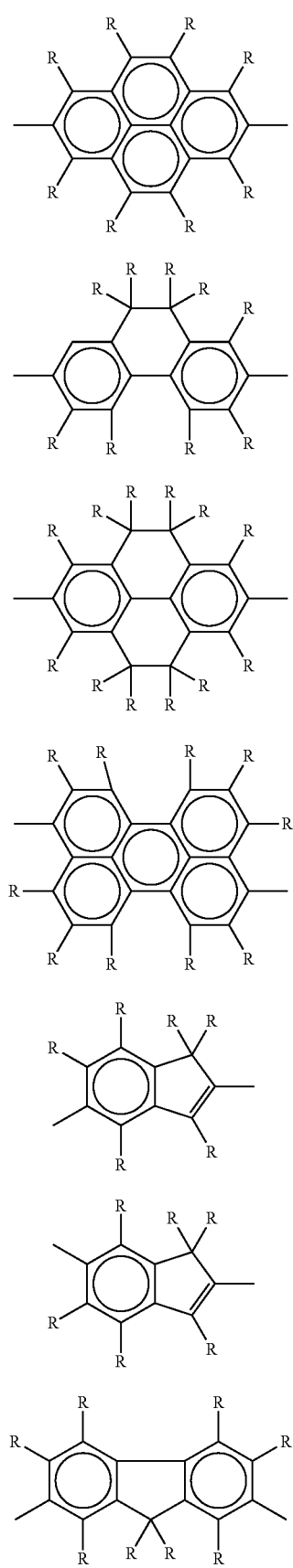

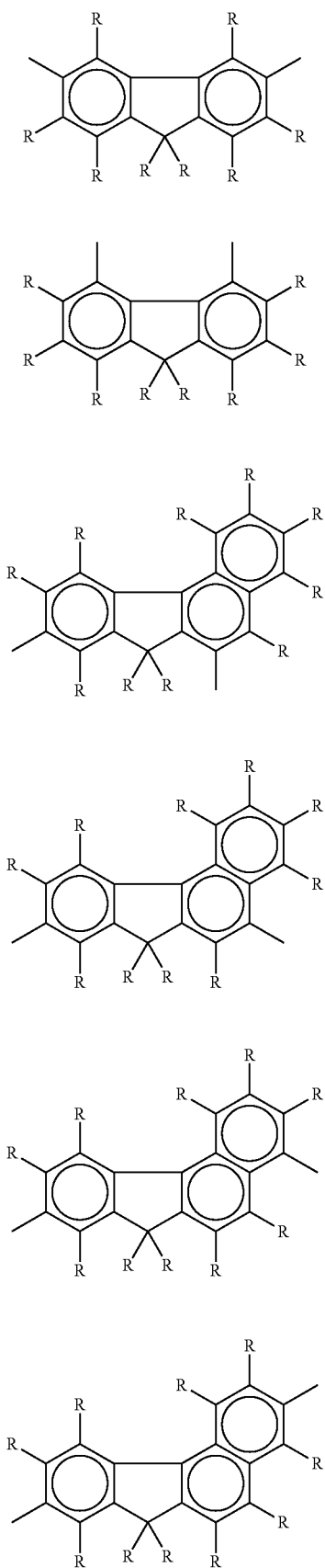
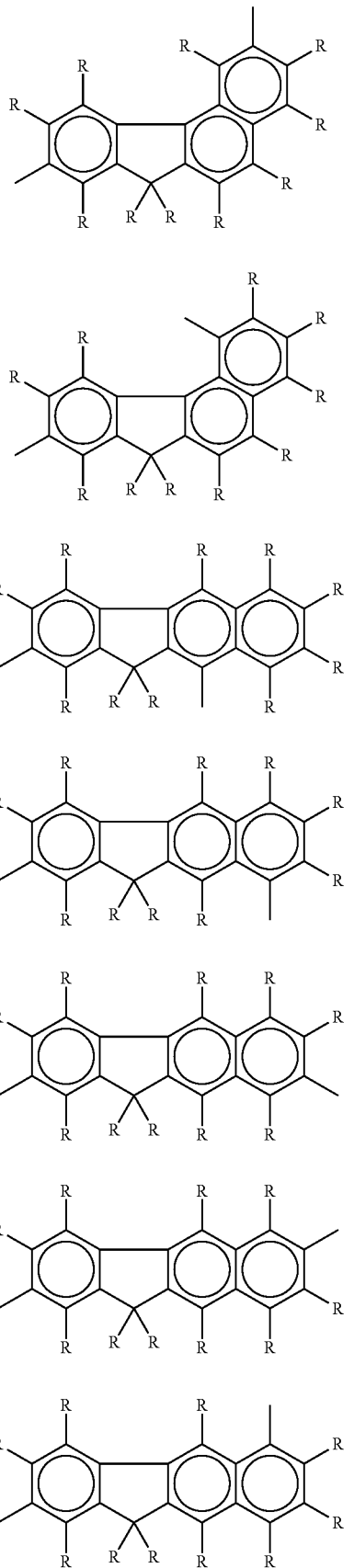

50

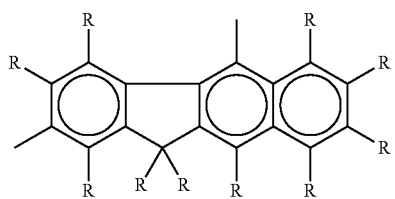

51

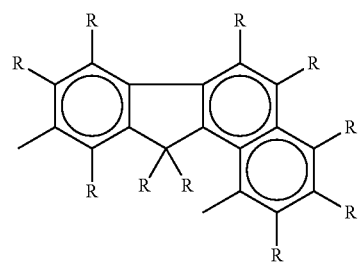

52

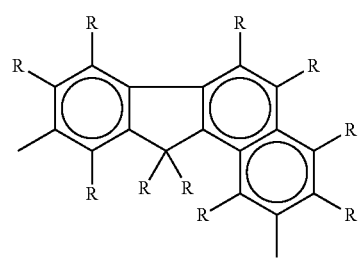

53

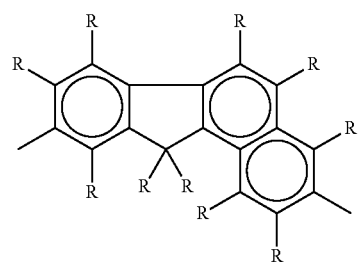

54

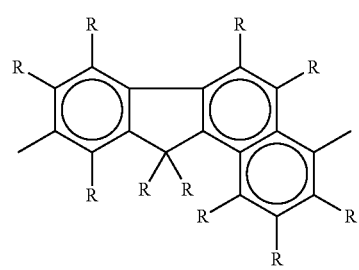

55

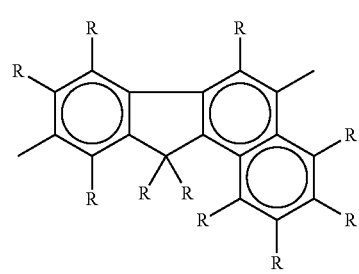

56

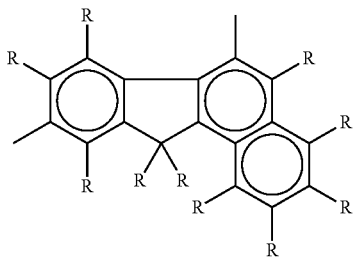

The di-valent heterocyclic group represented by Ar$^1$ in the above-described formula (3) means an atomic group remaining after removing two hydrogen atoms from a heterocyclic compound. As the di-valent heterocyclic group, di-valent aromatic heterocyclic groups are preferable. The di-valent heterocyclic group has a carbon atom number of usually 2 to 60 and examples thereof include those represented by the following formulae. The carbon atom number of the di-valent heterocyclic group does not include the carbon atom number of R.

Di-valent heterocyclic groups containing nitrogen as a hetero atom: pyridinediyl groups (the following formulae 57 to 62), diazaphenylene groups (the following formulae 63 to 66), quinolinediyl groups (the following formulae 67 to 81), quinoxalinediyl groups (the following formulae 82 to 86), phenoxazinediyl group (the following formula 87), phenothiazinediyl group (the following formula 88), acridinediyl groups (the following formulae 89 to 90), bipyridyldiyl groups (the following formulae 91 to 93), phenanthrolinediyl groups (the following formulae 94 to 96) and the like;

Groups containing silicon, nitrogen, sulfur, selenium and the like as a hetero atom and having a cross-linked biphenyl structure (the following formulae 97 to 126);

5-membered ring heterocyclic groups containing silicon, nitrogen, sulfur, selenium and the like as a hetero atom (the following formulae 127 to 132);

5-membered ring condensed heterocyclic groups containing silicon, nitrogen, sulfur, selenium and the like as a hetero atom (the following formulae 133 to 142), a benzothiadiazole-4,7-diyl group, a benzooxadiazole-4,7-diyl group and the like;

5-membered ring heterocyclic groups containing silicon, nitrogen, sulfur, selenium and the like as a hetero atom and connected at an α-position of the hetero atom to form a dimer or an oligomer (the following formulae 143, 144);

5-membered ring heterocyclic groups containing silicon, nitrogen, sulfur, selenium and the like as a hetero atom and connected at an α-position of the hetero atom to a phenyl group (the following formulae 145 to 151);

Tri-cyclic groups obtained by connection of a heterocyclic group containing nitrogen, oxygen, sulfur and the like as a hetero atom with a benzene ring or a mono-cyclic heterocyclic group (the following formulae 152 to 157).

57

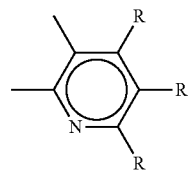

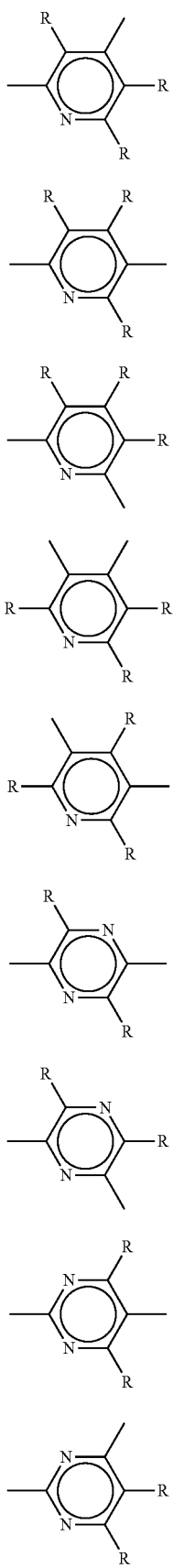
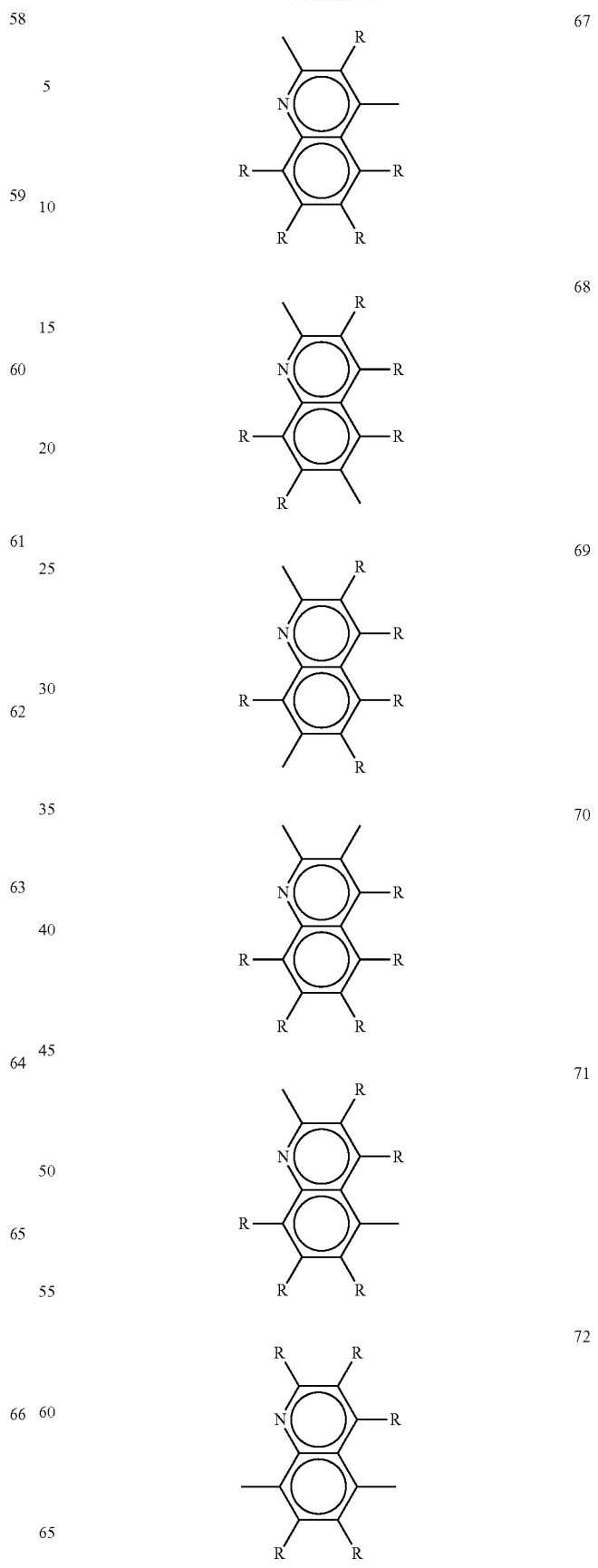

73 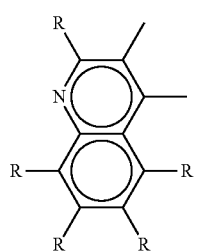
74 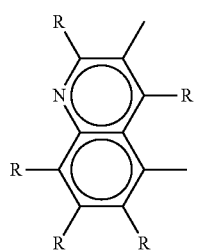
75 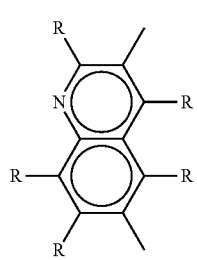
76 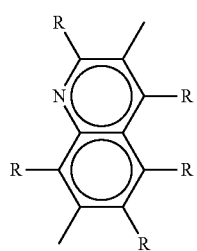
77 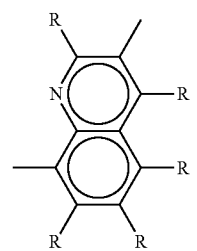
78 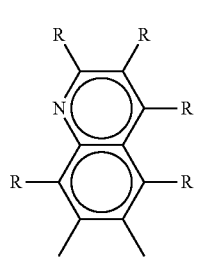
79 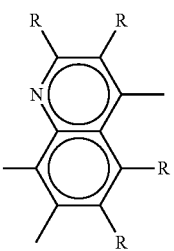
80 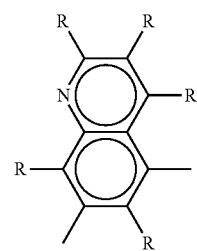
81 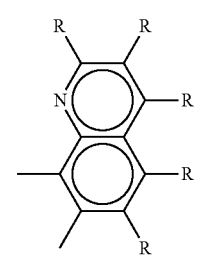
82 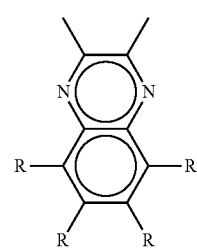
83 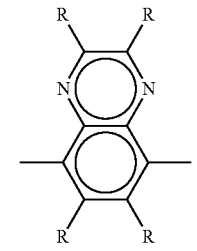
84 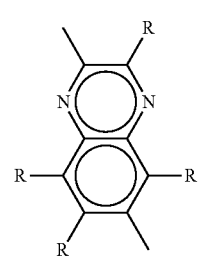

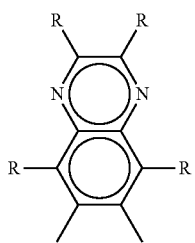
85
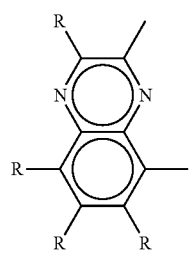
86
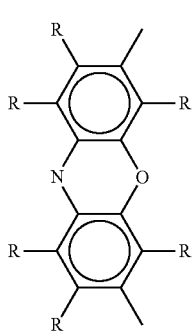
87
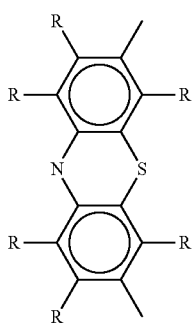
88
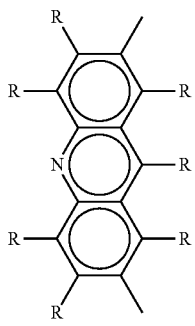
89
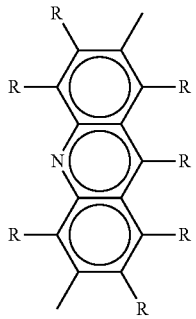
90
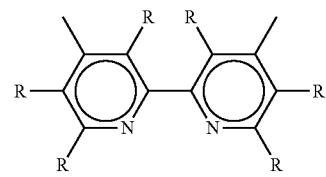
91
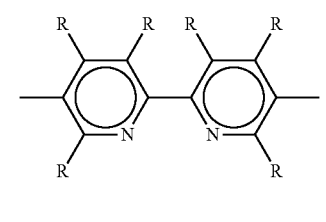
92
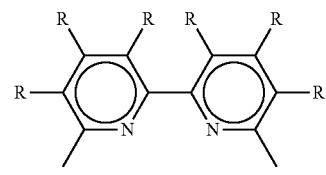
93
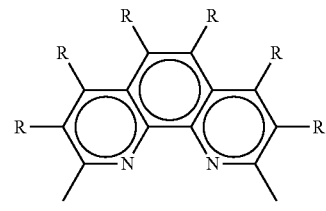
94
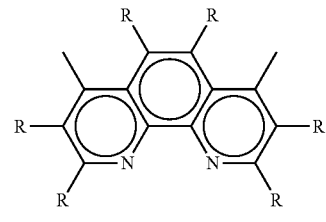
95
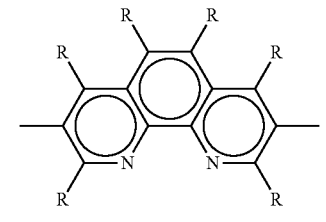
96

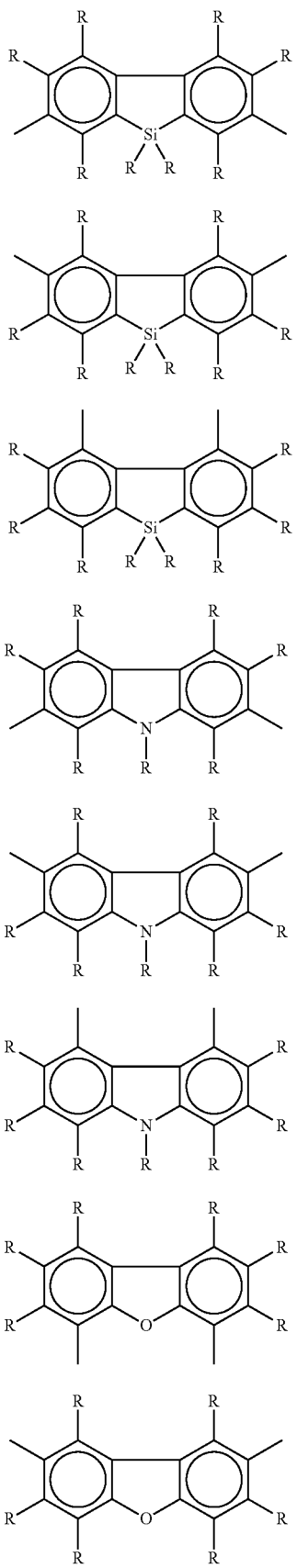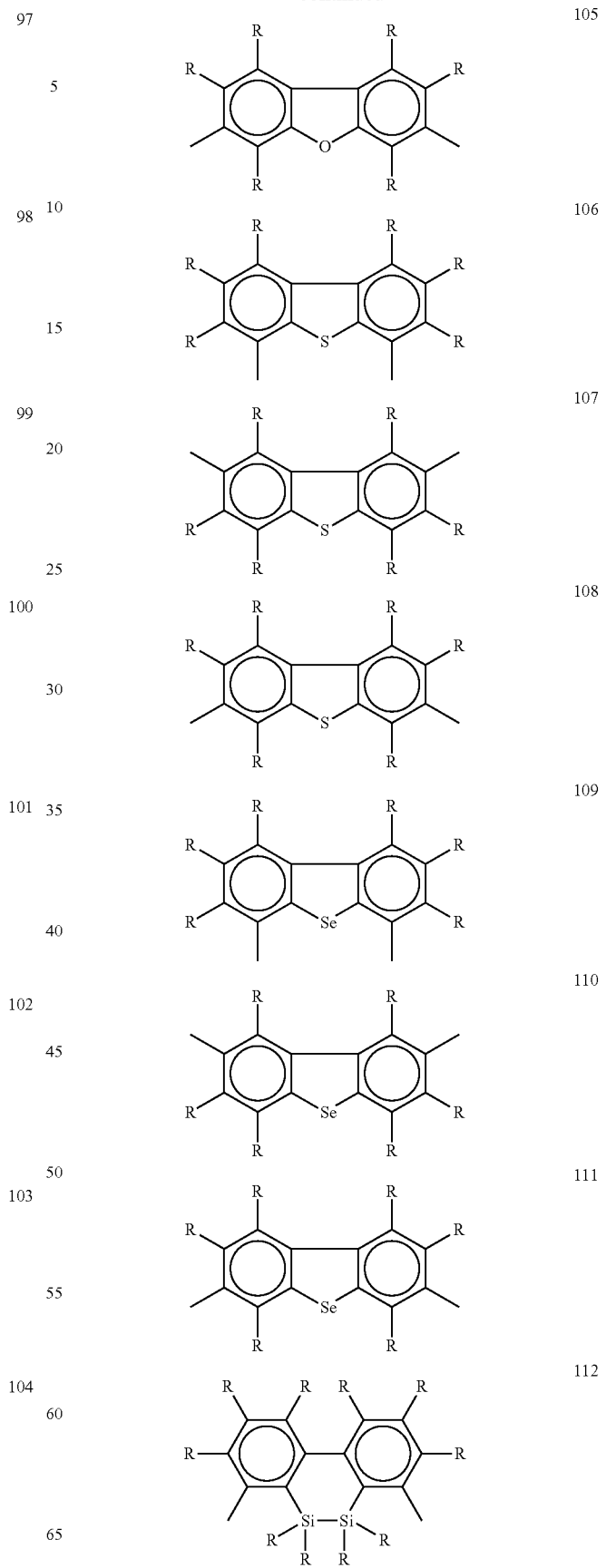

113 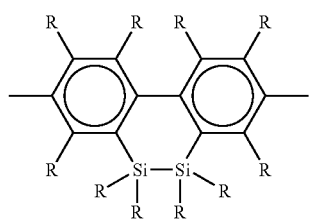
114 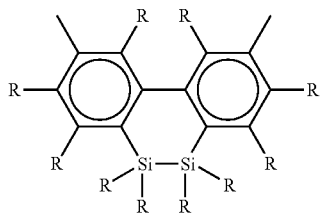
115 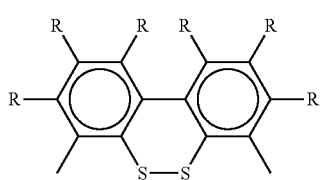
116 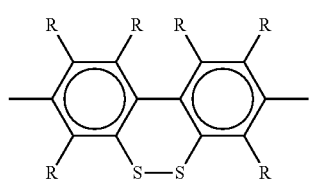
117 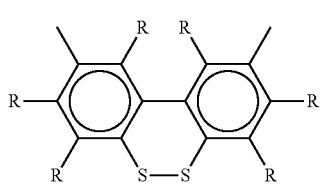
118 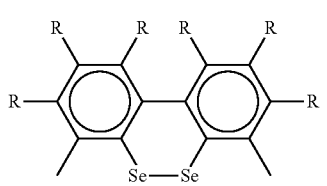
119 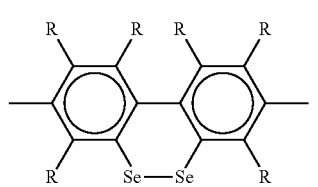
120 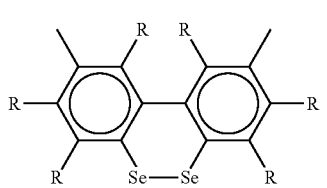
121 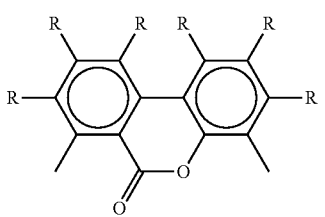
122 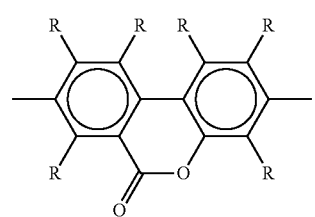
123 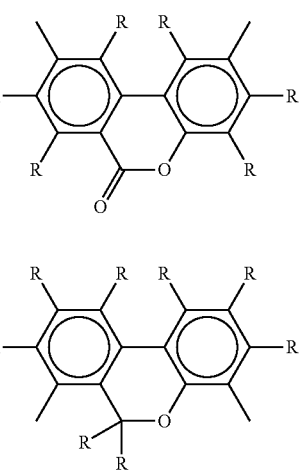
124
125 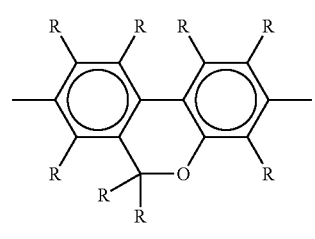
126 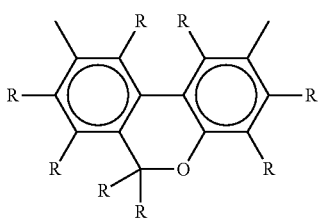
127 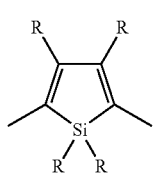

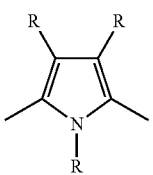 128
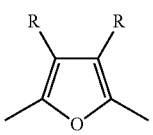 129
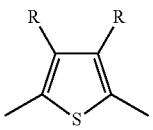 130
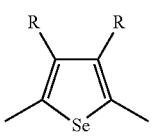 131
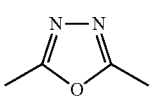 132
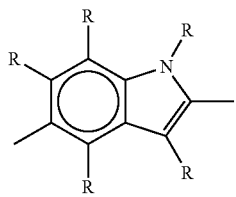 133
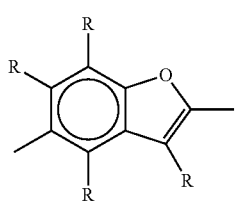 134
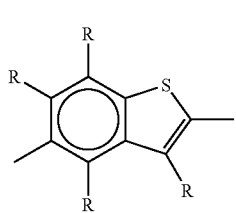 135
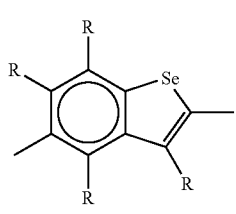 136
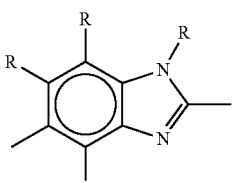 137
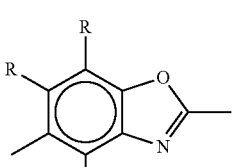 138
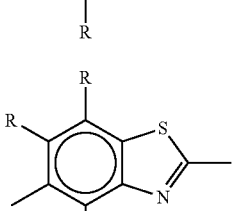 139
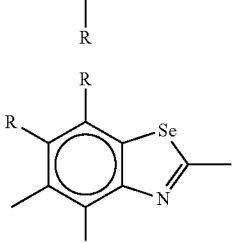 140
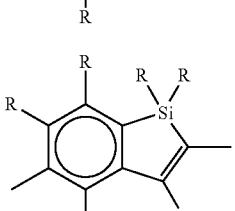 141
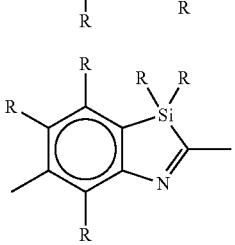 142
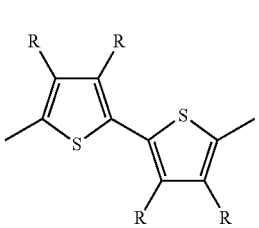 143
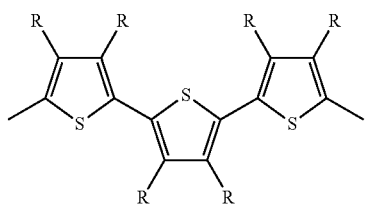 144

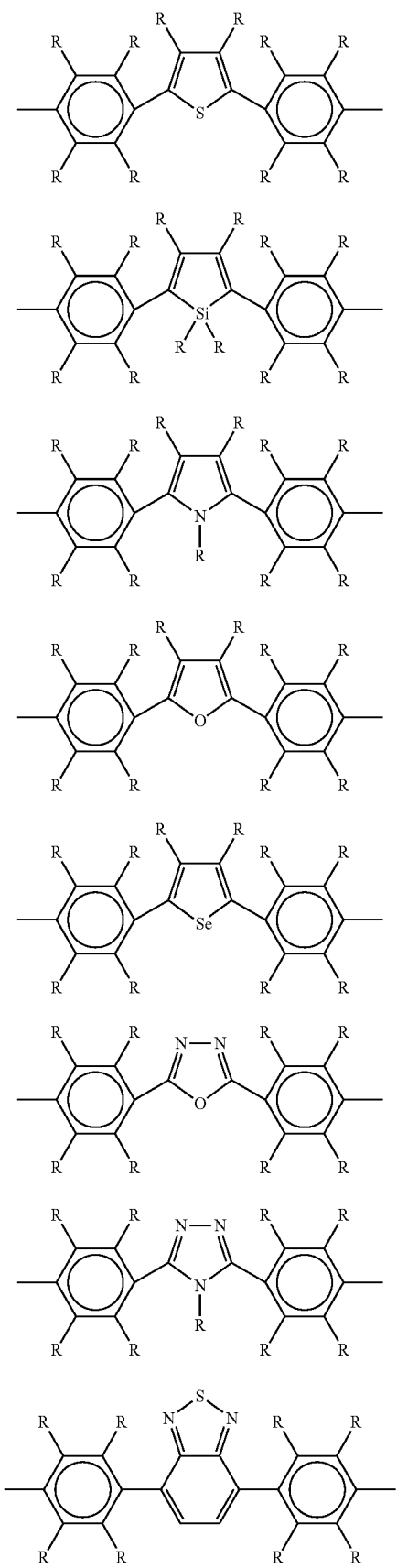
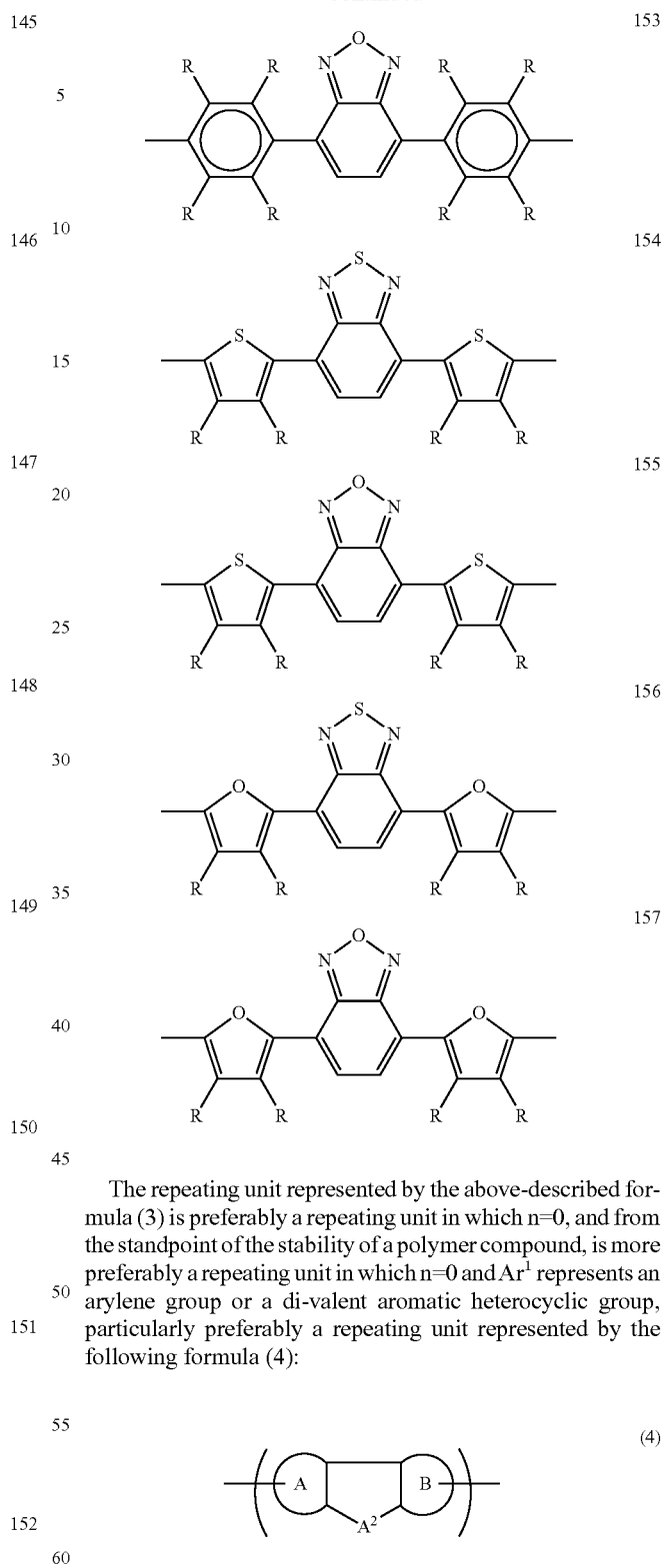

The repeating unit represented by the above-described formula (3) is preferably a repeating unit in which n=0, and from the standpoint of the stability of a polymer compound, is more preferably a repeating unit in which n=0 and $Ar^1$ represents an arylene group or a di-valent aromatic heterocyclic group, particularly preferably a repeating unit represented by the following formula (4):

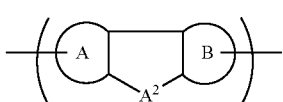

(wherein a ring A and a ring B each independently represent an aromatic hydrocarbon ring or an aromatic heterocyclic ring, and each of the ring A and the ring B has one bond thereon, $A^2$ represents a di-valent group which is connected to the ring A and to the ring B to form a 5-membered or 6-membered ring.).

The repeating unit represented by the above-described formula (4) includes repeating units composed of di-valent groups represented by the above-described formulae 29, 31, 36 to 56, 94 to 126.

As the repeating unit represented by the above-described formula (4), groups represented by the following formula (5) are preferable.

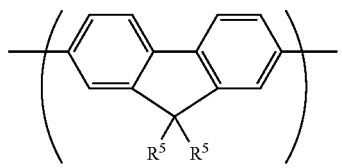

(wherein $R^5$ represents a hydrogen atom, an alkyl group, an aryl group, an arylalkyl group or a mono-valent heterocyclic group, or two $R^5$s may be mutually connected to form a ring. A group represented by $R^5$ optionally has a substituent. Two $R^5$s may be the same or different.).

The alkyl groups, aryl group, arylalkyl group and mono-valent heterocyclic group represented by $R^5$ in the above-described formula (5) are the same as those explained and exemplified as the group represented by $Ar^0$.

The repeating unit represented by the above-described formula (5) is preferably a repeating unit in which $R^5$ represents an alkyl group, an aryl group or an arylalkyl group, and from the standpoint of the solubility of a polymer compound in a solvent, preferably a repeating unit in which $R^5$ has an alkyl group having a carbon atom number of 4 or more, from the standpoint of device properties when used in a light emitting device.

The repeating unit represented by the above-described formula (5) includes repeating units represented by the following formulae.

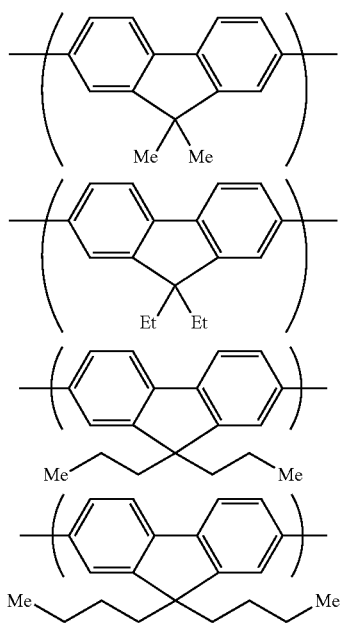

-continued

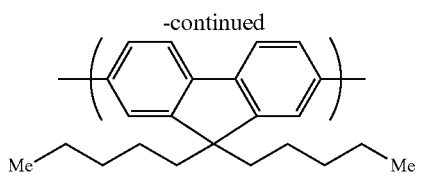

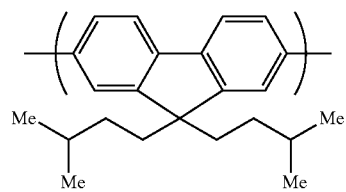

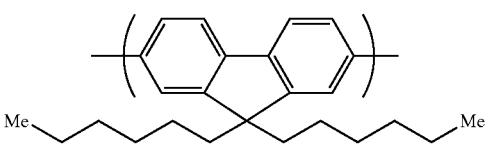

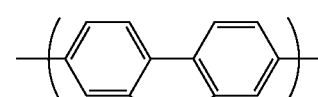

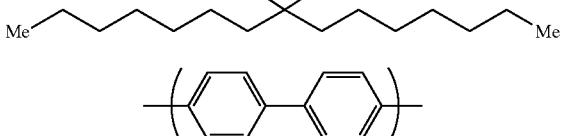

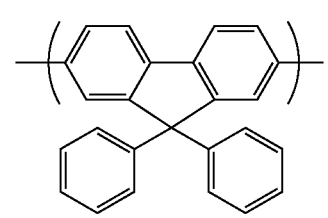

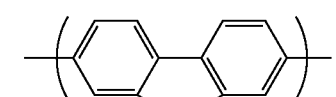

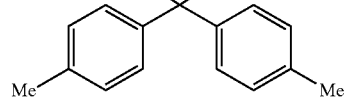

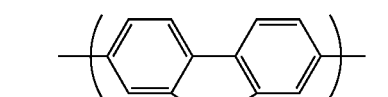

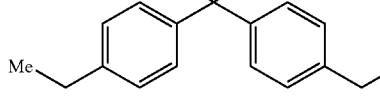

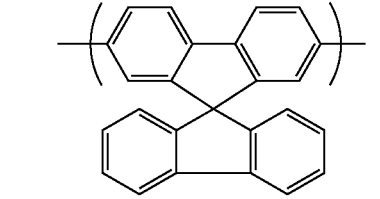

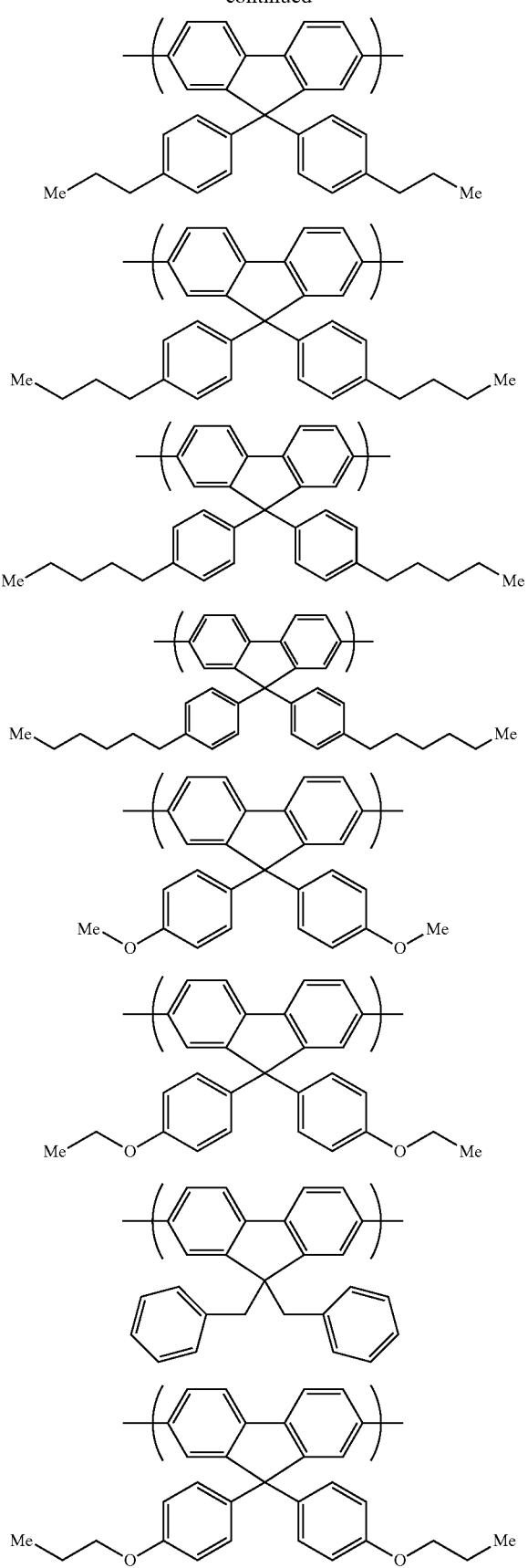

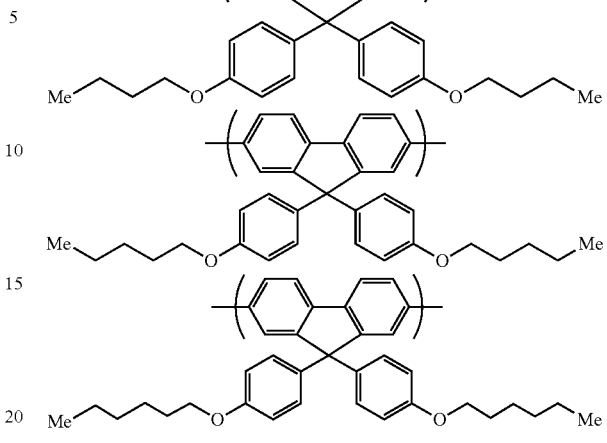

In the polymer compound of the present invention, the repeating units represented by the above-described formulae (3), (4) and (5) may each be contained singly or in combination of two or more.

The polymer compound of the present invention preferably contains a repeating unit represented by the following formula (6), and more preferably contains a repeating unit represented by the following formula (6) in addition to the repeating unit represented by the above-described formula (3), from the standpoint of device properties.

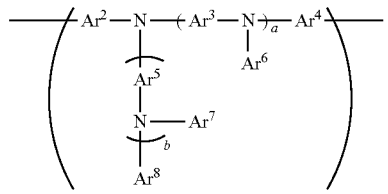

(6)

(wherein $Ar^2$, $Ar^3$, $Ar^4$ and $Ar^5$ each independently represent an arylene group or a di-valent heterocyclic group. $Ar^6$, $Ar^7$ and $Ar^8$ each independently represent an aryl group or a mono-valent heterocyclic group. Groups represented by $Ar^2$, $Ar^3$, $Ar^4$, $Ar^5$, $Ar^6$, $Ar^7$ and $Ar^8$ optionally have a substituent. a and b each independently represent an integer of 0 or more. When a is 2 or more, a plurality of $Ar^3$s and a plurality of $Ar^6$s may be the same or different, respectively. When b is 2 or more, a plurality of $Ar^5$s and a plurality of $Ar^7$s may be the same or different, respectively.).

The polymer compound containing a repeating unit represented by the above-described formula (6) is preferably used as a light emitting layer, a hole transporting layer or a hale injection layer of a light emitting device, from the standpoint of chromatic purity and luminance half life.

In the above-described formula (6), the arylene group and di-valent heterocyclic group represented by $Ar^2$, $Ar^3$, $Ar^4$ and $Ar^5$ are the same as those explained and exemplified as the arylene group and di-valent heterocyclic group represented by $Ar^1$.

In the above-described formula (6), $Ar^2$, $Ar^3$, $Ar^4$ and $Ar^5$ represent preferably an arylene group optionally having a substituent, more preferably a phenylene group optionally having a substituent, a biphenylene group optionally having a substituent or a naphthylene group optionally having a substituent.

The aryl group and mono-valent heterocyclic group represented by $Ar^6$, $Ar^7$ and $Ar^8$ are the same as those explained and exemplified as the aryl group and mono-valent heterocyclic group represented by $R^2$.

$Ar^6$, $Ar^7$ and $Ar^8$ represent preferably an aryl group having an alkyl group having a carbon atom number of 4 or more as a substituent, from the standpoint of the solubility of a polymer compound in a solvent and device properties.

The repeating unit represented by the above-described formula (6) is preferably a repeating unit in which $Ar^2$, $Ar^3$, $Ar^4$ and $Ar^5$ represent an arylene group and $Ar^6$, $Ar^7$ and represent an aryl group, from the standpoint of the stability of a polymer compound.

The repeating unit represented by the above-described formula (6) includes alto repeating units represented by the following formulae 158 to 165.

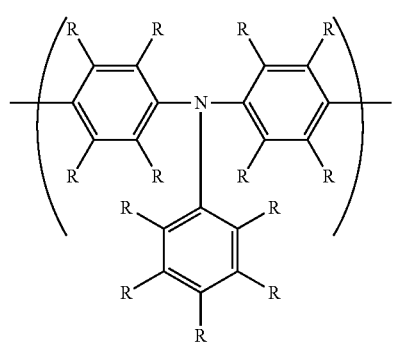

158

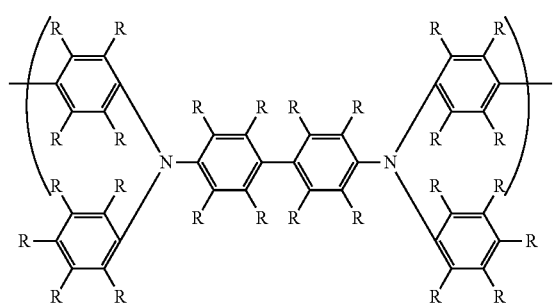

159

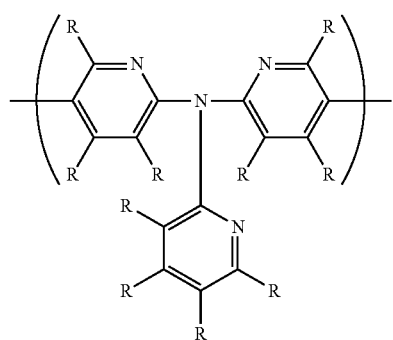

160

-continued

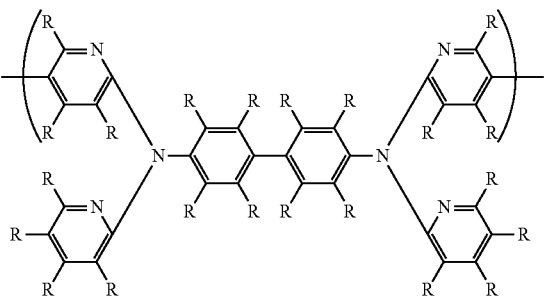

161

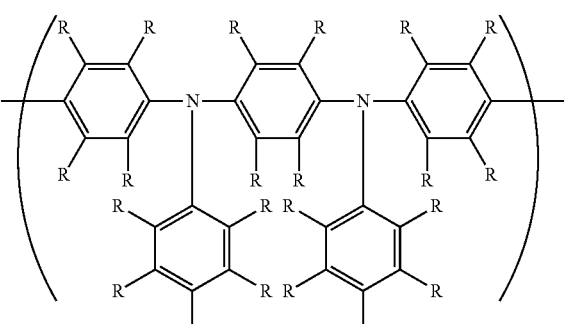

162

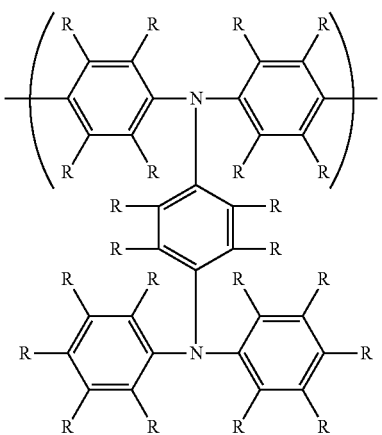

163

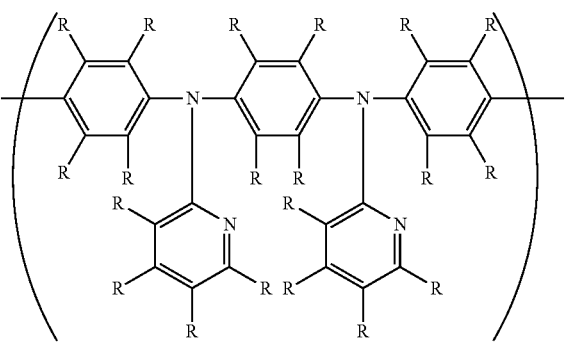

164

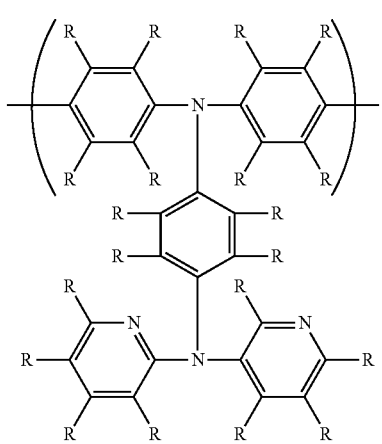

(wherein R represents the same meaning as described above.).

In the polymer compound of the present invention, the repeating units represented by the above-described formula (6) may be contained singly or two or more of them may be contained, and it is preferable that one or two of them are contained.

In the polymer compound of the present invention, the substituent represents preferably an alkyl group, an alkoxy group, an aryl group, an aryloxy group, an arylalkyl group, an arylalkoxy group, a halogen atom, an acyl group, an acyloxy group, a mono-valent heterocyclic group, a heterocyclic oxy group or a substituted carboxyl group, more preferably an alkyl group, an aryl group or an arylalkyl group, from the standpoint of chromatic purity as a blue material. It is preferable that the light emission energy of these substituents is larger than the light emission energy derived from a residue of a compound represented by the above-described formula (0).

The polymer compound of the present invention is preferably a conjugated polymer from the standpoint of charge transportability when fabricated into a film and device properties when used in a light emitting layer. Here, the conjugated polymer means a polymer in which a delocalized π electron pair is present along the main chain skeleton of the polymer compound, and includes a case in which an unpaired electron or lone electron pair gets engaged with resonance in addition to a double bond.

In the polymer compound of the present invention, repeating units may be connected via a non-conjugated unit, or the non-conjugated unit may be contained in repeating units, in a range not deteriorating desired properties. The non-conjugated unit includes units shown below, or a combination of two or more of these units, and the like. In the formulae, Ar represents an aromatic hydrocarbon ring or a heterocyclic ring.

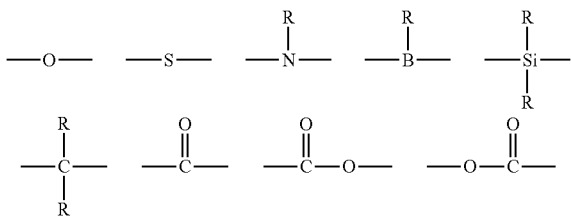

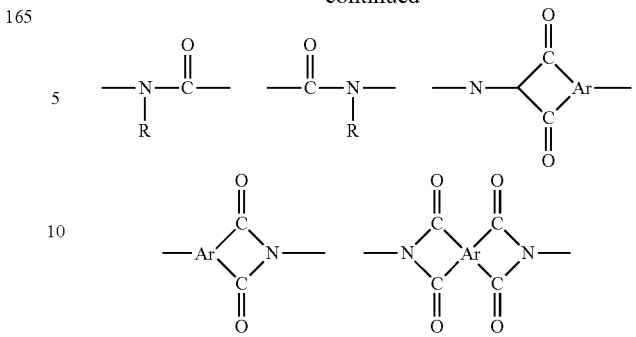

The polymer compound of the present invention may be a random, block, alternate or graft copolymer, or a polymer having an intermediate structure between them, for example, a random copolymer having a block property, further, may also be a polymer having branching in the main chain and thus having three or more end parts, a dendrimer, or an oligomer having a polystyrene-equivalent number average molecular weight of $1 \times 10^4$ or less.

When the polymer compound of the present invention contains a residue of a compound represented by the above-described formula (0) as a repeating unit, the polymer compound of the present invention contains this repeating unit in an amount of preferably 0.1 to 50 mol %, more preferably 0.5 to 20 mol % based on all repeating units, from the standpoint of device properties when this is used as a material of a light emitting layer of a light emitting layer.

When a repeating unit represented by the above-described formula (3) is contained, its proportion is preferably 1 to 99 mol %, more preferably 50 to 97 mol % based on all repeating units, from the standpoint of device properties when the polymer compound of the present invention is used as a material of a light emitting layer of a light emitting device.

When a repeating unit represented by the above-described formula (6) is contained, its proportion is preferably 0.01 to 50 mol %, more preferably 0.1 to 30 mol % based on all repeating units, from the standpoint of device properties when the polymer compound of the present invention is used as a material of a light emitting layer of a light emitting device and from the standpoint of light emission color adjustment.

The polymer compound of the present invention has a polystyrene-equivalent number average molecular weight of preferably $2 \times 10^3$ to $1 \times 10^8$, more preferably $1 \times 10^4$ to $1 \times 10^6$, from the standpoint of luminance half life when fabricated into a light emitting device.

The polymer compound of the present invention is preferably a polymer compound having a reside of a compound represented by the above-described formula (0) and having at least one repeating unit selected from the group consisting of a repeating unit represented by the above-described formula (4) and a repeating unit represented by the above-described formula (6), from the standpoint of chromatic purity as a blue light emitting material. Especially, the sum of the reside of a compound represented by the above-described formula (0) and the at least one repeating unit selected from the group consisting of a repeating unit represented by the above-described formula (4) and a repeating unit represented by the above-described formula (6) is more preferably 95 mol % or more, particularly preferably 99 mol % or more based on all repeating units in the polymer compound.

<Compound>

As the raw material for production of a polymer compound comprising a residue of a compound represented by the above-described formula (0), compounds represented by the above-described formula (9-0) are useful, and from the standpoint of chromatic purity of a blue light emitting material, compounds represented by the following formula (9) are preferable, compounds represented by the following formula (10) are more preferable, and from the standpoint of easiness of synthesis, compounds represented by the following formula (10-0) are preferable. Compounds represented by the following formula (9), the following formula (10), the following formula (9-0) and the following formula (10-0) are useful also as materials of an organic transistor, a light emitting device and the like by fabricating into a film.

(9)

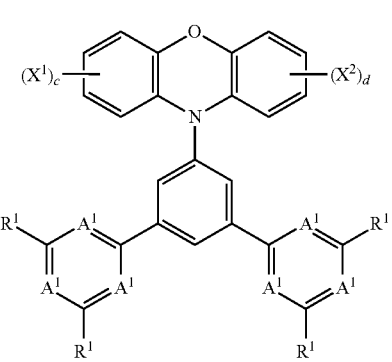

(wherein $A^1$, $R^1$, $X^1$, $X^2$, c and d represent the same meaning as described above.)

(10)

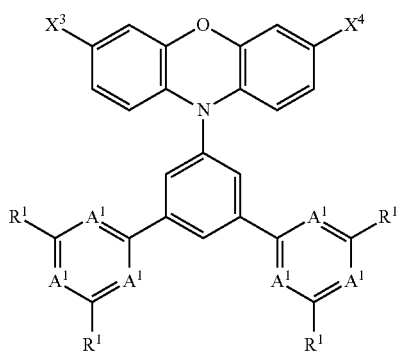

(wherein $A^1$ and $R^1$ represent the same meaning as described above. $X^3$ and $X^4$ each independently represent a halogen atom, —B(OH)$_2$, a borate ester residue, —MgX$^5$ (X$^5$ represents a halogen atom.), a stannyl group, an alkyl sulfonate group, an aryl sulfonate group or an arylalkyl sulfonate group.)

(10-0)

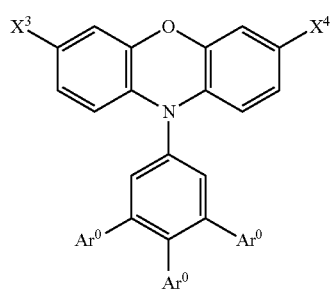

(wherein Ar$^0$ represents the same meaning as described above. At least two Ar$^0$s are groups represented by the above-described formula (A). $X^3$ and $X^4$ each independently represent a halogen atom, —B(OH)$_2$, a borate ester residue, —MgX$^5$ (X$^5$ represents a halogen atom.), a stannyl group, an alkyl sulfonate group, an aryl sulfonate group or an aryl alkyl sulfonate group.).

Examples of the group capable of participating in polymerization represented by $X^1$ and $X^2$ in the above-described formulae (9-0) and (9) include a halogen atom, —B(OH)$_2$, a borate ester residue, —MgX$^5$ (X$^5$ represents a halogen atom), a stannyl group, an alkyl sulfonate group, an aryl sulfonate group and an arylalkyl sulfonate group.

The halogen atom as the group capable of participating in polymerization includes a fluorine atom, a chlorine atom, a bromine atom and an iodine atom, and from the standpoint of easiness of functional group change, a chlorine atom, a bromine atom and an iodine atom are preferable, a bromine atom is more preferable.

The borate ester residue as the group capable of participating in polymerization includes dialkyl ester residues, diaryl ester residues and diaryl alkyl ester residues, and additionally, groups represented by the following formulae.

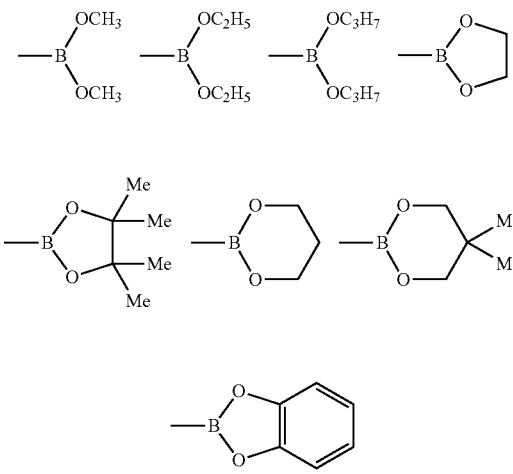

—MgX$^5$ as the group capable of participating in polymerization includes a magnesium chloride group, a magnesium bromide group and a magnesium iodide group.

The stannyl group as the group capable of participating in polymerization includes a stannyl group, a trichlorostannyl group, a trimethylstannyl group, a triethylstannyl group, a tri-n-butylstannyl group, a triphenylstannyl group, a tribenzylstannyl group.

The alkyl sulfonate group as the group capable of participating in polymerization includes a methane sulfonate group, an ethane sulfonate group, a trifluoromethane sulfonate group and the like. The aryl sulfonate group includes a benzene sulfonate group, a p-toluene sulfonate group and the like. The arylalkyl sulfonate group includes a benzyl sulfonate group and the like.

The compounds represented by the above-described formulae (9-0) and (9) include compounds represented by the following formulae.

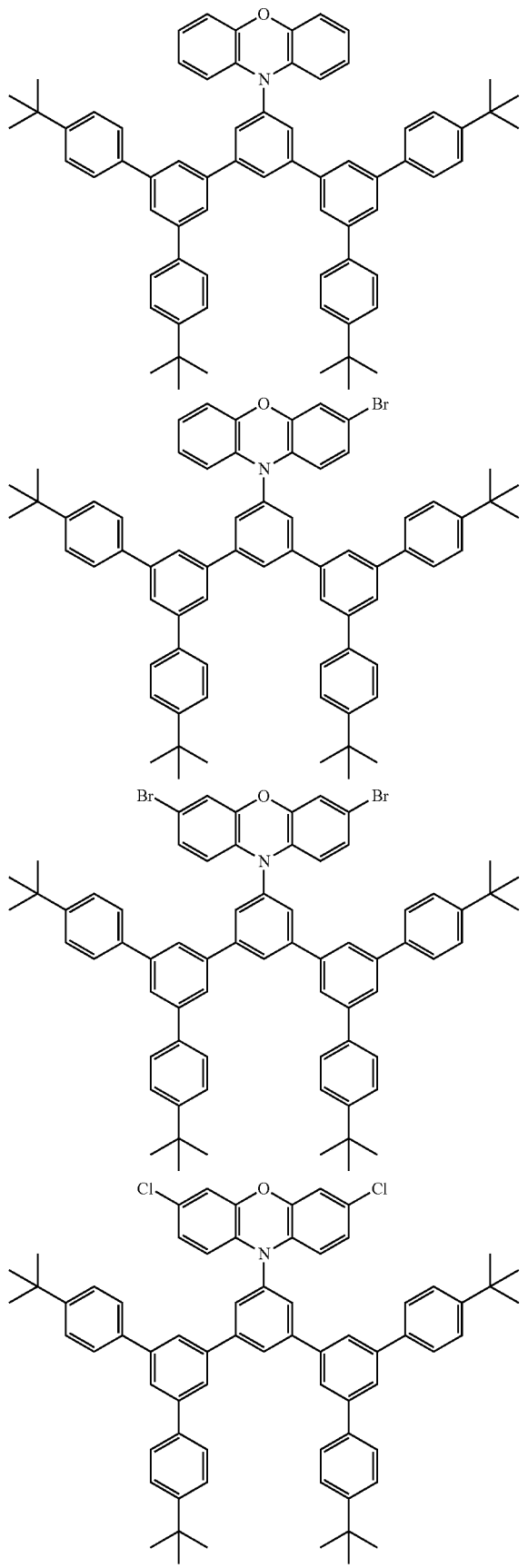
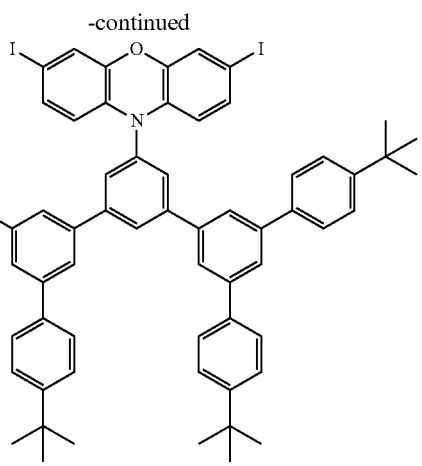
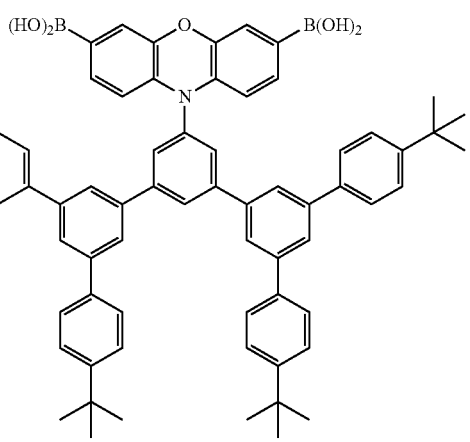
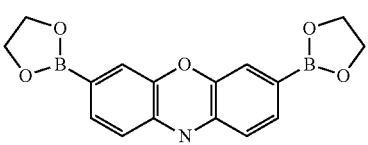
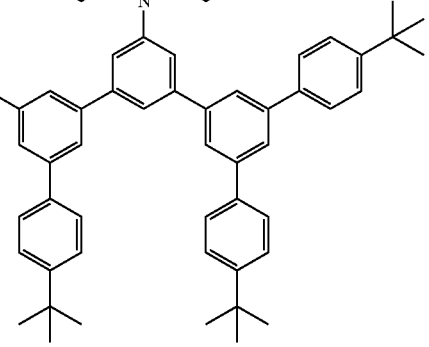

-continued

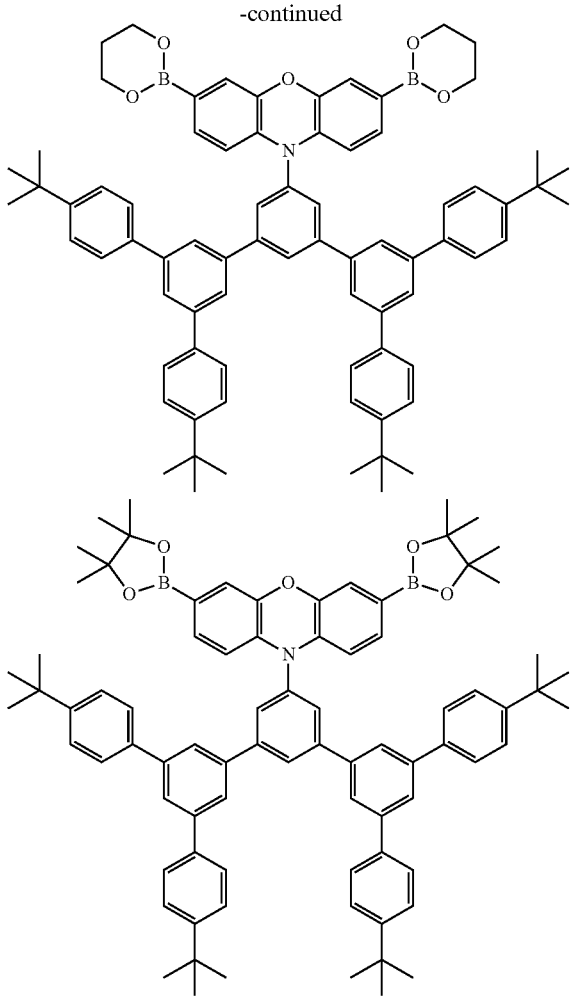

In the above-described formulae (10-0) and (10), the groups and atoms represented by $X^3$ and $X^4$ are the same as those explained and exemplified as the group and atom represented by $X^1$ and $X^2$.

<Production Method>

The polymer compound of the present invention may be produced by any method, and exemplified are a method of producing a polymer compound comprising a repeating unit represented by the above-described formula (0') comprising polymerizing a compound represented by the following formula (10-0) in the presence of a transition metal catalyst, and a method of producing a polymer compound comprising a repeating unit represented by the above-described formula (2') comprising polymerizing a compound represented by the following formula (10) in the presence of a transition metal catalyst. The method of producing a polymer compound comprising a repeating unit represented by the above-described formula (2') will be illustrated below as a typical example. For example, a polymer compound comprising a repeating unit represented by the above-described formula (2') can be produced by a method including polymerizing a compound represented by the following formula (10) in the presence of a transition metal catalyst. When the polymer compound of the present invention contains a repeating unit other than the repeating unit represented by the above-described formula (2'), a monomer constituting the repeating unit other than the repeating unit represented by the formula (2') may advantageously be allowed to co-exist.

The polymerization method used for polymerization in the presence of a transition metal catalyst includes methods [3], [4], [11], [12], [13], [14] and [15] described later, and the like.

The use amount of the transition metal catalyst is usually in the range of 0.0001 mol to 10 mol with respect to 1 mol of the amount of all monomers to be subjected to polymerization, though varying depending on the polymerization method.

The above-described transition metal catalyst includes a nickel catalyst, a palladium catalyst and the like.

The above-described nickel catalyst includes an ethylenebis(triphenylphosphine)nickel complex, a tetrakis(triphenylphosphine)nickel complex, a bis(cyclooctadienyl)nickel complex, and the like.

The above-described palladium catalyst includes palladium acetate, a palladium[tetrakis(triphenylphosphine)] complex, a bis(tricyclohexylphosphine)palladium complex, a dichlorobis(triphenylphosphine)palladium complex, and the like.

The polymer compound of the present invention, when having a vinylene group on its main chain, corresponds to a compound represented by the above-described formula (0), and can be produced, for example, by methods described in JP-A No. 5-202355 using a monomer having a group capable of participating in polymerization, and if necessary using other monomers. That is:

[1] polymerization by the Wittig reaction of a compound having an aldehyde group with a compound having a phosphonium base,

[2] polymerization by the Wittig reaction of a compound having an aldehyde group and a phosphonium base,

[3] polymerization by the Heck reaction of a compound having a vinyl group with a compound having a halogen atom,

[4] polymerization by the Heck reaction of a compound having a vinyl group and a halogen atom,

[5] polymerization by the Horner-Wadsworth-Emmons method of a compound having an aldehyde group with a compound having an alkyl phosphonate group,

[6] polymerization by the Horner-Wadsworth-Emmons method of a compound having an aldehyde group and an alkyl phosphonate group,

[7] polycondensation by a dehydrohalogenation method of a compound having two or more methyl halide groups,

[8] polycondensation by a sulfonium salt decomposition method of a compound having two or more sulfonium bases,

[9] polymerization by the Knoevenagel reaction of a compound having an aldehyde group with a compound having an acetonitrile group,

[10] polymerization by the Knoevenagel reaction of a compound having an aldehyde group and an acetonitrile group,

[11] polymerization by the McMurry reaction of a compound having two or more aldehyde groups, and the like are listed.

These methods [1] to [11] are as shown in the following formulae.

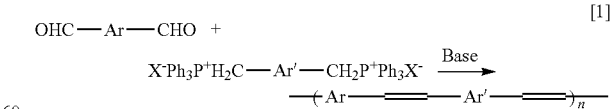

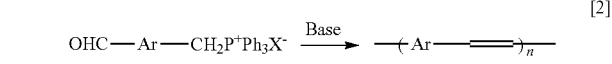

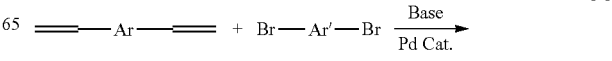

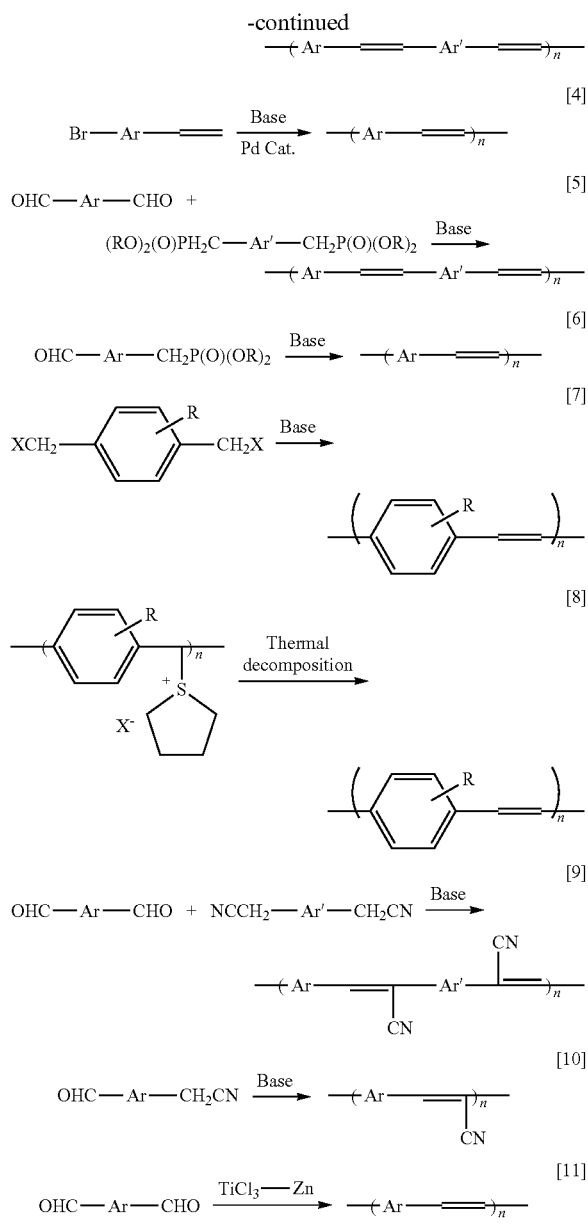
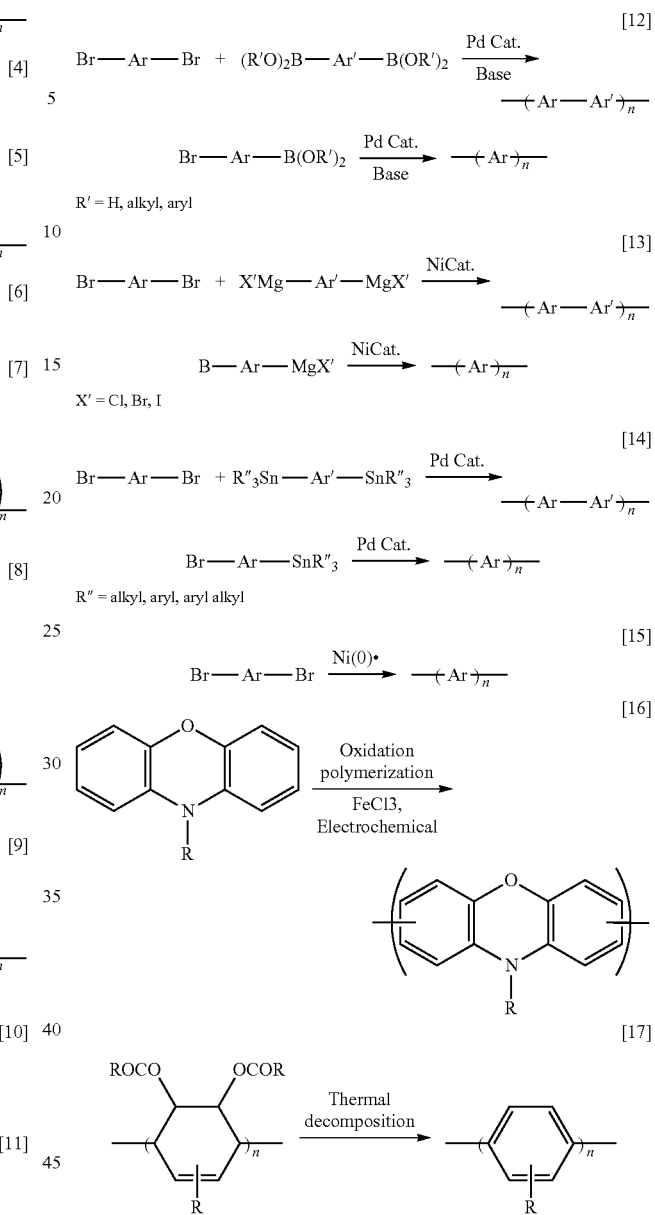

The polymer compound of the present invention, when a vinylene group is not carried on its main chain, can be produced by polymerization using a monomer having a group capable of participating in polymerization, and if necessary using other monomers. That is,

[12] polymerization by the Suzuki coupling reaction,

[13] polymerization by the Grignard reaction,

[14] polymerization by the Stifle coupling reaction,

[15] polymerization with a Ni(0) catalyst,

[16] polymerization with an oxidizer such as FeCl₃ and the like, electrochemical oxidation polymerization,

[17] a method by decomposition of an intermediate polymer having a suitable leaving group, and the like are listed.

These methods [12] to [17] as shown in the following formulae.

Among these methods, polymerization by the Wittig reaction, polymerization by the Heck reaction, polymerization by the Horner-Wadsworth-Emmons method, polymerization by the Knoevenagel reaction, polymerization by the Suzuki coupling reaction, a method of polymerization by the Grignard reaction, a method using the Stille coupling and polymerization with a Ni(0) catalyst are preferable from the standpoint of structure control, and polymerization by the Suzuki coupling reaction, polymerization by the Grignard reaction and polymerization with a Ni(0) catalyst are preferable from the standpoint of easy availability of raw materials and the operability of the polymerization reaction.

It may be advantageous that a monomer is, if necessary dissolved in an organic solvent, and reacted at a temperature of not lower than the melting point and not higher than the boiling point of the organic solvent using, for example, an alkali or a suitable catalyst. For details, a reference can be made to descriptions in "Organic Reactions", vol. 14, p. 270-

490, John Wiley&Sons, Inc., 1965, "Organic Reactions", vol. 27, p. 345-390, John Wiley&Sons, Inc., 1982, "Organic Syntheses", Collective Volume VI, p. 407-411, John Wiley&Sons, Inc., 1988, Chemical Review (Chem. Rev.), vol. 95, p. 2457 (1995), Journal of Organometalic Chemistry (J. Organomet. Chem.), vol. 576, p. 147 (1999), Journal of Practical Chemistry (J. Prakt. Chem.), vol. 336, p. 247 (1994), Macromolecular Chemistry, Macromolecular Symposium (Makromol. Chem., Macromol. Symp.), vol. 12, p. 229 (1987), and the like.

The above-described organic solvent is preferably subjected to sufficient deoxidation and dehydration treatments, for suppressing side reactions. The reaction system is preferably an inert atmosphere, however, this is not applicable to a reaction in a two-phase system with water such as in the Suzuki coupling reaction and the like.

The above-described alkalis and catalysts are preferably those which are sufficiently dissolved in a solvent to be used in the reaction. The method of adding an alkali or a catalyst includes methods in which a solution of an alkali or a catalyst is slowly added while stirring the reaction solution under an inert atmosphere such as argon, nitrogen and the like, or the reaction solution is slowly added to a solution of an alkali or a catalyst.

Since the purity of the polymer compound of the present invention exerts an influence on a light emission property, it is preferable to purity monomers before polymerization by a method such as distillation, sublimation purification, recrystallization and the like before performing polymerization, and it is preferable that, after synthesis thereof, a purification treatment such as re-deposition purification, chromatographic fractionation and the like is carried out.

When several raw material monomers are used in production of the polymer compound of the present invention, these may be mixed and reacted in one time, or if necessary, these may be divided and mixed and reacted.

The reaction conditions will be described in detail. In the case of the Wittig reaction, the Horner reaction, the Knoevengel reaction and the like, the reaction is carried out using an alkali in an amount of the equivalent or more, preferably 1 to 3 equivalents with respect to the functional group of a monomer. The above-described alkali includes potassium-tert-butoxide, sodium-tert-butoxide, metal alcoholates such as sodium ethylate, lithium ethylate and the like, hydride reagents such as sodium hydride and the like, amides such as sodium amide and the like. The above-described solvent includes N,N-dimethylformamide, tetrahydrofuran, dioxane, toluene and the like. The temperature of the above-described reaction is usually room temperature to 150° C. The time of the above-described reaction is a time in which the reaction progresses sufficiently, and is usually 5 minutes to 40 hours. The concentration in the above-described reaction is usually 0.1 to 20 wt %.

In the case of the Heck reaction, a monomer is reacted using a palladium catalyst in the presence of a base such as triethylamine and the like. For example, a solvent having a relatively high boiling point such as N,N-dimethylformamide, N-methylpyrrolidone and the like is used, the reaction temperature is 80 to 160° C., and the reaction time is 1 to 100 hours.

In the case of the Suzuki coupling, a palladium catalyst such as palladium[tetrakis(triphenylphosphine)], palladium acetates and the like is used, and an inorganic base such as potassium carbonate, sodium carbonate, barium hydroxide and the like, an organic base such as triethylamine and the like, or an inorganic salt such as cesium fluoride and the like is added in an amount of the equivalent or more, preferably 1 to 10 equivalents with respect to the monomer and reacted. It may also be permissible that an inorganic salt is prepared into an aqueous solution and reacted in a two-phase system. The solvent includes N,N-dimethylformamide, toluene, dimethoxyethane, tetrahydrofuran and the like. The reaction temperature is preferably 50 to 160° C. The reaction solution may be refluxed by heating up to around the boiling point of the solvent. The reaction time is 1 to 200 hours.

In the case of the Grignard reaction, a method is mentioned in which a halide and metal Mg are reacted in an ether solvent such as tetrahydrofuran, diethyl ether, dimethoxyethane and the like to prepare a Grignard reagent solution which is mixed with a monomer solution prepared separately, and a nickel or palladium catalyst is added while paying attention to an excessive reaction, then, the reaction mixture is heated and reacted while refluxing. The Grignard reagent is used in an amount of the equivalent or more, preferably 1 to 1.5 equivalents with respect to the monomer.

In the case of reacting in the presence of a nickel catalyst, a method of polymerization with the above-described Ni(0) catalyst is mentioned.

Compounds represented by the above-described formula (10) in which $X^3$ and $X^4$ represent a halogen atom can be synthesized by a method of halogenating a compound represented by the following formula (10-1) in the presence of a halogenating reagent.

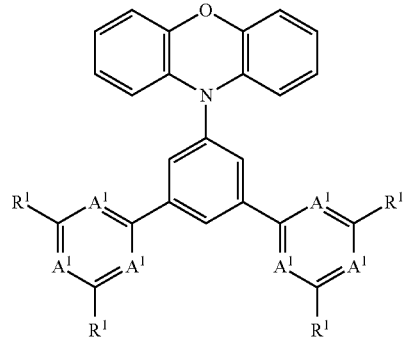

(10-1)

(wherein $A^1$ and $R^1$ represent the same meaning as described above.).

Exemplified as the halogenating reagent are chlorinating reagents such as chlorine, N-chlorosuccinimide and the like, brominating reagents such as bromine, N-bromosuccinimide, 1,3-dibromo-5,5-dimethylhydantoin, benzyltrimethyl ammonium tribromide and the like, and iodinating reagents such as N-iodosuccinimide and the like.

The compound represented by the above-described formula (10-1) can be synthesized by reacting a compound represented by the following formula (11) and phenoxazine in the presence of a transition metal catalyst and a base according to, for example, a method described in Angew. Chem. Int. Ed. 1998, 37, 2046.

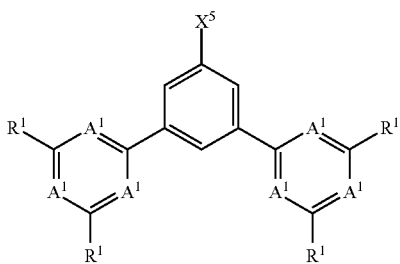

(11)

(wherein $A^1$ and $R^1$ represent the same meaning as described above. $X^5$ represents a chlorine atom, a bromine atom, an iodine atom, an alkylsulfonyl group, an arylsulfonyl group or an arylalkylsulfonyl group.), $X^5$ represents an alkylsulfonyl group, an arylsulfonyl group or an arylalkylsulfonyl group, from the standpoint of easiness of synthesis of a compound (11).

A compound represented by the above-described formula (11) in which $X^5$ represents an alkylsulfonyl group, an arylsulfonyl group or an arylalkylsulfonyl group can be synthesized by reacting a compound represented by the following formula (12) and the correspondent sulfonyl chloride compound in the presence of a base.

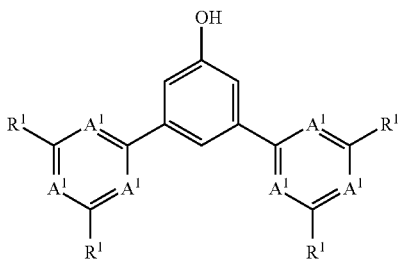

(12)

(wherein $A^1$ and $R^1$ represent the same meaning as described above.).

<Composition>

The composition of the present invention is a composition comprising the polymer compound of the present invention. Embodiments of the composition of the present invention include a composition comprising at least one material selected from the group consisting of a hole transporting material, an electron transporting material and a light emitting material, and the polymer compound of the present invention; and a composition comprising the polymer compound of the present invention and a solvent (hereinafter, referred to as "solution composition"). In the present invention, the polymer compound of the present invention, a hole transporting material, an electron transporting material, a light emitting material, and a solvent may each be used singly, or two or more materials of each of them may be used.

When the composition of the present invention comprises a hole transporting material, an electron transporting material and a light emitting material, regarding the ratio of the sum of the hole transporting material, electron transporting material and light emitting material to the polymer compound of the present invention, the total amount of the hole transporting material, electron transporting material and light emitting material is usually 1 to 10000 parts by weight, preferably 10 to 1000 parts by weight, more preferably 20 to 500 parts by weight with respect to 100 parts by weight of the polymer compound of the present invention.

Next, the solution composition which is a typical embodiment of the composition of the present invention will be described.

The proportion of the solvent in the above-described solution composition is usually 1 to 99.9 wt %, preferably 60 to 99.5 wt %, further preferably 80 to 99.0 wt % with respect to the total weight of the solution composition. The viscosity of the solution composition varies depending on an printing method, and when the solution composition passes through a discharge apparatus such as in an inkjet print method and the like, the viscosity at 25° C. is preferably 1 to 20 mPa·s for preventing clogging and curved flying in discharging.

The above-described solution composition may further contain an additive for adjusting viscosity and/or surface tension. This additive includes a high molecular weight polymer compound for enhancing viscosity (hereinafter, referred to as "thickening reagent"), a poor solvent, a low molecular weight compound for lowering viscosity, a surfactant for lowering surface tension, and the like.

The above-described thickening reagent may advantageously be one which is soluble in the same solvent as contained in the polymer compound of the present invention and which does not disturb light emission and charge transportation, and examples thereof include high molecular weight polystyrene, polymethyl methacrylate and the like. It is also possible to use a poor solvent as the thickening reagent. That is, by adding a small amount of a poor solvent against solid components in the solution composition, the viscosity can be enhanced.

The solution composition of the present invention may further contain an antioxidant for improving preservation stability, and examples thereof include those which are soluble in the same solvent as contained in the polymer compound of the present invention and which do not disturb light emission and charge transportation, and preferable are phenol antioxidants, phosphorus antioxidants and the like.

The solvent to be contained in the above-described solution composition includes chlorine-based solvents such as chloroform, methylene chloride, 1,2-dichloroethane, 1,1,2-trichloroethane, chlorobenzene, o-dichlorobenzene and the like; ether solvents such as tetrahydrofuran, dioxane, anisole and the like, aromatic hydrocarbon solvents such as toluene, xylene and the like; aliphatic hydrocarbon solvents such as cyclohexane, methylcyclohexane, n-pentane, n-hexane, n-heptane, n-octane, n-nonane, n-decane and the like; ketone solvents such as acetone, methyl ethyl ketone, cyclohexanone, benzophenone, acetophenone and the like; ester solvents such as ethyl acetate, butyl acetate, ethylcellosolve acetate, methyl benzoate, phenyl acetate and the like; polyhydric alcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, 1,2-hexane diol and the like and derivatives thereof; alcohol solvents such as methanol, ethanol, propanol, isopropanol, cyclohexanol and the like; sulfoxide solvents such as dimethyl sulfoxide and the like; amide solvents such as N-methyl-2-pyrrolidone, N,N-dimethylformamide and the like. These solvents may be used singly or in combination of two or more. Further, the number of these solvents is preferably 2 or more, more preferably 2 to 3, particularly preferably 2, from the standpoint of film formability and from the standpoint of device properties, and the like.

When two of the above-described solvents are combined, one of these solvents may be solid state at 25° C. Regarding the combination of two solvents, it is preferable that one solvent has a boiling point of 180° C. or higher and it is more preferable that one solvent has a boiling point of 200° C. or higher from the standpoint of film formability, and it is preferable that the polymer compound of the present invention is dissolved at 60° C. in an amount of 1 wt % or more in both two solvents and it is preferable that the polymer compound of the present invention is dissolved at 25° C. in an amount of 1 wt % or more in at least one solvent from the standpoint of viscosity.

When three or more of the above-described solvents are combined, the amount of a solvent having highest boiling point is preferably 40 to 90 wt %, more preferably 50 to 90 wt % with respect to the total weight of these three or more solvents, from the standpoint of viscosity and film formability.

The above-described solution composition may contain water, a metal and its salt in an amount of 1 to 1000 ppm (based on weight). The metal includes lithium, sodium, calcium, potassium, iron, copper, nickel, aluminum, zinc, chromium, manganese, cobalt, platinum and iridium. The above-described solution composition may contain silicon, phosphorus, fluorine, chlorine and bromine in an amount of 1 to 1000 ppm (based on weight).

Using the above-described solution composition, the film of the present invention can be fabricated easily by an application method such as a spin coat method, a casting method, a micro gravure coat method, a gravure coat method, a bar coat method, a roll coat method, a wire bar coat method, a dip coat method, a spray coat method, a screen printing method, a flexo printing method, an offset printing method, an inkjet print method and the like.

<Film>

The film of the present invention includes a light emitting film, an electric conductive film and an organic semiconductor film.

The electric conductive film has a surface resistance of preferably 1 KΩ/□ or less. The electric conductive film of the present invention can be doped with a Lewis acid, an ionic compound or the like to enhance electric conductivity.

In the organic semiconductor film, it is preferable that a larger parameter among electron mobility and hole mobility is $1 \times 10^{-5}$ cm$^2$/V/sec or more. An organic transistor can be fabricated by forming an organic semiconductor film on a Si substrate carrying a gate electrode and an insulation film of SiO$_2$ and the like formed thereon, and forming a source electrode and a drain electrode with Au and the like.

<Light Emitting Device>

The light emitting device of the present invention comprises the polymer compound of the present invention, and for example, is a light emitting device having electrodes consisting of an anode and a cathode, and a layer comprising the polymer compound of the present invention disposed between the electrodes.

The light emitting device of the present invention has a pair of electrodes consisting of an anode and a cathode, and a film composed of one layer (single-layer type) or several layers (multi-layer type) having a light emitting layer sandwiched between the electrodes. At least one layer of the film layer contains the polymer compound of the present invention. The total content of the polymer compound of the present invention in the above-described film is usually 0.1 to 100 wt %, preferably 0.1 to 80 wt %, more preferably 0.5 to 60 wt % with respect to the weight of the whole light emitting layer. In the light emitting device of the present invention, it is preferable that the above-described light emitting layer contains the polymer compound of the present invention as a light emitting material.

When the light emitting device of the present invention is of single-layer type, the above-described film is a light emitting layer, and this light emitting layer contains the polymer compound of the present invention. When the light emitting device of the present invention is of multi-layer type, for example, the following constitutions are mentioned.

(a) anode/hole injection layer (hole transporting layer)/light emitting layer/cathode (b) anode/light emitting layer/electron injection layer (electron transporting layer)/cathode (c) anode/hole injection layer (hole transporting layer)/light emitting layer/electron injection layer (electron transporting layer)/cathode The anode of the light emitting device of the present invention feeds holes to a hole injection layer, a hole transporting layer, a light emitting layer and the like, and it is effective that the anode has a work function of 4.5 eV or more. As the material of the anode, a metal, an alloy, a metal oxide, an electric conductive compound, a mixture of them, and the like can be used. The material of the anode includes electric conductive metal oxides such as tin oxide, zinc oxide, indium oxide, indium tin oxide (ITO) and the like, metals such as gold, silver, chromium, nickel and the like, further, mixtures or laminates of these electric conductive metal oxides with metals, inorganic electric conductive substances such as copper iodide, copper sulfide and the like, organic electric conductive materials such as polyanilines, polythiophenes (PEDOT, and the like), polypyrrole and the like, laminates of these materials with ITO, and the like.

The cathode of the light emitting device of the present invention feeds electrons to an electron injection layer, an electron transporting layer, a light emitting layer and the like. As the material of the cathode, a metal, an alloy, a metal halide, a metal oxide, an electric conductive compound or a mixture of them can be used, and examples thereof include alkali metals (lithium, sodium, potassium and the like) and fluorides and oxides thereof, alkaline earth metals (magnesium, calcium, barium, cesium and the like) and fluorides and oxides thereof, gold, silver, lead, aluminum, alloys and mixed metals (sodium-potassium alloy, sodium-potassium mixed metal, lithium-aluminum alloy, lithium-aluminum mixed metal, magnesium-silver alloy, magnesium-silver mixed metal, and the like), rare earth metals (indium, ytterbium and the like), etc.

The hole injection layer and the hole transporting layer of the light emitting device of the present invention may advantageously be layers having any of a function of injecting holes from an anode, a function of transporting holes, and a function of blocking electrons injected from a cathode. As the material of these layers, known materials can be used, and examples thereof include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne based compounds, porphyrin based compounds, polysilane based compounds, poly(N-vinylcarbazole) derivatives, organic silane derivatives, the polymer compound of the present invention and the like, and polymers containing these compounds. Additionally, electric conductive polymer oligomers such as aniline based copolymers, thiophene oligomers, polythiophene and the like are mentioned. These materials may be used singly or in combination of some of them. The above-described hole injection layer and the above-described hole transporting layer may have a single layer structure composed of one or two or more of the above-described materials, or a multi-layer structure composed of several layers having the same composition or different compositions.

The electron injection layer and the electron transporting layer of the light emitting device of the present invention may advantageously be layers having any of a function of injecting electrons from a cathode, a function of transporting electrons and a function of blocking holes injected from an anode. Examples of the material used in the electron injection layer and the electron transporting layer include triazole derivatives, oxazole derivatives, oxadiazole derivatives, imidazole derivatives, fluorenone derivatives, anthraquinodimethane derivatives, anthrone derivatives, diphenylquinone derivatives, thiopyran dioxide derivatives, carbodiimide derivatives, fluorenylidene methane derivatives, distyrylpyrazine derivatives, aromatic tetracarboxylic anhydrides such as naphthalene, perylene and the like, phthalocyanine derivatives, various metal complexes typified by metal complexes of 8-quinolinol derivatives and metal complexes having metalphthalocyanine, benzooxazole or benzothiazole as a ligand, organic silane derivatives, the polymer compound of the present invention, and the like The above-described electron injection layer and the above-described electron transporting layer may have a single layer structure composed of one or two or more of the above-described materials, or a multi-layer structure composed of several layers having the same composition or different compositions.

In the light emitting device of the present invention, as the material of an electron injection layer and an electron transporting layer, use can be made of also inorganic compounds as insulating materials or semiconductors. If an electron injection layer and an electron transporting layer are constituted of an insulating material or a semiconductor, leak of electric current can be effectively prevented and electron injectability can be improved. As such an insulating material, use can be made of at least one metal compound selected from the group consisting of alkali metal chalcogenides, alkaline earth metal chalcogenides, alkali metal halides and alkaline earth metal halides. Preferable alkali metal chalcogenides include CaO, BaO, SrO, BeO, BaS and CaSe. The semiconductor constituting an electron injection layer and an electron transporting layer includes oxides, nitrides or oxynitrides containing at least one element selected from the group consisting of Ba, Ca, Sr, Yb, Al, Ga, In, Li, Na, Cd, Mg, Si, Ta, Sb and Zn, and the like. These oxides, nitrides and oxynitrides may be used singly or in combination of two or more In the light emitting device of the present invention, a reducing dopant may be added to an interface region between a cathode and an adjacent film. As the reducing dopant, at least one compound is preferable selected from the group consisting of oxides of alkali metals and alkaline earth metals, oxides of alkaline earth metals, rare earth metals and alkali metals, halides of alkali metals, oxides of alkaline earth metals, halides of alkaline earth metals, oxides of rare earth metals, halides of rare earth metals, alkali metal complexes, alkaline earth metal complexes and rare earth metal complexes.

The light emitting layer of the light emitting device of the present invention has a function in which, in application of voltage, holes can be injected from an anode or a hole injection layer and electrons can be injected from a cathode or an electron injection layer, a function in which injected charges (electrons and holes) are moved by the electric field force, and a function to provide a filed for recombination of electrons and holes, thereby causing light emission. In the light emitting layer of the light emitting device of the present invention, at least the polymer compound of the present invention is preferably contained, and a host material for the polymer compound as a guest material may also be contained. Examples of the above-described host material include those having a fluorene skeleton, those having a carbazole skeleton, those having a diarylamine skeleton, those having a pyridine skeleton, those having a pyrazine skeleton, those having a triazine skeleton, those having an arylsilane skeleton, and the like. It is preferable that Tl of the above-described host material (energy level of lowest triple excited state) is larger than that of the guest material, and it is further preferable that its difference is larger than 0.2 eV. The above-described host material may be a low molecular weight compound or a polymer compound. A light emitting layer having the above-described host material doped with the above-described light emitting material can be formed, by mixing the above-described host material and the above-described light emitting material such as metal complexes and the like and applying the mixture, or co-depositing them, and the like.

Methods for forming the above-described layers in the light emitting device of the present invention include a vacuum vapor-deposition method (resistance heating vapor-deposition method, electron beam method and the like), a sputtering method, an LB method, a molecular stacking method, an application method (casting method, spin coat method, bar coat method, blade coat method, roll coat method, gravure printing, screen printing, inkjet method and the like), etc. Of them, the application method is preferably used to form a film since the production process can be simplified. In the above-described application method, the polymer compound of the present invention is dissolved in a solvent to prepare an application solution, and the application solution is applied on a desired layer (or electrode) and dried, thus, the layer can be formed. In the application solution, a resin may be contained as a host material and/or a binder, and the resin may be in condition of dissolution or dispersion in a solvent. As the above-described resin, non-conjugated polymers (for example, polyvinylcarbazole) and conjugated polymers (for example, polyolefin based polymer) can be used. More specifically, the resin can be selected from, for example, polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resin, ketone resin, phenoxy resin, polyamide, ethyl cellulose, vinyl acetate, ABS resin, polyurethane, melamine resin, unsaturated polyester resin, alkyd resin, epoxy resin, silicon resin and the like, in accordance with the object. The solution may also contain an antioxidant, a viscosity modifier and the like, as optional components.

—Photoelectric Device—

The polymer compound of the present invention can be used for production of a photoelectric device.

The photoelectric device includes photoelectric conversion devices and the like, for example, a device having a layer containing the polymer compound of the present invention disposed between two electrodes at least one of which is transparent or semi-transparent, and a device having an inter-digitated electrode formed on a layer containing the polymer compound of the present invention formed on a substrate. For improving properties, fullerenes, carbon nanotubes and the like may be mixed.

The method for producing a photoelectric conversion device includes methods described in Japanese Patent No.

3146296, for example, a method in which a layer (film) containing the polymer compound of the present invention is formed on a substrate having a first electrode, and a second electrode is formed thereon, and a method in which a layer (film) containing the polymer compound of the present invention is formed on a pair of interdigitated electrodes formed on a substrate. Either the first electrode or the second electrode is transparent or semi-transparent.

EXAMPLES

The present invention will be illustrated more specifically based on examples below, but the present invention is not limited to them. Light emission chromaticity is represented according to the chromaticity coordinate defined by Commission internationale de l'éclairage, and the lower y value denotes better chromaticity blue color. The number average molecular weight and the weight average molecular weight were measured according to the following method.
(Number Average Molecular Weight and Weight Average Molecular Weight)

For the number average molecular weight and the weight average molecular weight, GPC (manufactured by Shimadzu Corporation: trade name: LC-10 Avp) was used to measure polystyrene-equivalent number average molecular weight and weight average molecular weight. A polymer compound to be measured was dissolved in tetrahydrofuran so as to give a concentration of about 0.5 wt %, and the solution was injected in an amount of 50 μL into GPC. Tetrahydrofuran was used as the mobile phase of GPC, and allowed to flow at a flow rate of 0.6 mL/min. As the column, two TSKgel Super HM-H (manufactured by Tosoh Corp.) and one TSKgel Super H2000 (manufactured by Tosoh Corp.) were connected in series. A differential refractive index detector (manufactured by Shimadzu Corp., trade name: RID-10A) was used as a detector.

Example 1

Synthesis of Compound A

Synthesis of Compound A-1

Into a 500 ml three-necked flask was charged 9.59 g of 3,5-dibromophenol, 30.89 g of 3,5-bis(4-tert-butylphenyl)phenylboric acid (synthesized according to a method described in JP-A No. 2005-82730) and 95 g of tetraethyl ammonium hydroxide (20 wt % aqueous solution, 129 mmol), then, an atmosphere in the flask was purged with nitrogen. To this was added 215 ml of toluene and 0.15 g (0.22 mmol) of dichlorobis(triphenylphosphine)palladium, and the mixture was heated at 100° C. for 8 hours. Thereafter, the mixture was left to cool, to find deposition of a crystal. This crystal was dissolved by adding 1 L of chloroform, and the resultant solution was acidified by adding 1N hydrochloric acid, and separated. The resultant aqueous phase was extracted with 500 ml of chloroform, and chloroform after extraction was combined with the organic phase, and this was washed with water and saturated aqueous solution of sodium chloride. The organic phase after washing was filtrated through a glass filter paved with 100 g of silica gel, and the solvent was distilled off, to obtain 41.75 g of a crude product. To this was added 250 ml of hexane, and the mixture was heated up to reflux temperature, then, allowed to cool slowly to room temperature, filtrated, and washed with hexane, to obtain 28.04 g of a compound A-1 represented by the following formula.

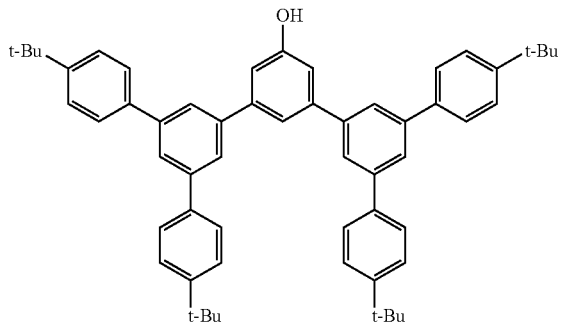 [SMILES: CC(C)(C)c1ccc(-c2cc(-c3ccc(C(C)(C)C)cc3)cc(-c3cc(O)cc(-c4cc(-c5ccc(C(C)(C)C)cc5)cc(-c5ccc(C(C)(C)C)cc5)c4)c3)c2)cc1]

*LC-MS
APPI-MS, positive 775 ([M+H]$^+$, exact mass=774)
*$^1$H-NMR (300 MHz, CDCl$_3$)
δ 1.35 (36H, s), 5.19 (1H, s), 7.15 (s, 2H), 7.47 (d, 8H), 7.59 (s, 1H), 7.60 (d, BA), 7.78 (s, 6H)
*$^{13}$C-NMR (300 MHz, CDCl$_3$)
δ 31.8, 34.9, 113.9, 119.6, 125.2, 125.7, 126.2, 127.4, 138.6, 142.1, 142.6, 144.0, 150.9, 156.6

Synthesis of Compound A-2

An atmosphere in a 500 ml four-necked flask was purged with nitrogen, and 28.04 g of the compound A-1 and 12.99 g of N,N-dimethyl-4-aminopyridine were charged therein, and dissolved in 300 ml of dehydrated dichloromethane, and the solution was cooled down to 0° C. Into this, 25.01 g of anhydrous trifluoromethanesulfonic acid was dropped over a period of 30 minutes. The mixture was stirred for 20 minutes, then, a cooling bath was removed, and stirring was continued for 1.5 hours. The resultant mixed solution was filtrated by passing through a glass filter paved with 100 g of silica gel, and washed with 500 ml of toluene. The solvent was distilled off from the resultant mixed solution, to obtain 28.86 g of a compound A-2 represented by the following formula.

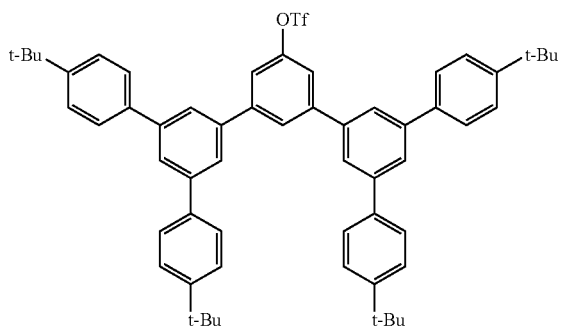

The compound was used in the next step without purification.
*LC-MS
ESI-MS, positive 945 ([M+K]$^+$, exact mass=906)
*$^1$H-NMR (300 MHz, CDCl$_3$)
δ 1.38 (36H, s), 7.52 (8H, d), 7.57 (2H, s), 7.64 (8H, d), 7.77 (4H, s), 7.85 (2H, s), 7.97 (1H, s)
*$^{13}$C-NMR (300 MHz, CDCl$_3$)
δ 31.7, 34.9, 119.3, 125.2, 126.2, 126.4, 126.6, 127.4, 138.2, 140.4, 143.0, 144.8, 150.7, 151.2

Synthesis of Compound A-3

An atmosphere in a 1 L four-necked flask was purged with nitrogen, and 6.11 g of phenoxazine was charged therein, and dissolved in 122 ml of dehydrated toluene. To this was added 0.71 g of tris(dibenzylideneacetone)dipalladium, 0.86 g of 1,1'-bis(diphenylphosphino)ferrocene and 15.21 g of cesium carbonate, and the mixture was heated at 110° C. A solution prepared by dissolving 28.86 g of the compound A-2 in 144 ml of dehydrated toluene which had been bubbled with nitrogen was dropped into this over a period of 1 hour. The mixture was stirred for 20 hours, then, the resultant mixture was hot-filtrated through a glass filter paved with 150 g of silica gel, and washed with 500 ml of toluene. The solvent was distilled off from the resultant mixed solution, to obtain 33.01 g of a crude product. This crude product was dissolved in 100 g of toluene, and the resultant solution was dropped into 1 L of methanol, to cause re-precipitation. The resultant solution was filtrated and washed with methanol, to obtain 50.02 g of a wet cake. To this was added 70 ml of toluene, and the mixture was heated to dissolve, and 200 ml of ethanol was dropped, to give rise to re-crystallization. Further, the resultant product was filtrated and washed with 100 ml of ethanol, to obtain 24.6 g of an amine coupled body. This amine coupled body was re-crystallized from a toluene:ethanol mixed solvent, to obtain 16.62 g of a compound A-3 represented by the following formula.

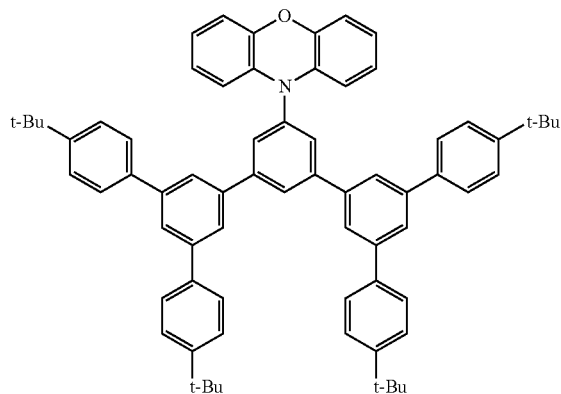 [SMILES: CC(C)(C)c1ccc(-c2cc(-c3ccc(C(C)(C)C)cc3)cc(-c3cc(-c4cc(-c5ccc(C(C)(C)C)cc5)cc(-c5ccc(C(C)(C)C)cc5)c4)cc(N4c5ccccc5Oc5ccccc54)c3)c2)cc1]

*LC-MS
APCI, positive 940 ([M+H]$^+$, exact mass=939)
*$^1$H-NMR (300 MHz, CDCl$_3$)
δ 1.37 (36H, s), 6.13-6.16 (2H, m), 6.62-6.71 (6H, m), 7.50 (8H, d), 7.64 (8H, d), 7.72 (2H, s), 7.83 (6H, s), 8.11 (1H, s)
*$^{13}$C-NMR (300 MHz, CDCl$_3$)
δ 31.7, 34.9, 113.7, 115.8, 121.7, 123.7, 125.0, 126.0, 126.1, 126.3, 127.4, 128.8, 134.6, 138.4, 140.4, 141.1, 142.8, 144.3, 145.3, 151.0

Synthesis of Compound A

An atmosphere in a 500 ml four-necked flask was purged with nitrogen, and 16.62 g of the compound A-3 was charged therein, and dissolved in 170 ml of chloroform. The resultant solution was cooled down to 0° C., and a solution prepared by dissolving 6.29 g of NBS (N-bromosuccinimide) in 13 ml of DMF (dimethylformamide) was dropped into this over a period of 50 minutes. The mixture was stirred for 10 minutes, then, an ice bath was removed, and stirring was continued for 3 hours. The resultant mixed solution was cooled down to 0° C. again, and a solution prepared by dissolving 0.10 g of NBS in 0.5 ml of DMF was dropped into this. The mixture was stirred for 1.5 hours at room temperature, then, 100 ml of water was dropped into this, and the mixture was separated. The resultant aqueous phase was extracted with 100 ml of toluene twice, and the extracted toluene was combined with the organic phase, and 500 ml of toluene was added to this, then, the resultant mixed solution was washed with water and saturated aqueous solution of sodium chloride. The mixed solution after washing was filtrated through a glass filter paved with 100 g of silica gel, and washed with toluene. The solvent was distilled off from the resultant mixed solution, to obtain 25.08 g of a compound A represented by the following formula.

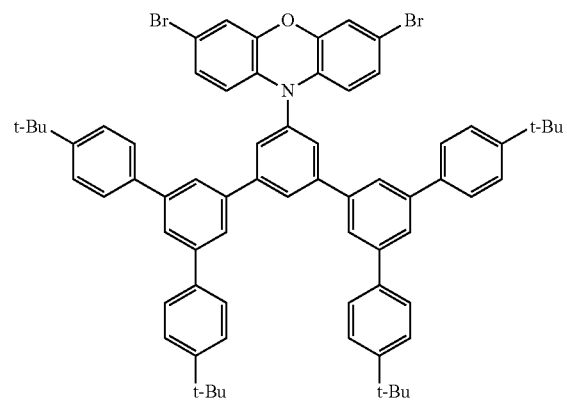 [SMILES: CC(C)(C)c1ccc(-c2cc(-c3ccc(C(C)(C)C)cc3)cc(-c3cc(-c4cc(-c5ccc(C(C)(C)C)cc5)cc(-c5ccc(C(C)(C)C)cc5)c4)cc(N4c5ccc(Br)cc5Oc5cc(Br)ccc54)c3)c2)cc1]

*LC-MS
APCI, positive 1096 ([M+H]$^+$, exact mass=1095)
*$^1$H-NMR (300 MHz, CDCl$_3$)
δ 1.37 (36H, s), 5.99 (2H, d), 6.75 (2H, d), 6.85 (2H, brs), 7.50 (8H, d), 7.61-7.65 (10H, m), 7.82 (6H, d), 8.11 (1H, s)
*$^{13}$C-NMR (300 MHz, CDCl$_3$)
δ 31.7, 34.9, 113.3, 114.9, 119.0, 125.0, 126.2, 126.7, 127.3, 128.2, 129.3, 133.5, 138.3, 139.6, 140.7, 142.9, 144.5, 145.6, 151.1

Example 2

Synthesis of Polymer Compound 1

Under a nitrogen atmosphere, 0.40 g of 2,7-bis(1,3,2-dioxaborolan-2-yl)-9,9-di-n-octylfluorene (synthesized according to a method described in JP-A No. 2007-70620), 0.82 g of the compound A, 2.8 mg of dichlorobis(triphenylphosphine)palladium, 0.52 g of trioctylmethyl ammonium chloride (manufactured by Aldrich, trade name: Aliquat 336) and 15 ml of toluene were mixed, and the mixture was heated at 90° C. Into the resultant mixed solution, 5 ml of a 17.5 wt % sodium carbonate aqueous solution was dropped, and the mixture was refluxed for 6 hours. After the reaction, to this was added 0.1 g of phenylboric acid, and the mixture was further refluxed for 4 hours. Then, to this was added 5 ml of a 12.5 wt % sodium diethyldithiacarbamate aqueous solution, and the mixture was stirred at 85° C. for 2 hours. After cooling, the mixture was washed with 10 ml of water twice, with 10 ml of a 3 wt % acetic acid aqueous solution twice and with 10 ml of water twice, and the resultant solution was dropped into 120 mL of methanol, and filtration thereof was performed to obtain a precipitate. This precipitate was dissolved in 25 mL of toluene, and purified by passing through a column having active alumina paved on silica gel. The resultant toluene solution was dropped into 120 ml of methanol, and the mixture was stirred, then, the resultant precipitate was filtrated and dried, to obtain 0.89 g of a polymer compound 1. The polymer compound 1 had a polystyrene-equivalent number average molecular weight of $1.4 \times 10^4$ and a polystyrene-equivalent weight average molecular weight of $2.2 \times 10^4$.

This polymer compound 1 had a fluorescence peak wavelength of 456 nm, and CIE chromaticity coordinate of (0.15, 0.14). This result is shown in Table 1.

Comparative Example 1

Synthesis of Polymer Compound 2

Under a nitrogen atmosphere, 1.87 g of 2,7-bis(1,3,2-dioxaborolan-2-yl)-9,9-di-n-octylfluorene, 1.66 g of 3,7-dibromo-10-(4-butylphenyl)-10H-phenoxazine (synthesized according to a method described in JP-A No. 2007-70620), 1 mg of palladium acetate, 5 mg of tri(o-methoxyphenyl)phosphine, 0.51 g of trioctylmethyl ammonium chloride (manufactured by Aldrich, trade name: Aliquat 336) and 25 ml of toluene were mixed, and the mixture was heated to 90° C. Into the resultant mixed solution, 7 ml of a 17.5 wt % sodium carbonate aqueous solution was dropped, and the mixture was refluxed for 74 hours. After the reaction, to this was added 54 mg of phenylboric acid, and the mixture was further refluxed for 4 hours. Then, to this was added 20 ml of a 12.5 wt % sodium diethyldithiacarbamate aqueous solution, and the mixture was stirred at 85° C. for 2 hours. The resultant solution was cooled, then, washed with 20 ml of water twice, with 20 ml of a 3 wt % acetic acid aqueous solution twice and with 20 ml of water twice, and the resultant solution was dropped into 450 mL of methanol, and the mixture was filtrated to obtain a precipitate. This precipitate was dissolved in 30 mL of toluene, and purified by passing through a column having active alumina paved on silica gel. The resultant toluene solution was dropped into 450 ml of methanol, and the mixture was stirred, then, the resultant precipitate was filtrated and dried, to obtain 1.83 g of a polymer compound 2. The polymer compound 2 had a polystyrene-equivalent number average molecular weight of $2.8 \times 10^4$ and a polystyrene-equivalent weight average molecular weight of $6.0 \times 10^4$.

This polymer compound 2 had a fluorescence peak wavelength of 462 nm and CIE chromaticity coordinate of (0.15, 0.18). This result is shown in Table 1.

Example 3

Synthesis of Compound B

Synthesis of Compound B-1

An atmosphere in a 100 ml three-necked flask was purged with nitrogen, then, 3,5-dibromo-toluene (4.90 g) was charged therein, and dissolved in 22 ml of THF. The solution was cooled down to −78° C., and hexyllithium (8.5 ml, 2.3M hexane solution) was added over a period of 3 minutes. The mixture was stirred for 1 hour, then, 3.00 ml of 1-bromohexane was added over a period of 1 minute and the mixture was heated slowly. After heating up to room temperature, the mixture was cooled down to 0° C., and a saturated ammonium chloride aqueous solution (30 ml) was added to stop the reaction. After separation, the aqueous phase was extracted with toluene (30 ml). The organic phase was mixed in, and the mixture was washed with water (30 ml) and saturated aqueous solution of sodium chloride (30 ml). The organic phase was dried over anhydrous magnesium sulfate, then, filtrated, and the solvent was distilled off, to obtain 7.69 g of a crude product of a compound B-1 represented by the following formula,

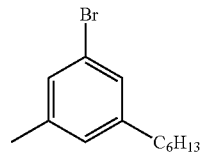

*GC-MS 254 ([M]$^+$, exact mass=254)

b.p. 90° C./0.8 mmHg

Synthesis of Compound B-2

An atmosphere in a 1 L four-necked flask was purged with nitrogen, and 23.90 g of the compound B-1 was dissolved in 230 ml of dehydrated 1,4-dioxane. 21.95 g of bis(pinacolato)diboron, 1.76 g of 1,1'-bis(diphenylphosphino)ferrocenedichloropalladium.dichloromethane complex, 1.20 g of 1,1'-bis(diphenylphosphino)ferrocene and 21.20 g of potassium acetate were added, and the mixture was stirred for 7 hours under reflux. The mixture was filtrated through a glass filter paved with 40 g of celite, and washed with hexane. The resultant filtrate was concentrated, to obtain 42.13 g of a crude product as a black oil. This crude product was dissolved in 200 ml of hexane, and 4.2 g of activated charcoal was added and the mixture was stirred at room temperature for 1 hour, then, filtrated through a glass filter paved with celite; and the resultant filtrate was concentrated, to obtain 30.76 g of a compound B-2 represented by the following formula.

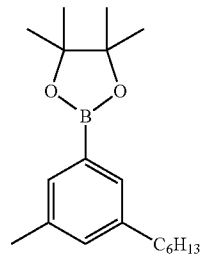

*GC-MS 302 ([M]$^+$, exact mass=302)

Synthesis of Compound B-3

An atmosphere in a 300 ml four-necked flask was purged with nitrogen, and 8.00 g of 3,5-dibromophenol and 25.87 g of the compound B-2 were dissolved in 160 ml of toluene. Dichlorobis(triphenylphosphine)palladium (0.11 g) was added, then, 70 ml of a 20 wt % triethyl ammonium hydroxide aqueous solution was dropped over a period of 5 minutes, then, the mixture was stirred for 4.5 hours under reflux. After left to cool, the solution was allowed to separate, and the aqueous phase was extracted with 100 ml of toluene twice, the resultant organic phases were combined and washed with 50 ml of saturated aqueous solution of sodium chloride. The organic phase after washing was passed through a glass filter paved with 60 g of silica gel and washed with toluene, then, the solvent was distilled off from the resultant organic phase, to obtain 17.33 g of a crude product. The crude product was purified by silica gel column chromatography (mobile phase, hexane:ethyl acetate=96:4 (volume ratio)), to obtain 3.83 g of a compound B-3 represented by the following formula.

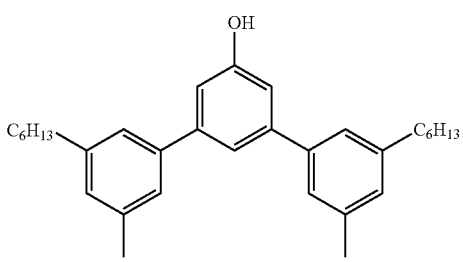

*LC-MS
ESI positive 481 ([M+K]$^+$, exact mass=442)
*$^1$H-NMR (300 MHz, CDCl$_3$)
δ 0.89 (6H, t), 1.25-1.42 (12H, m), 1.60-1.71 (4H, m), 2.40 (6H, s), 2.63 (4H, t), 4.82 (1H, s), 7.01 (4H, s), 7.22-7.26 (4H, m), 7.35 (1H, s)
*$^{13}$C-NMR (300 MHz, CDCl$_3$)
δ 14.4, 21.8, 22.9, 29.4, 31.9, 32.0, 36.3, 113.2, 119.4, 124.8, 125.7, 128.8, 138.5, 141.1, 143.7, 144.0, 156.2

Synthesis of Compound B-4

An atmosphere in a 500 ml flask was purged with nitrogen, and 3.80 g of the compound B-3 was dissolved in 70 ml of dehydrated dichloromethane, and 1.83 g of 4-dimethylaminopyridine was added, then, the mixture was cooled down to 0° C. in an ice bath. Into this, 4.59 g of anhydrous trifluoromethanesulfonic acid was dropped, the ice bath was removed, and the mixture was stirred for 1 hour. The mixture was cooled down to 0° C., and 30 ml of a saturated ammonium chloride aqueous solution was dropped, and the solution was allowed to separate. The aqueous phase after phase-separation was extracted with 50 ml of hexane, the resultant organic phases were combined and washed with 20 ml of water and 20 ml of saturated aqueous solution of sodium chloride. The organic phase after washing was filtrated through a glass filter paved with 10 g of silica gel, and the solvent was distilled off from the resultant organic phase, to obtain 4.70 g of a compound B-4 represented by the following formula.

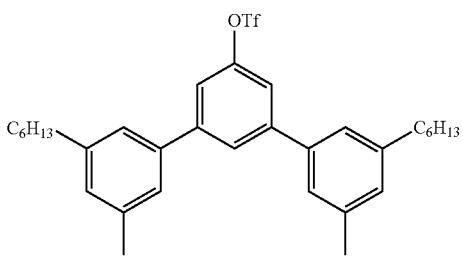

The compound was used in the next step without purification.
*LC-MS
ESI positive 613 ([M+K]$^+$, exact mass=574)
*$^1$H-NMR (300 MHz, CDCl$_3$)
δ 0.89 (6H, t), 1.25-1.42 (12H, m), 1.60-1.71 (4H, m), 2.42 (6H, s), 2.65 (4H, t), 7.06 (2H, s), 7.20 (2H, s), 7.22 (2H, s), 7.39 (2H, s), 7.75 (1H, s)
*$^{13}$C-NMR (300 MHz, CDCl$_3$)
δ 14.4, 21.7, 22.9, 29.4, 31.9, 32.0, 36.2, 118.6, 124.8, 125.7, 126.3, 129.6, 138.9, 139.5, 144.1, 144.8, 150.5

Synthesis of Compound B-5

An atmosphere in a 300 ml four-necked flask was purged with nitrogen, and 4.60 g of the compound B-4 and 1.54 g of phenoxazine were charged therein and dissolved in 70 ml of dehydrated toluene. To this was added 73 mg of tris(dibenzylideneacetone)dipalladium, 89 mg of 1,1'-bis(diphenylphosphino)ferrocene and 3.91 g of cesium carbonate, and the mixture was stirred for 40 hours under reflux. During the reaction, 2 g of cesium carbonate, 73 mg of tris(dibenzylideneacetone)dipalladium and 89 mg of 1,1'-bis(diphenylphosphino)ferrocene were additionally added. After left to cool, 50 ml of water was added, the solution was allowed to separate, and the aqueous phase was extracted with 50 ml of hexane twice. The resultant organic phases were combined and washed with water and saturated aqueous solution of sodium chloride, and the organic phase after washing was filtrated through a glass filter paved with 10 g of silica gel and washed with hexane, and the solvent was distilled off from the resultant organic phase, to obtain 6.15 g of a crude product. The crude product was purified by silica gel column chromatography (500 g of silica gel, mobile phase: hexane singly), to obtain 2.89 g of a compound B-5 represented by the following formula.

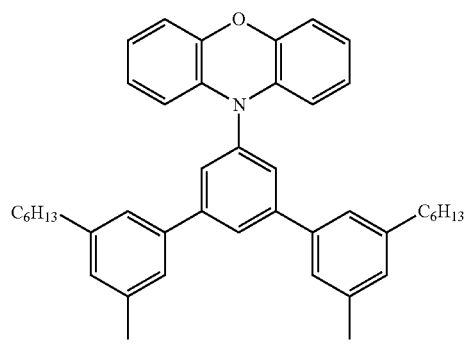

*LC-MS
APPI positive 608 ([M+H]$^+$, exact mass=607)
*$^1$H-NMR (300 MHz, CDCl$_3$)
δ 0.88 (6H, t), 1.26-1.43 (12H, m), 1.60-1.71 (4H, m), 2.41 (6H, s), 2.64 (4H, t), 6.09 (2H, d), 6.60-6.74 (6H, m), 7.03 (2H, s), 7.28 (4H, d), 7.53 (2H, s), 7.89 (1H, s)
*$^{13}$C-NMR (300 MHz, CDCl$_2$)
δ 14.4, 21.8, 22.9, 29.4, 31.9, 32.0, 36.3, 113.7, 123.6, 124.7, 125.6, 126.2, 129.2, 138.8, 140.2, 144.0, 145.3

Synthesis of Compound B

An atmosphere in a 100 ml two-necked flask was purged with nitrogen, and 2.80 g of the compound B-5 was charged therein and dissolved in 30 ml of dehydrated chloroform. The resultant solution was cooled down to 0° C., and 0.25 g of N-bromosuccinimide was added every 5 minutes until reaching 1.50 g, then, further 0.09 g of N-bromosuccinimide was added to a total amount of 1.59 g, then, the mixture was heated up to room temperature and stirred for 3 hours. The resultant solution was cooled down to 0° C., then, 30 ml of an aqueous solution containing 30 mg of sodium thiosulfate dissolved therein was added, and the mixture was stirred. The resultant solution was separated, then, the aqueous phase was extracted with 30 ml of chloroform twice, and the resultant organic phases were combined and filtrated through a glass filter paved with 10 g of silica gel. The solvent was distilled off from the resultant organic phase, to obtain 3.61 g of a crude product. Re-crystallization thereof was repeated using a mixed solution of isopropanol 50 ml/hexane 10 ml, to obtain 1.92 g of a compound B represented by the following formula.

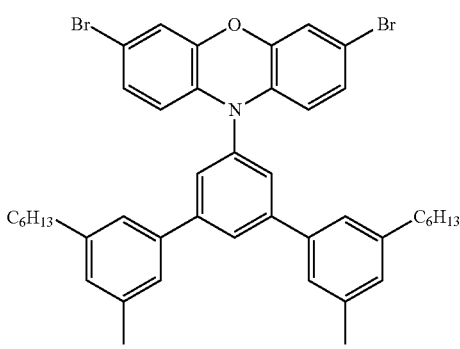

*LC-MS
APCI positive 764 ([M+H]$^+$, exact mass=763)
*$^1$H-NMR (300 MHz, CDCl$_3$)
δ 0.89 (6H, t), 1.26-1.40 (12H, m), 1.60-1.70 (4H, m), 2.41 (6H, s), 2.64 (4H, t), 5.94 (2H, d), 6.73 (2H, d), 6.83 (2H, s), 7.05 (2H, s), 7.25 (2H, s), 7.27 (2H, s), 7.46 (2H, s), 7.90 (1H, s)
*$^{13}$C-NMR (300 MHz, CDCl$_3$)
δ 14.4, 21.8, 22.9, 29.4, 32.0, 36.3, 113.1, 114.9, 118.9, 124.6, 125.5, 126.7, 127.6, 129.4, 133.6, 138.9, 140.0, 144.1, 144.4, 145.7

Example 4

Synthesis of Polymer Compound 3

A polymer compound 3 was synthesized (yielded amount; 2.98 g) in the same manner as in Comparative Example 1, excepting that 2.70 g of the compound B was used instead of 1.66 g of 3,7-dibromo-10-(4-butylphenyl)-10H-phenoxazine in Comparative Example 1. The polymer compound 3 had a polystyrene-equivalent number average molecular weight of 4.7×10$^4$ and a polystyrene-equivalent weight average molecular weight of 1.4×10$^5$.

Example 5

Synthesis of Polymer Compound 4

Under a nitrogen atmosphere, 1.59 g of 2,7-bis(1,3,2-dioxaborolan-2-yl)-9,9-di-n-octylfluorene, 1.11 g of N,N'-bis(4-bromophenyl)-N,N'-bis(4-tert-butyl-2,6-dimethylphenyl)-1,4-phenylenediamine (synthesized according to a method described in JP-A No. 2005-314682), 1.65 g of the compound A, 2.4 mg of dichlorobis(triphenylphosphine)palladium(0), 0.45 g of trioctylmethyl ammonium chloride (manufactured by Aldrich, trade name: Aliquat 336) and 30 ml of toluene were mixed and the mixture was heated at 90° C. Into the resultant mixed solution, 6.4 ml of a 17.5 wt % sodium carbonate aqueous solution was dropped, and the mixture was refluxed for 5 hours. After the reaction, to this was added 27 mg of phenylboric acid, and the mixture was refluxed further for 4 hours. Then, to this was added 20 ml of a 12.5 wt % sodium ethyldithiacarbamate aqueous solution, and the mixture was stirred at 85° C. for 2 hours. The resultant solution was cooled, then, washed with 80 ml of water twice, with 80 ml of a 3 wt % acetic acid aqueous solution twice and with 80 ml of water twice, and the resultant solution was dropped into 930 ml of methanol, then, the solution was filtrated to obtain a precipitate. This precipitate was dissolved in 190 mL of toluene, and purified by passing through a column having active alumina paved on silica gel. The resultant toluene solution was dropped into 930 ml of methanol, the solution was stirred, then, the resultant precipitate was filtrated and dried, to obtain 2.01 g of a polymer compound 4. The polymer compound 4 had a polystyrene-equivalent number average molecular weight of 1.7×10$^4$ and a polystyrene-equivalent weight average molecular weight of 3.3×10$^4$.

Example 6

Synthesis of Polymer Compound 5

Into a 300 ml four-necked flask was charged 0.86 g of trioctylmethyl ammonium chloride (manufactured by Aldrich, trade name: Aliquat 336), 0.95 g of the compound A, 3.29 g of 2,7-dibromo-9,9-bis[4-(n-hexyloxy)phenyl]fluorene (synthesized according to a method described in JP-A No. 2007-70620) and 3.10 g of 2,7-bis(1,3,2-dioxaborolan-2-yl)-9,9-di-n-octylfluorene, and an atmosphere in the flask was purged with nitrogen. To this was added 50 ml of toluene which had been bubbled with argon, and the mixture was bubbled for 30 minutes while stirring. To this was added 4.5 mg of dichlorobis(triphenylphosphine)palladium(II) and 12 ml of a 2M sodium carbonate aqueous solution, and the mixture was stirred at 105° C. for 7 hours, then, 0.52 g of phenylboric acid dissolved in a mixed solution of 20 ml of toluene and 25 ml of tetrahydrofuran was added at 105° C., and the mixture was stirred for 3 hours. To this was added an aqueous solution prepared by dissolving 5 g of sodium N,N-diethyldithiocarbamate in 40 ml of water, and the mixture was stirred at 90° C. for 3 hours. To this was added 400 ml of toluene, and the resultant reaction solution was subjected to phase-separation, and the organic phase was washed with 250 ml of water four times, then, dropped into 2.5 L of methanol, to find generation of a precipitate. This precipitate was filtrated, and dried under reduced pressure, then, dissolved in 150 ml of toluene, and passed though a silica gel-alumina column and washed with 350 ml of toluene. The resultant toluene solution was dropped into 2.5 L of methanol, to find generation of a precipitate. This precipitate was filtrated, dried under reduced pressure, then, dissolved in 150 ml of toluene and the solution was dropped into 2.5 L of methanol, to find generation of a precipitate. This precipitate was filtrated and dried under reduced pressure, to obtain 4.74 g of a polymer compound 5. The polymer compound 5 had a polystyrene-equivalent number average molecular weight of 9.4×10$^4$ and a polystyrene-equivalent weight average molecular weight of 2.3×10$^5$.

Comparative Example 2

Synthesis of Polymer Compound 6

A polymer compound 6 (yielded amount: 4.04 g) was synthesized in the same manner as in Example 6, excepting that 0.41 g of 3,7-dibromo-10-(4-butylphenyl)-10H-phenoxazine was used instead of 0.95 g of the compound A in Example 6. The polymer compound 6 had a polystyrene-equivalent number average molecular weight of 8.1×10$^4$ and a polystyrene-equivalent weight average molecular weight of 2.0×10$^5$.
<Measurement of Fluorescence Spectrum>
For measurement of a fluorescence spectrum, a 0.8 wt % toluene solution of a polymer compound to be measured was spin-coated on quartz, thereby fabricating a film of the polymer compound. This film was excited with a wavelength of 350 nm, and the fluorescence spectrum of the polymer compound was measured using a spectrofluorometer (manufactured by HORIBA, Ltd., trade name: Fluorolog). The fluorescence peak wavelength (fluorescence peak) (nm) and the CIE chromaticity coordinate judged from the resultant fluorescence spectrum are shown in Table 1.

TABLE 1

|  | Polymer compound | Fluorescence peak | Chromaticity coordinate |
|---|---|---|---|
| Example 2 | 1 | 456 | (0.15, 0.14) |
| Example 4 | 3 | 461 | (0.14, 0.15) |
| Example 5 | 4 | 454 | (0.15, 0.14) |
| Example 6 | 5 | 458 | (0.14, 0.14) |
| Comparative Example 1 | 2 | 462 | (0.15, 0.18) |
| Comparative Example 2 | 6 | 460 | (0.14, 0.20) |

Example 7

Fabrication of Light Emitting Device

On a glass substrate with an ITO film having a thickness of 150 nm formed thereon by a sputtering method, a solution of poly(ethylenedioxythiophene)/polystyrenesulfonic acid (manufactured by H.C. Starck, trade name: CLEVIOS P AI4083) was spin-coated to form a film having a thickness of 65 nm, and this was dried on a hot plate at 200° C. for 10 minutes.

Next, the polymer compounds 2 to 5 were dissolved in xylene each at a concentration of 1.5 wt % to prepare solutions. Thus prepared solutions were spin-coated at a rotational speed of 1000 rpm to form films. The film thicknesses were about 60 nm. The films were dried under a nitrogen gas atmosphere at 130° C. for 10 minutes, then, as a cathode, barium was vapor-deposited with a thickness of about 5 nm, then, aluminum was vapor-deposited with a thickness of about 60 nm, to fabricate light emitting devices. After the degree of vacuum reached $1 \times 10^{-4}$ Pa or less, metal vapor deposition was initiated.

Voltage was applied on the resultant light emitting devices, to observe blue EL emission. The light emission peak wavelength (EL peak) (nm) and the CIE chromaticity coordinate judged from the light emission spectrum in application of a voltage of 8 V are shown in Table 2.

TABLE 2

|  | Polymer compound | EL peak | Chromaticity coordinate |
|---|---|---|---|
| Example 4 | 3 | 460 | (0.17, 0.18) |
| Example 5 | 4 | 455 | (0.16, 0.16) |
| Example 6 | 5 | 460 | (0.14, 0.13) |
| Comparative Example 1 | 2 | 465 | (0.20, 0.25) |

INDUSTRIAL APPLICABILITY

The polymer compound of the present invention is a polymer compound excellent in chromatic purity (particularly, red, blue, green). In a preferred embodiment, a light emitting device excellent in luminance half life is obtained by using the polymer compound of the present invention.

The invention claimed is:

1. A polymer compound comprising a residue of a compound represented by the following formula (1):

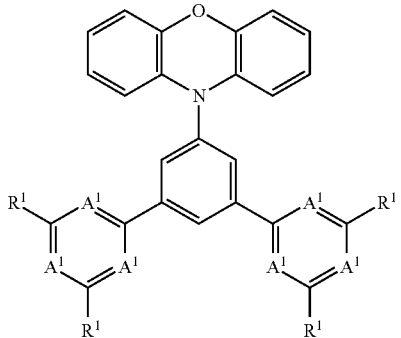

(1)

wherein $R^1$ represents a mono-valent alicyclic hydrocarbon group, an aryl group or a mono-valent heterocyclic group, a group represented by $R^1$ optionally has a substituent, $A^1$ represents —N= or —C($R^2$)=, and $R^2$ represents a hydrogen atom, an alkyl group, an alkoxy group, an aryl group, an aryloxy group, an arylalkyl group, an arylalkoxy group, an alkenyl group, an arylalkenyl group, an alkynyl group, an arylalkynyl group, an amino group, a substituted amino group, a silyl group, a substituted silyl group, a halogen atom, an acyl group, an acyloxy group, an amide group, a mono-valent heterocyclic group, a heterocyclic oxy group, a carboxyl group, a substituted carboxyl group, a nitro group or a cyano group, a group represented by $R^2$ optionally has a substituent, six $A^1$s may be the same or different, and four $R^1$s may be the same or different.

2. The polymer compound according to claim 1 wherein the residue of the compound represented by said formula (1) is a di-valent group represented by the following formula (2):

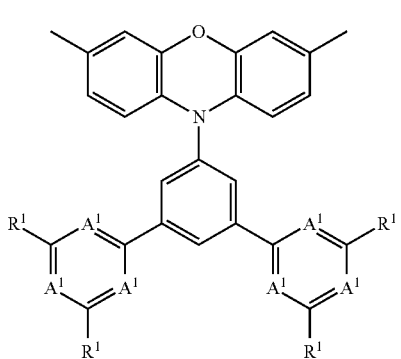

(2)

wherein $A^1$ and $R^1$ represent the same meaning as described above.

3. The polymer compound according to claim 2 wherein the di-valent group represented by said formula (2) is a repeating unit.

4. The polymer compound according to claim 1 wherein said $A^1$ represents —C($R^2$)= and said $R^1$ represents an aryl group.

5. The polymer compound according to claim 1 further comprising a repeating unit represented by the following formula (3):

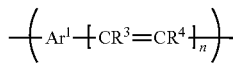

(3)

wherein $Ar^1$ represents an arylene group or a di-valent heterocyclic group, $R^3$ and $R^4$ each independently represent a hydrogen atom, an alkyl groups, an aryl group, a monovalent heterocyclic group or a cyano group, groups represented by $Ar^1$, $R^3$ and $R^4$ optionally have a substituent, and n represents 0 or 1.

6. The polymer compound according to claim 5 wherein the repeating unit represented by said formula (3) is a repeating unit represented by the following formula (4):

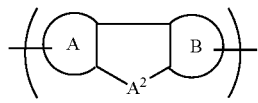

(4)

wherein a ring A and a ring B each independently represent an aromatic hydrocarbon ring or an aromatic heterocyclic ring, and each of the ring A and the ring B has one bond thereon, and $A^2$ represents a di-valent group which is connected to the ring A and to the ring B to form a 5-membered or 6-membered ring.

7. The polymer compound according to claim 6 wherein the repeating unit represented by said formula (4) is a repeating unit represented by the following formula (5):

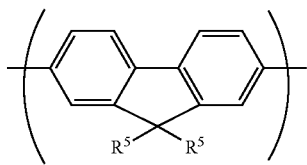

(5)

wherein $R^5$ represents a hydrogen atom, an alkyl group, an aryl group, an arylalkyl group or a mono-valent heterocyclic group, or two $R^5$s may be mutually connected to form a ring, A group represented by $R^5$ optionally has a substituent, and two $R^5$s may be the same or different.

8. The polymer compound according to claim 7 wherein said $R^5$ is an alkyl group.

9. The polymer compound according to claim 7 wherein said $R^5$ is an aryl group.

10. The polymer compound according to claim 1 further comprising a repeating unit represented by the following formula (6):

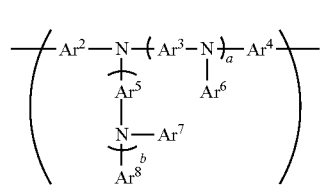

(6)

wherein $Ar^2$, $Ar^3$, $Ar^4$ and $Ar^5$ each independently represent an arylene group or a di-valent heterocyclic group, $Ar^6$, $Ar^7$ and $Ar^8$ each independently represent an aryl group or a mono-valent heterocyclic group, groups represented by $Ar^2$, $Ar^3$, $Ar^4$, $Ar^5$, $Ar^6$, $Ar^7$ and $Ar^8$ optionally have a substituent, a and b each independently represent an integer of 0 or more, when a is 2 or more, a plurality of $Ar^3$s and a plurality of $Ar^6$s may be the same or different, respectively, and when b is 2 or more, a plurality of $Ar^5$s and a plurality of $Ar^7$s may be the same or different, respectively.

11. A composition comprising the polymer compound according to claim 1.

12. A film comprising the polymer compound according to claim 1.

13. An organic transistor having the film according to claim 11.

14. A light emitting device having electrodes consisting of an anode and a cathode, and a layer comprising the polymer compound according to claim 1 disposed between the electrodes.

15. A surface light source using the light emitting device according to claim 14.

16. A display using the light emitting device according to claim 14.

* * * * *